(12) United States Patent
Wawrousek et al.

(10) Patent No.: US 10,231,510 B2
(45) Date of Patent: Mar. 19, 2019

(54) CUSTOMIZED FOOTWEAR, AND SYSTEMS AND METHODS FOR DESIGNING AND MANUFACTURING SAME

(71) Applicant: New Balance Athletics, Inc., Boston, MA (US)

(72) Inventors: Chris Wawrousek, Somerville, MA (US); Daniel P. Dempsey, North Andover, MA (US); Jean-Francois Fullum, North Reading, MA (US); Sean B. Murphy, North Andover, MA (US); Pedro Rodrigues, Amesbury, MA (US); Trampas Tenbroek, North Andover, MA (US)

(73) Assignee: New Balance Athletics, Inc., Boston, MA (US)

( * ) Notice: Subject to any disclaimer, the term of this patent is extended or adjusted under 35 U.S.C. 154(b) by 0 days.

(21) Appl. No.: 14/946,122

(22) Filed: Nov. 19, 2015

(65) Prior Publication Data
US 2016/0135537 A1 May 19, 2016

Related U.S. Application Data

(63) Continuation of application No. 14/134,948, filed on Dec. 19, 2013, now Pat. No. 9,788,600.
(Continued)

(51) Int. Cl.
*A43B 13/14* (2006.01)
*A43B 13/18* (2006.01)
(Continued)

(52) U.S. Cl.
CPC .............. *A43B 13/181* (2013.01); *A43B 5/02* (2013.01); *A43B 5/06* (2013.01); *A43B 7/14* (2013.01);
(Continued)

(58) Field of Classification Search
CPC . A61B 5/1078; A43B 13/181; A43B 13/2013; A43B 13/04; A43B 13/18;
(Continued)

(56) References Cited

U.S. PATENT DOCUMENTS 4,133,118 A * 1/1979 Khalsa .................... A43B 7/14
                                                          36/29
4,297,796 A * 11/1981 Stirtz ..................... A43B 13/18
                                                          36/28
(Continued)

FOREIGN PATENT DOCUMENTS

WO    WO-9937175 A1     7/1999
WO    WO-2006122832 A2  11/2006
WO    WO-2009055451 A1   4/2009

OTHER PUBLICATIONS

Frank T. Piller, "Prior 2 Lever: Footwear Customization with Rapid Manufacturing", Internet Citation, Apr. 20, 2006, pp. 1-3, retrieved from the internet: http://mass-customization.blogs.com/mass_customization_open_i/2006/04/prior_2_lever_f.html.
(Continued)

*Primary Examiner* — Katharine Gracz
(74) *Attorney, Agent, or Firm* — Goodwin Procter LLP

(57) ABSTRACT

The invention relates to devices and methods for designing and manufacturing customized footwear, and components thereof. An exemplary method includes a method of designing at least a portion of a sole of an article of footwear customized for a user. The method includes the steps of determining at least one input parameter related to a user, analyzing the at least one input parameter to determine at least one performance metric of a foot of the user, and determining at least one customized structural characteristic of at least a portion of a sole of an article of footwear for the user based on the performance metric.

23 Claims, 54 Drawing Sheets

Related U.S. Application Data

(60) Provisional application No. 61/739,346, filed on Dec. 19, 2012.

(51) Int. Cl.

| | | |
|---|---|---|
| *A43B 5/02* | (2006.01) | |
| *A43B 5/06* | (2006.01) | |
| *A43B 13/22* | (2006.01) | |
| *A43C 13/04* | (2006.01) | |
| *A43D 1/02* | (2006.01) | |
| *G06F 17/50* | (2006.01) | |
| *A61B 5/103* | (2006.01) | |
| *A43B 13/12* | (2006.01) | |
| *B29C 44/08* | (2006.01) | |
| *B33Y 80/00* | (2015.01) | |
| *A43B 7/14* | (2006.01) | |
| *A43B 13/04* | (2006.01) | |
| *A43B 13/20* | (2006.01) | |
| *A61B 5/107* | (2006.01) | |
| *A61B 5/00* | (2006.01) | |

(52) U.S. Cl.
CPC ............ *A43B 13/04* (2013.01); *A43B 13/125* (2013.01); *A43B 13/14* (2013.01); *A43B 13/141* (2013.01); *A43B 13/18* (2013.01); *A43B 13/203* (2013.01); *A43B 13/223* (2013.01); *A43C 13/04* (2013.01); *A43D 1/02* (2013.01); *A43D 1/025* (2013.01); *A61B 5/1038* (2013.01); *B29C 44/08* (2013.01); *B33Y 80/00* (2014.12); *G06F 17/5086* (2013.01); *A43D 2200/60* (2013.01); *A61B 5/1074* (2013.01); *A61B 5/6807* (2013.01)

(58) Field of Classification Search
CPC ... A43B 13/182; A43B 13/185; A43B 13/186; A43B 13/187; A43B 7/14; A43B 7/141; A43B 13/125; A43B 13/14; A43B 13/223; A43B 5/02; A43B 5/06; A43C 13/04; B29C 44/08; B33Y 80/00; A43D 220/60

See application file for complete search history.

(56) References Cited

U.S. PATENT DOCUMENTS

| | | | | |
|---|---|---|---|---|
| 4,393,604 | A | | 7/1983 | Crowley |
| 4,535,553 | A | * | 8/1985 | Derderian ............ A43B 13/181 36/28 |
| 4,611,412 | A | * | 9/1986 | Cohen ..................... A43B 5/06 36/25 R |
| 4,774,774 | A | * | 10/1988 | Allen, Jr. .............. A43B 13/20 36/28 |
| 5,337,492 | A | * | 8/1994 | Anderie ............... A43B 13/183 36/114 |
| 5,461,800 | A | * | 10/1995 | Luthi .................... A43B 13/181 36/114 |
| 5,839,208 | A | * | 11/1998 | Huang .................. A43B 13/20 36/28 |
| 5,946,824 | A | * | 9/1999 | Tighe ................... A43B 13/181 36/25 R |
| 6,385,864 | B1 | * | 5/2002 | Sell, Jr. ................. A43B 13/20 36/29 |
| 6,763,611 | B1 | * | 7/2004 | Fusco .................. A43B 13/125 36/25 R |
| 6,769,202 | B1 | * | 8/2004 | Luthi .................... A43B 13/184 36/28 |
| 6,826,852 | B2 | * | 12/2004 | Fusco .................... A43B 13/12 36/103 |
| 6,955,094 | B1 | | 10/2005 | Tarler |
| 7,159,338 | B2 | * | 1/2007 | LeVert ................. A43B 13/182 36/27 |
| 7,383,647 | B2 | * | 6/2008 | Chan ..................... A43B 7/142 36/27 |
| 7,707,743 | B2 | * | 5/2010 | Schindler ............. A43B 1/0009 36/25 R |
| 8,056,263 | B2 | * | 11/2011 | Schindler ............. A43B 1/0009 36/25 R |
| 8,109,012 | B2 | * | 2/2012 | Sarantakos ............. A43B 5/08 36/11.5 |
| 8,365,445 | B2 | * | 2/2013 | Sink ..................... A43B 13/145 36/103 |
| 2002/0184791 | A1 | * | 12/2002 | Ko ......................... A43B 3/105 36/8.1 |
| 2002/0189132 | A1 | * | 12/2002 | Yamamoto ............ A43B 13/14 36/3 B |
| 2007/0163147 | A1 | | 7/2007 | Cavanagh et al. |
| 2007/0266593 | A1 | * | 11/2007 | Schindler ............. A43B 1/0009 36/28 |
| 2009/0126225 | A1 | * | 5/2009 | Jarvis ..................... A43B 13/41 36/29 |
| 2011/0047834 | A1 | | 3/2011 | Baker et al. |
| 2011/0138652 | A1 | * | 6/2011 | Lucas .................. A43B 13/183 36/28 |
| 2011/0247243 | A1 | | 10/2011 | Eder et al. |
| 2013/0145650 | A1 | * | 6/2013 | Seo ....................... A43B 13/04 36/28 |
| 2013/0326908 | A1 | | 12/2013 | Grott et al. |
| 2015/0096195 | A1 | | 4/2015 | Bacon et al. |

OTHER PUBLICATIONS

IET Faraday, "Custom Made Sports Shoes (Rapid Manufacturing)", Internet Citation, Nov. 10, 2008, retrieved from the internet: https://www.youtube.com/watch?v=gFSiZgrdCZM.
International Preliminary Report on Patentability in PCT/US2013/076665 dated Jun. 23, 2015, 10 pages.
International Search Report and Written Opinion in PCT/US2016/037211, dated Sep. 7, 2016 (16 pages).

* cited by examiner

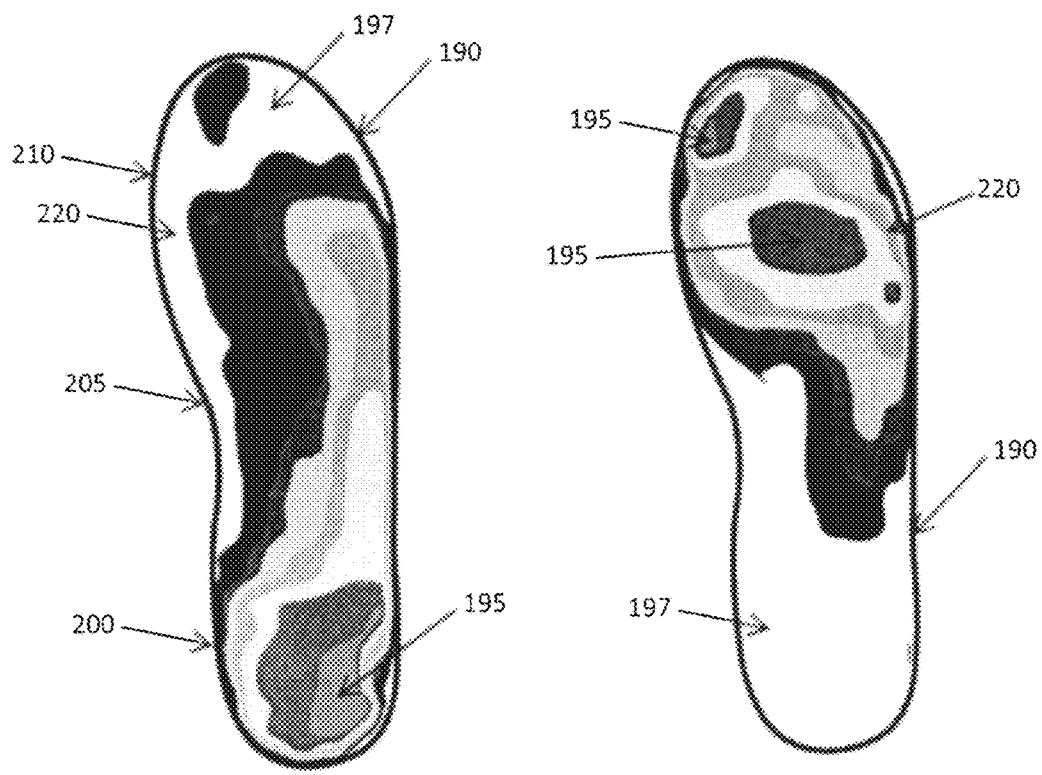
FIG. 6A
FIG. 6B
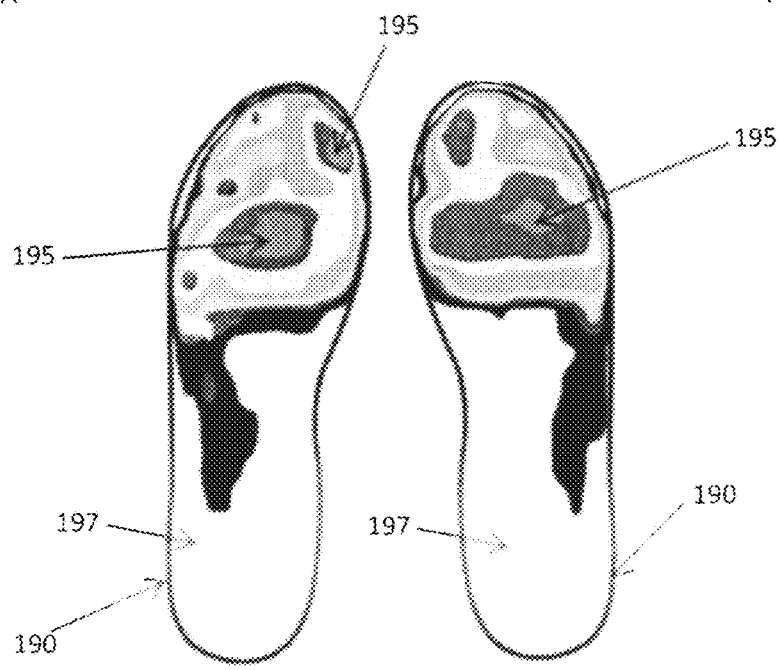
FIG. 6C

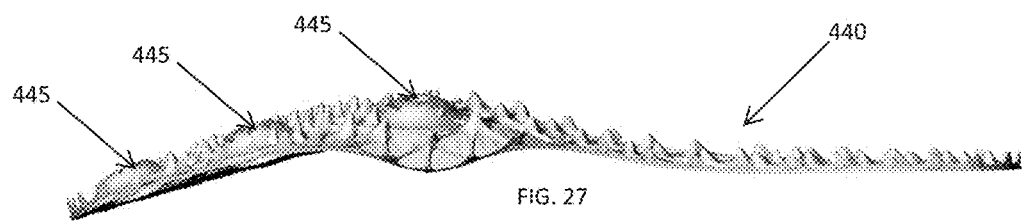
FIG. 27
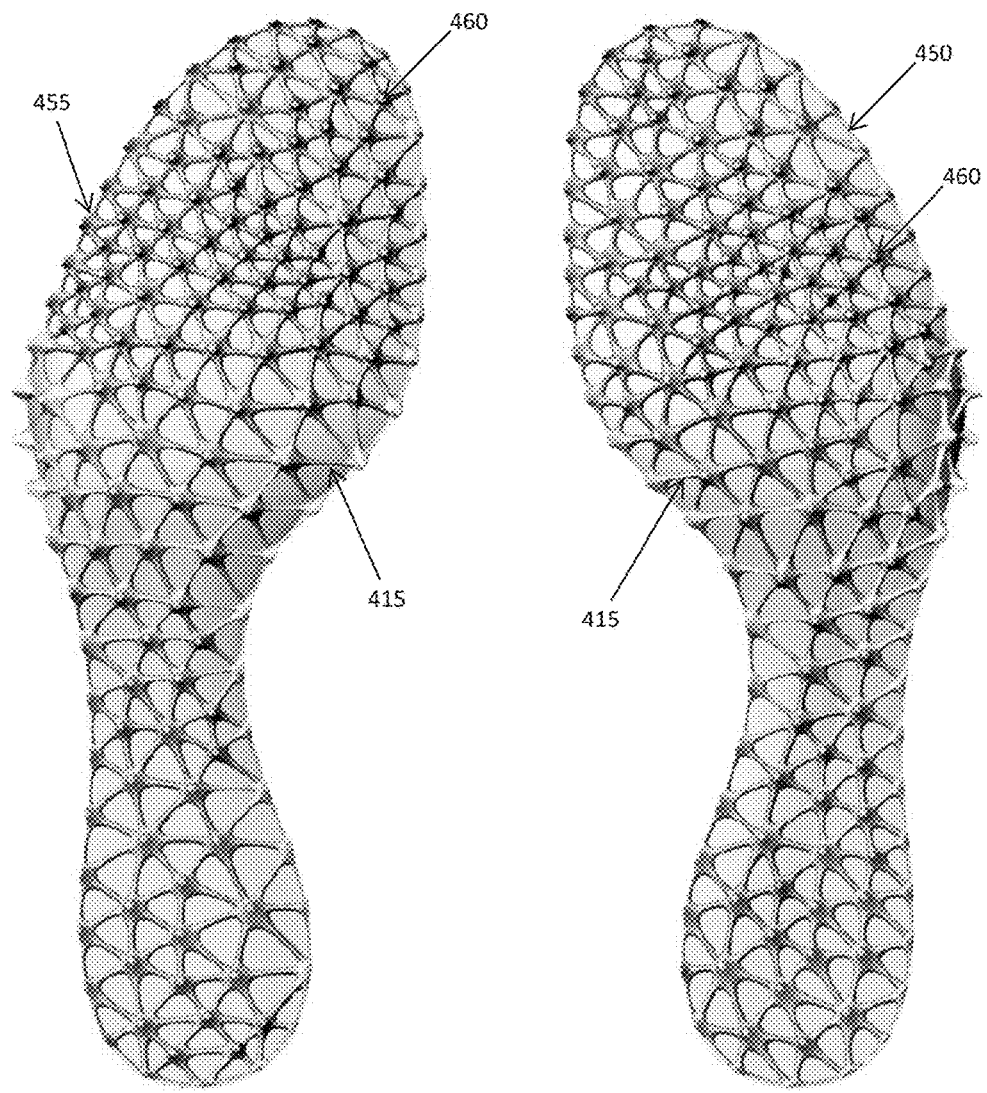
FIG. 28A
FIG. 28B

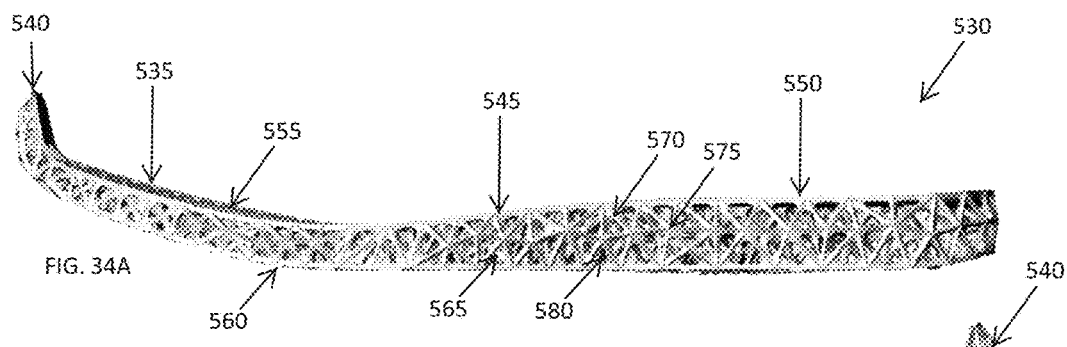
FIG. 34A
FIG. 34B
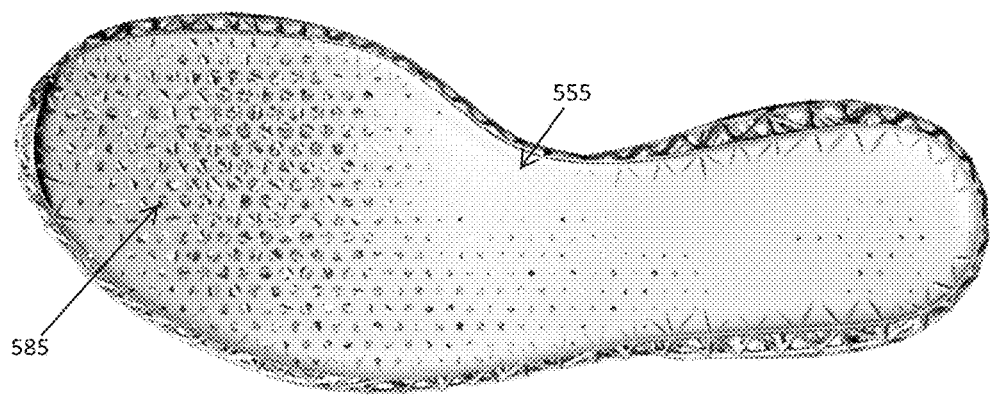
FIG. 34C
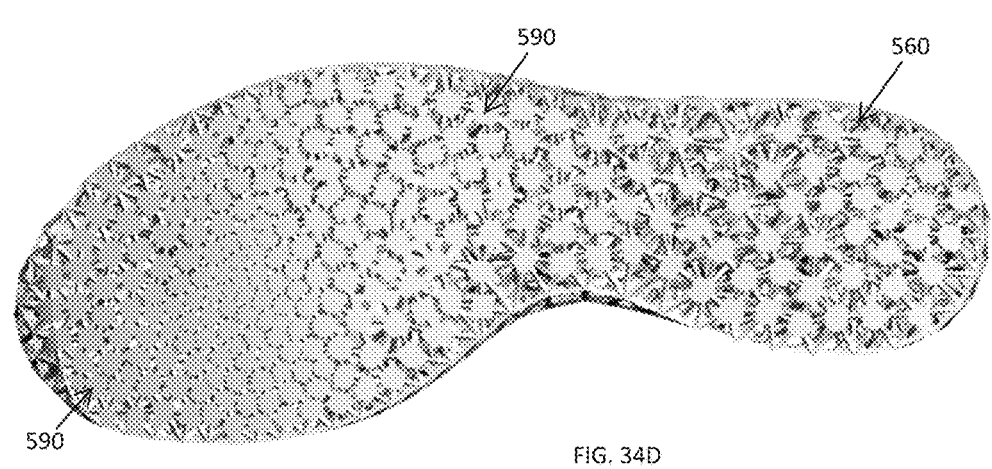
FIG. 34D

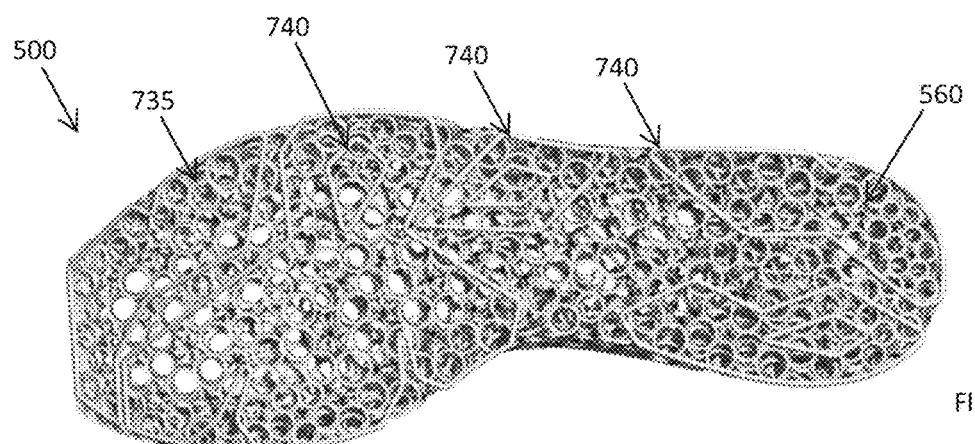
FIG. 40A
FIG. 40B
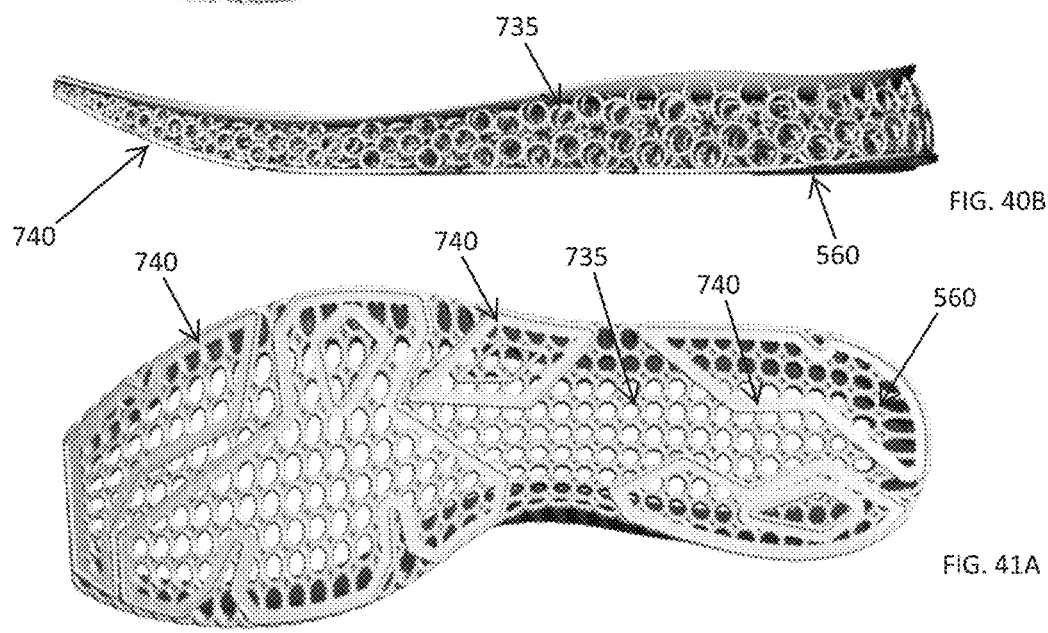
FIG. 41A
FIG. 41B
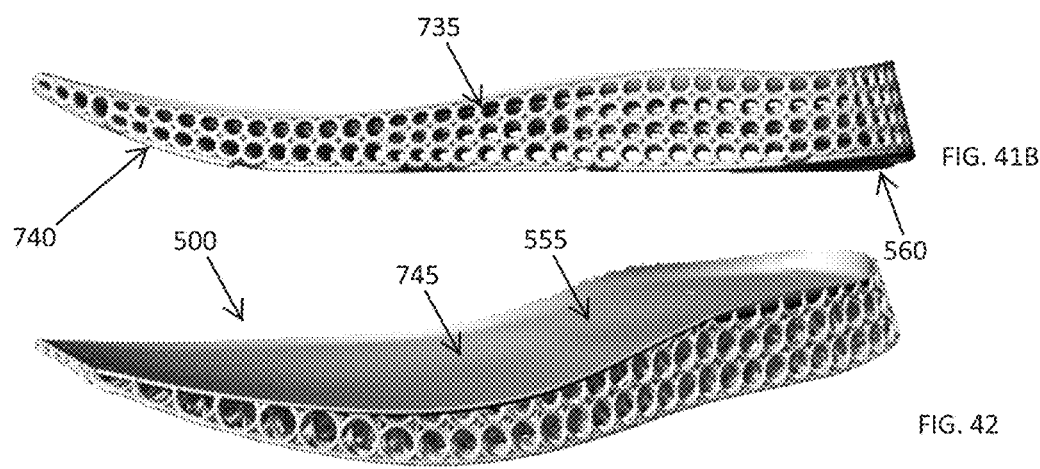
FIG. 42

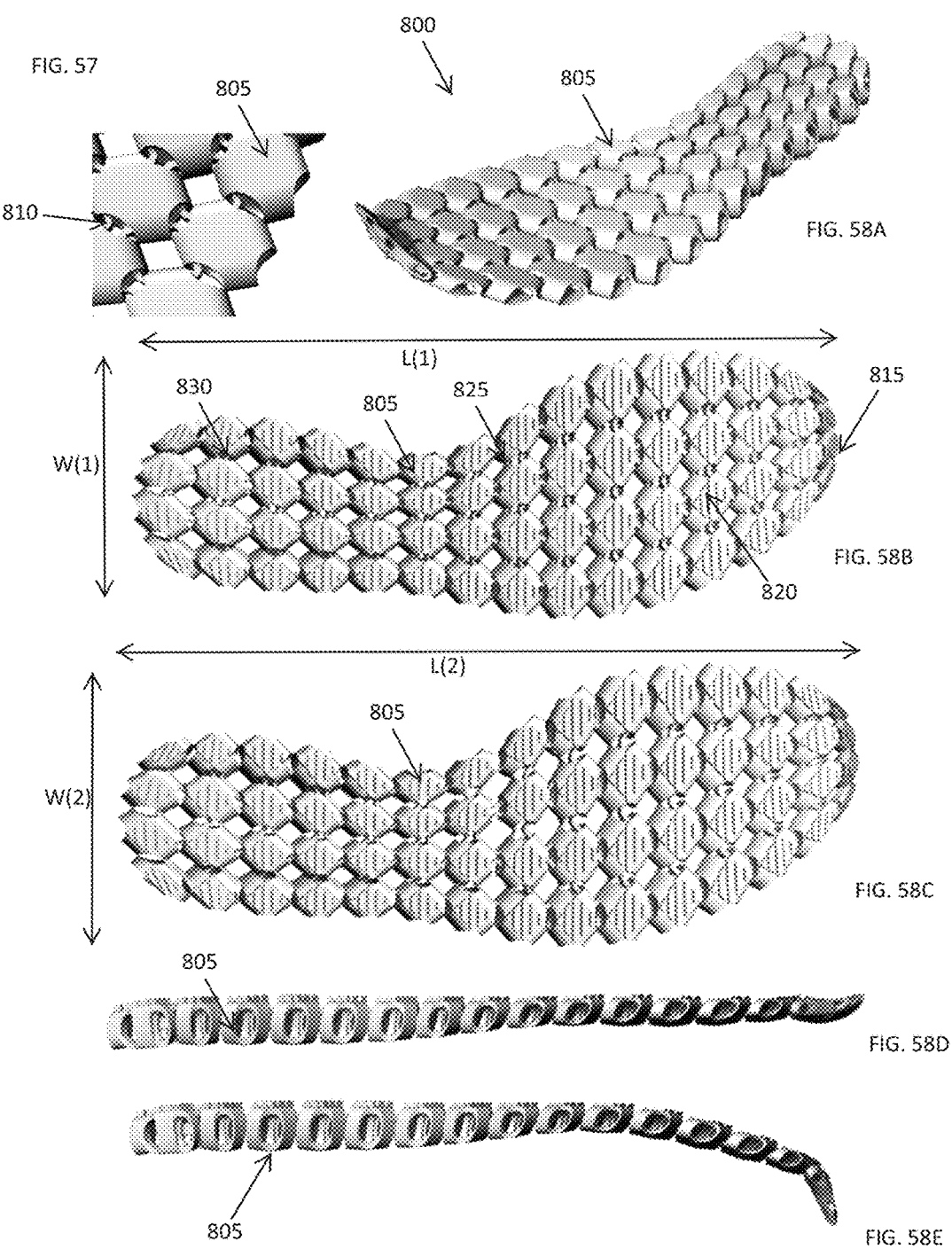

CUSTOMIZED FOOTWEAR, AND SYSTEMS AND METHODS FOR DESIGNING AND MANUFACTURING SAME

CROSS-REFERENCE TO RELATED APPLICATIONS

This application is a continuation application of U.S. patent application Ser. No. 14/134,948, filed on Dec. 19, 2013, which claims priority to and the benefit of U.S. Provisional Patent Application Ser. No. 61/739,346, filed Dec. 19, 2012, the disclosures of which are incorporated herein by reference in their entirety.

FIELD OF THE INVENTION

The present invention relates generally to the field of footwear, apparel, and sporting equipment, and more particularly to customized articles of footwear, apparel, or sporting equipment, and elements thereof, and related systems and methods for designing and manufacturing same.

BACKGROUND OF THE INVENTION

Many aspects of the performance and comfort of articles of footwear are dependent upon various performance and physical characteristics of the wearer of the footwear. For example, stride length, stride rate, footstrike location, pronation/supination, running style, and running speed can be affected by the elements of the footwear being worn. In addition, physical characteristics of the athlete, such as height, weight, shoe size, foot shape, leg shape and size, etc. can affect the performance of the athlete and the article of footwear being worn.

While each individual athlete has a unique set of performance and physical characteristics and a unique set of aesthetic and performance requirements, the athlete has generally been limited when selecting footwear to basic choices such as brand, style, size, width, and (for running spikes and cleated footwear) spike size and shape, with fully customized footwear addressing the specific performance and aesthetic requirements of an individual unavailable under traditional manufacturing techniques and product distribution channels.

SUMMARY OF THE INVENTION

The present invention is directed towards customized footwear, apparel, and sporting equipment, and elements thereof, and related systems and methods for designing and manufacturing same.

One aspect of the invention includes a method of designing at least a portion of a sole of an article of footwear customized for a user. The method includes the steps of determining at least one input parameter related to a user, analyzing the at least one input parameter to determine at least one performance metric of a foot of the user, and determining at least one customized structural characteristic of at least a portion of a sole of an article of footwear for the user based on the performance metric.

In one embodiment determining the at least one input parameter includes measuring at least one characteristic of at least a portion of a foot of the user. The step of measuring at least one characteristic of at least a portion of a foot of the user may include obtaining experimental data representative of a performance characteristic of the foot during at least a portion of a ground contact phase of a gait cycle (or ground contact phase of an athletic motion such as running, jumping, cutting, turning, kicking, etc.). The at least one input parameter may, for example, include at least one of a pressure, a friction, a force, a position, a velocity, an acceleration, a rotational velocity, a rotational acceleration, a change in shape of at least a portion of a foot, a mass distribution, an energy distribution, a stress, a strain, and/or a time over which an event occurs. In one embodiment the input parameter(s) may include a ground contact time, an initial foot-strike location, a toe-off position, a pronation characteristic, and/or a supination characteristic.

In one embodiment the at least one input parameter comprises at least one of: (i) a pressure distribution over at least a portion of a sole of the foot of the user during at least a portion of the ground contact phase of the gait cycle, (ii) a change in shape and/or position of at least a portion of the foot of the user during at least a portion of the ground contact phase of the gait cycle, and/or (iii) a force distribution between at least a portion of the sole of the foot and the ground surface during at least a portion of the ground contact phase of the gait cycle.

Determining the at least one input parameter may include measuring at least one physical characteristic of a foot of the user and, for example, measuring at least a physiological structural characteristic of the foot. The at least one physiological structural characteristic may include at least one of a shape, a size, a wear pattern, an injury profile, a bone structure, a sweat gland distribution, a moisture level, a temperature, a circulation metric, a muscle activity, a friction metric, a blood pressure, a heart rate, a volume change, a hydration level, a perspiration level, a ligament structure, a toe shape, a toe distribution, a heel shape, and/or an arch shape.

The at least one performance metric may include a metric representative of an interaction between the foot of the user and the ground during at least a portion of a ground contact phase of a gait cycle (or ground contact phase of an athletic motion such as running, jumping, cutting, turning, kicking, etc.). The at least one input parameter may include at least one of pressure distribution measurements over at least a portion of a sole of the foot of the user and force distribution measurements between at least a portion of the sole of the foot and the ground surface during at least a portion of the ground contact phase of the gait cycle.

In one embodiment analyzing the at least one input parameter includes converting the pressure distribution measurements and force distribution measurements to a single coordinate system related at least in part to at least a portion of the foot of the user. In one embodiment analyzing the at least one input parameter includes multiplying the pressure distribution measurements and force distribution measurements to determine a performance metric relating at least in part to at least one of an angle and a magnitude of an interaction between the foot and the ground at a plurality of locations on the foot of the user.

The at least one performance metric may include an identification of one or more regions of the foot of the user that is exposed to a higher pressure and/or force during at least a portion of the ground contact phase of the gait cycle and may, for example, include an identification of a direction vector associated with the higher pressure and/or force.

In one embodiment the structural characteristic of at least a portion of the sole of an article of footwear includes one or more traction elements for an outsole, the traction element including at least one of a tread pattern, a traction element shape, a traction element orientation, and/or a traction element configuration. In one embodiment the structural characteristic of at least a portion of the sole of an article of footwear includes at least one of a material distribution and/or a material density distribution and/or a distribution of one or more mechanical structures within a portion of the sole.

The structural characteristic of at least a portion of a sole of the article of footwear can be formed using one or more additive/rapid manufacturing techniques. Exemplary rapid manufacturing techniques include, but are not limited to, selective laser sintering, fused deposition modeling, stereolithography, laminated object manufacturing, or inkjet-based additive manufacturing.

Another aspect of the invention includes an article of footwear including an upper and a sole, wherein at least a portion of the sole comprises at least one structural characteristic customized with respect to at least one performance metric associated with the user.

Yet another aspect of the invention includes a traction element for an article of footwear including a leading edge, a base portion, and an undercut extending between the leading edge to a base portion, wherein the traction element is adapted such that the leading edge is oriented perpendicular to a direction in which optimum traction is required.

Another aspect of the invention includes a method of designing at least a portion of an article of footwear customized for a user. The method includes the steps of determining at least one input parameter related to a user, analyzing the at least one input parameter to determine at least one performance metric of a foot of the user, and determining one or more customized structural characteristic of at least a portion of the article of footwear for the user based on the performance metric.

Another aspect of the invention includes an article of footwear including an upper and a sole, wherein at least one of the upper and the sole comprise at least one element specifically customized for a particular user.

Another aspect of the invention includes a method of designing at least a portion of an article of apparel customized for a user. The method includes the steps of determining at least one input parameter related to a user, analyzing the at least one input parameter to determine at least one performance metric of a body portion of the user, and determining one or more customized structural characteristic of at least a portion of the article of apparel for the user based on the performance metric.

Another aspect of the invention includes a method of designing at least a portion of an article of sporting equipment customized for a user. The method includes the steps of determining at least one input parameter related to a user's utilization of an article of sporting equipment, analyzing the at least one input parameter to determine at least one performance metric of the article of sporting equipment, and determining one or more customized structural characteristic of at least a portion of the article of sporting equipment based on the performance metric.

These and other objects, along with advantages and features of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 6A is a schematic view of a pressure distribution for a foot of an athlete undergoing an initial heel-striking ground contact during a running motion, in accordance with one embodiment of the invention;

FIG. 6B is a schematic view of a pressure distribution for a foot of the athlete of FIG. 6A undergoing a toe-off phase of a running motion;

FIG. 6C is a schematic view of a pressure distribution for both a left and right foot of the athlete of FIG. 6A undergoing a toe-off phase of a running motion while running round a corner portion of an athletic track;

FIG. 27 is a side view of an outsole plate for a shoe of an athlete including base elements for insertable spikes, in accordance with one embodiment of the invention;

FIGS. 28A and 28B are plan views of outsole plates for left and right shoes of an athlete based on measured performance data while running round a corner portion of a track, in accordance with one embodiment of the invention;

FIG. 34A is a lateral side view of another midsole for an article of footwear, in accordance with one embodiment of the invention;

FIG. 34B is a medial side view of the midsole of FIG. 34A;

FIG. 34C is a top view of the midsole of FIG. 34A;

FIG. 34D is a bottom view of the midsole of FIG. 34A;

FIG. 40A is a bottom view of a midsole for an article of footwear having circular cells, in accordance with one embodiment of the invention;

FIG. 40B is a side view of the midsole of FIG. 40A;

FIG. 41A is a bottom view of another midsole for an article of footwear having circular cells, in accordance with one embodiment of the invention;

FIG. 41B is a side view of the midsole of FIG. 41A;

FIG. 42 is a perspective view of a midsole for an article of footwear having circular cells and a top plate, in accordance with one embodiment of the invention;

FIG. 56A is a top view of another foot-form formed using foot scan data, in accordance with one embodiment of the invention;

FIG. 56B is a side view of the foot-form of FIG. 56A;

FIG. 57 is a perspective view of a linkage system for a midsole for an article of footwear, in accordance with one embodiment of the invention;

FIG. 58A is a perspective view of a midsole for an article of footwear incorporating the linkage system of FIG. 57, in accordance with one embodiment of the invention;

FIG. 58B is a bottom view of the midsole of FIG. 58A;

FIG. 58C is another bottom view of the midsole of FIG. 58A, with the linkages slightly extended;

FIG. 58D is a side view of the midsole of FIG. 58C;

FIG. 58E is a side view of the midsole of FIG. 58C with the angles of certain linkages modified;

FIGS. 59A through 59D are perspective views of a variety of outsole plates having cleated traction elements, in accordance with one embodiment of the invention;

FIG. 59E is a bottom view of another outsole plate having cleated traction elements, in accordance with one embodiment of the invention;

FIG. 60A is a bottom view of an outsole plate having cleated traction elements and flex grooves, in accordance with one embodiment of the invention;

FIGS. 60B through 60E are perspective views of a variety of outsole plates having cleated traction elements and flex grooves, in accordance with one embodiment of the invention;

Figure 61A:
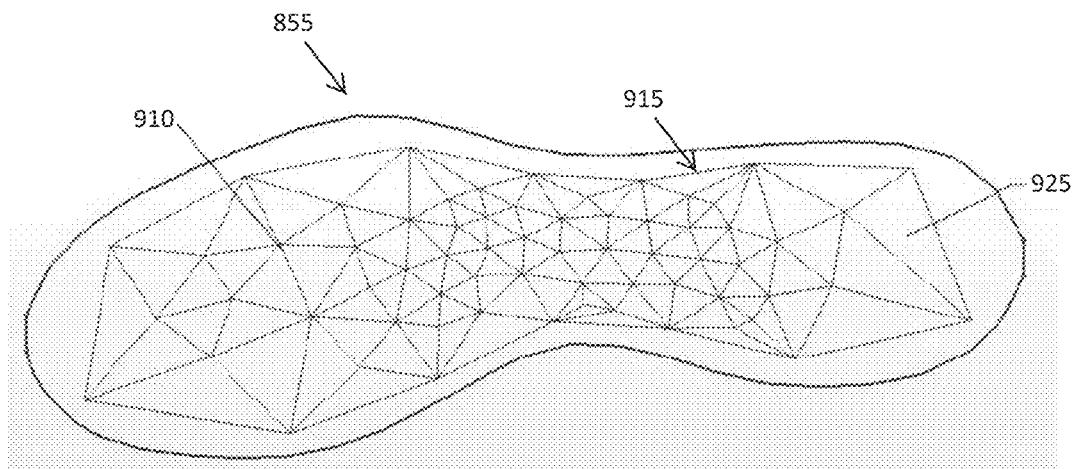
Figure 61B:
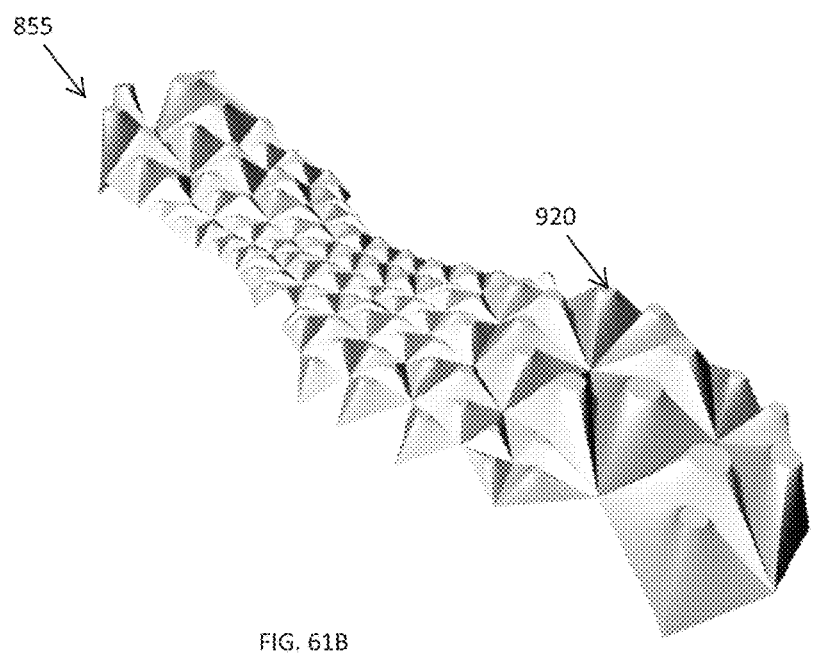
Figures 64A, 64B:
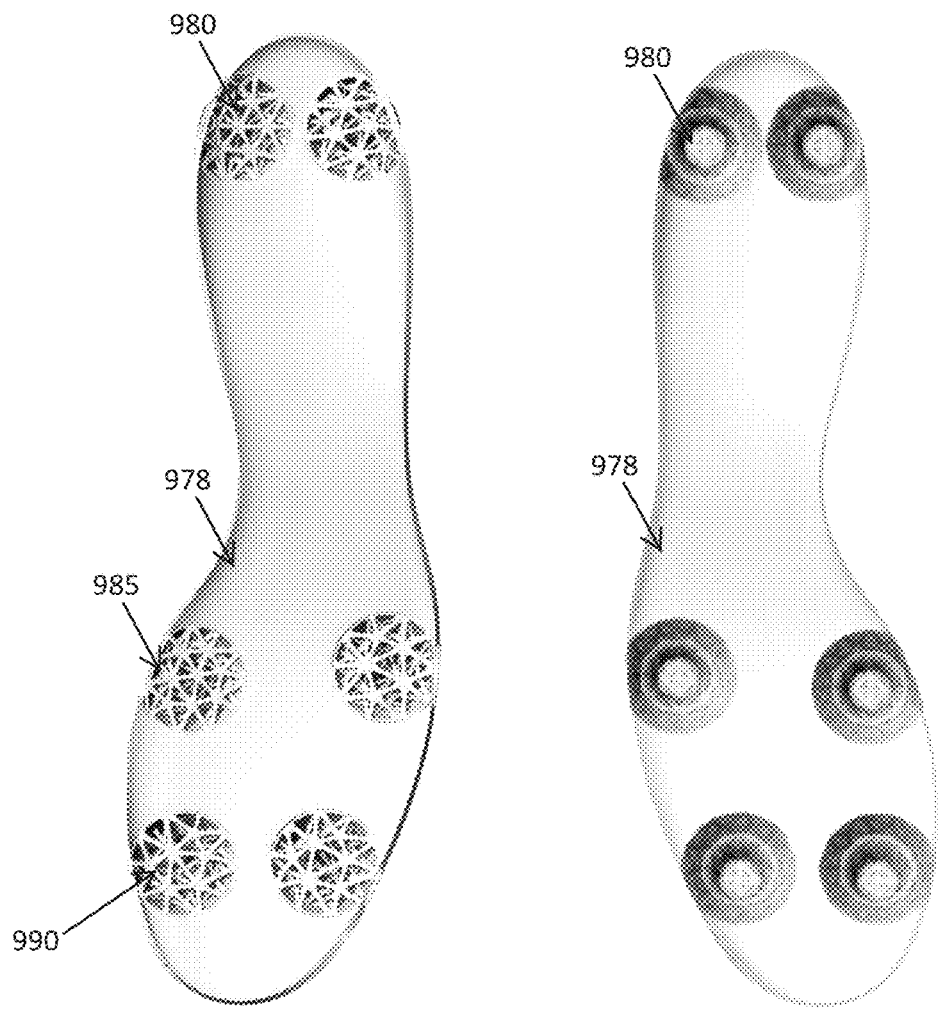

FIG. 61A is a schematic plan view of an outsole plate having a mapping structure superimposed thereon, in accordance with one embodiment of the invention;

FIG. 61B is a cleated outsole plate having cleats in positions corresponding to the mapping structure of FIG. 61A;

FIGS. 62A through 62D are schematic plan views of outsole plates having cleated traction elements positioned and oriented based on various processing algorithms for processing athlete data, in accordance with one embodiment of the invention;

FIGS. 63A through 63G show a number of steps in processing athlete data to produce a customized outsole plate having cleated traction elements, in accordance with one embodiment of the invention;

FIG. 64A is a top view of a cleated sole plate having hollow cleated traction elements, in accordance with one embodiment of the invention;

FIG. 64B is a bottom view of the cleated sole plate of FIG. 64A; and

Figure 65:
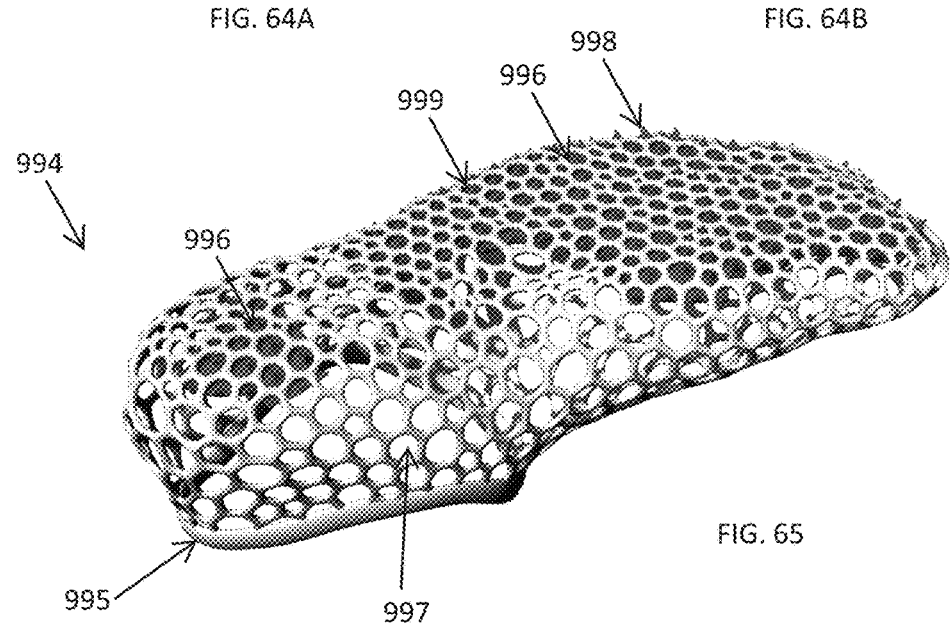

FIG. 65 is a perspective view of an article of footwear including an upper with a ground contact element positioned within, and extending through, the upper, in accordance with one embodiment of the invention.

DETAILED DESCRIPTION

The invention described herein relates generally to methods and systems for designing and manufacturing an article of footwear, apparel, and/or sporting equipment (and, for example, a customized article of footwear), or one or more elements thereof, and customized or non-customized footwear, apparel, and/or sporting equipment manufactured using such methods and systems. More particularly, in one embodiment the invention relates to footwear, or footwear elements, that are specifically customized to meet one or more needs of an athlete to improve the performance of the athlete during athletic activity and/or improve the comfort of the article of footwear when worn.

The customization of footwear may be beneficial for numerous groups of individuals such as, but not limited to, athletes (who are looking for improved performance from their footwear), people with medical conditions (who are looking for footwear providing better support and/or treatment for their specific condition), or casual runners or walkers, who are looking for footwear having both improved and customized performance benefits and/or a customized aesthetic look (including, for example, decorative elements, trademarks, names, etc.). While the description herein relates generally to customizing footwear to provide improved performance characteristics for an athlete, it should be noted that the methods, algorithms, processes, and structures described herein are equally applicable to customization of elements for any purpose and for any user.

Customization of the footwear, or elements thereof, may include factors such as, but not limited to, customized size and shape to better fit a wearer, customized cushioning to address one or more specific characteristic of an athlete's motion, customized traction elements on the outsole (or ground contacting midsole) of the footwear to provide improved grip during a specific athletic activity or activities, customized materials (e.g., specific materials used, material weight, material properties, etc.). Customization may also include specifically creating footwear, and footwear elements, to meet an athlete's individual preferred aesthetic and/or performance needs.

The invention described herein allows for the customization of entire articles of footwear (e.g., shoes, flip-flops, sandals, socks, athletic supports such as compression support elements) and/or the customization of elements of the article of footwear for incorporation into a finished article. Exemplary footwear elements include, but are not limited to, an outsole, midsole, and/or insole for a shoe and/or customized elements for placement within an outsole, midsole, and/or insole such as an element for insertion into or attachment to (e.g., through mechanical attachment, bonding, or other appropriate attachment means) the sole of a shoe at a specific region thereof (e.g., in a heel, midfoot, and/or forefoot region).

Customization of the footwear, or footwear elements, can be based on a number of physical, performance (e.g., kinematic performance), and/or user preference characteristics associated with an individual or group of individuals. For example, in addition to standard parameters such as shoe size, physical characteristics such as the shape of an individual's foot including, for example, bone structure, callous distribution on the foot, injuries (both historical and/or likely in the future), ankle shape, range of motion, strength, toe shape, and preference for hosiery (e.g., socks, tights, or leggings) or no hosiery, and/or strapping (e.g., ankle and/or foot support strapping or taping) to be worn with the footwear can all be accounted for in the design and manufacture of shoes specifically customized for a given wearer or subset of wearers. Other parameters may include, or consist essentially of, breathability characteristics, perspiration characteristics, circulation considerations, and/or diabetes factors (such as, but not limited to, minimization of friction within the shoe).

Additional features of an individual not directly associated with the foot can also have an effect on the athletic performance of the individual, with customized footwear potentially addressing limitations or weaknesses in the individual's mechanics and/or supporting strengths in the individual's mechanics. Such features that may influence customization of the footwear or apparel include, but are not limited to, an individual's height, weight, age, gender, bone structure, leg bone length (e.g., calf length and/or thigh length), general level of physical fitness, medical history and/or medical requirements. Medical requirements that may be addressed through use of customized footwear components may include elements such as structural support for conditions such as, but not limited to, problems with the muscles, tendons, bones, and or skin of the foot such as flat feet, fallen arches, hammer toe, gout, edema (swelling), leg length discrepancy, amputation, hallux deformities or other foot deformities, Morton's neuroma, problems with leg or knee alignment, and/or planar fasciitis, or cushioned and substantially frictionless support for diabetics.

Performance aspects of a specific athlete, or subset of athletes, such as, but not limited to, footstrike location (e.g., heel-strike, midfoot strike, or forefoot strike during initial ground contact of a foot during a gait cycle or other athletic motion), stride length, stride rate (i.e., cadence), pronation or supination of the foot upon foot-strike, pivoting of the foot during ground strike and toe-off, running style, running speed, circulation, breathability, and/or flexibility of one or more joints, may be addressed through customization of the footwear, with specific performance characteristics being supported or compensated for, as needed, to improve the performance of the athlete during athletic activity and/or improve the comfort of the footwear worn during the athletic activity.

In addition, the performance requirements of a specific athletic activity can be taken into account when customizing footwear for a specific athlete or subset of athletes. For example, traction requirements for a runner (such as a track runner, a road runner, or a cross-country runner) may be different depending on whether the runner is a sprinter or long distance runner, and/or whether the runner requires the traction elements on the sole of the footwear to account for running around a corner (e.g., on a standard indoor or outdoor athletic track), or whether the running is to be carried out in a predominantly straight line (e.g., during road racing or jogging). Customization of footwear may also depend upon the weather and underfoot conditions in which the athlete is performing with, for example, different traction requirements being needed for wet/dry conditions and/or soft/firm underfoot conditions. In addition, different sports may require different shapes, sizes, and/or configurations of traction elements (e.g., spikes, cleats or studs, gripping elements, and/or tread patterns) with, for example, cleats for soccer, American football, field hockey, baseball, etc. all requiring different cleat-types and configurations, and with different positions within each of these sports potentially requiring different performance features from the traction elements.

Other athletic activities for which footwear can be customized include activities with significant cutting-type motions (e.g., basketball, baseball, softball, soccer, American football, field hockey, ice hockey, ice skating, speed skating, rugby, tennis, squash, racquetball, skateboarding, cycling, etc.) where an individual's technique and physical characteristics can vary greatly from person to person, and where specifically customized traction elements, support elements, and/or structural support zones can greatly improve the individual's performance of the athletic motion. Other activities such as jumping, crouching, kicking, throwing, turning, spinning, etc. can also be accounted for in creating traction elements that enhance or support the unique combination of performance characteristics of a specific athlete and/or activity.

Customization of footwear for an athlete can be performed, in accordance with various embodiments of the invention, by utilizing analytical tools to process input parameters specific to an athlete (or group of athletes) to generate a design including physical elements specifically located and constructed to address the specific performance and physical characteristics of the athlete. The design can then be manufactured to produce an article of footwear, and/or footwear element, that is unique to the athlete.

Figure 1:
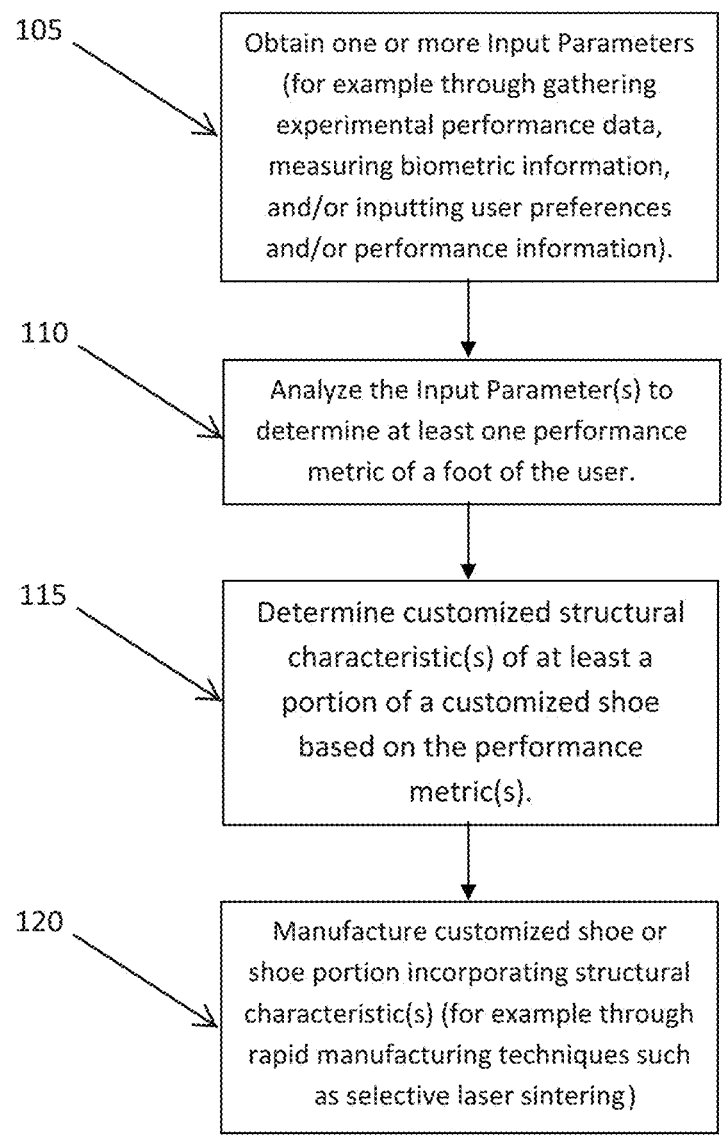
FIG. 1 is a flow chart of a method of designing at least a portion of a sole of an article of footwear customized for a user, in accordance with one embodiment of the invention.

An exemplary method for designing at least a portion of a sole of an article of footwear customized for an athlete is shown in FIG. 1. The method includes the steps of obtaining/determining 105 one or more input parameters related to the athlete and analyzing 110 the input parameters to determine at least one performance metric of a foot of the user. The at least one performance metric is then used to determine 115 one or more structural characteristic of at least a portion of a sole of an article of footwear for the athlete based on the performance metric, after which the customized sole portion can be manufactured 120, for example through use of additive/rapid manufacturing techniques such as, but not limited to, rapid manufacturing methods (e.g., selective laser sintering).

In various embodiments the input parameter(s) can include experimental performance data, measured biometric information, and/or selected user preference and/or performance information. The input parameter(s) may relate directly to one or more characteristic of at least a portion of a foot of the user, and/or include characteristics associated with the legs and/or upper body of the athlete (such as height, weight, leg length, athletic ability, injury, etc.) and/or to the performance requirements of the athletic activity for which the shoe is being customized.

Figure 2:
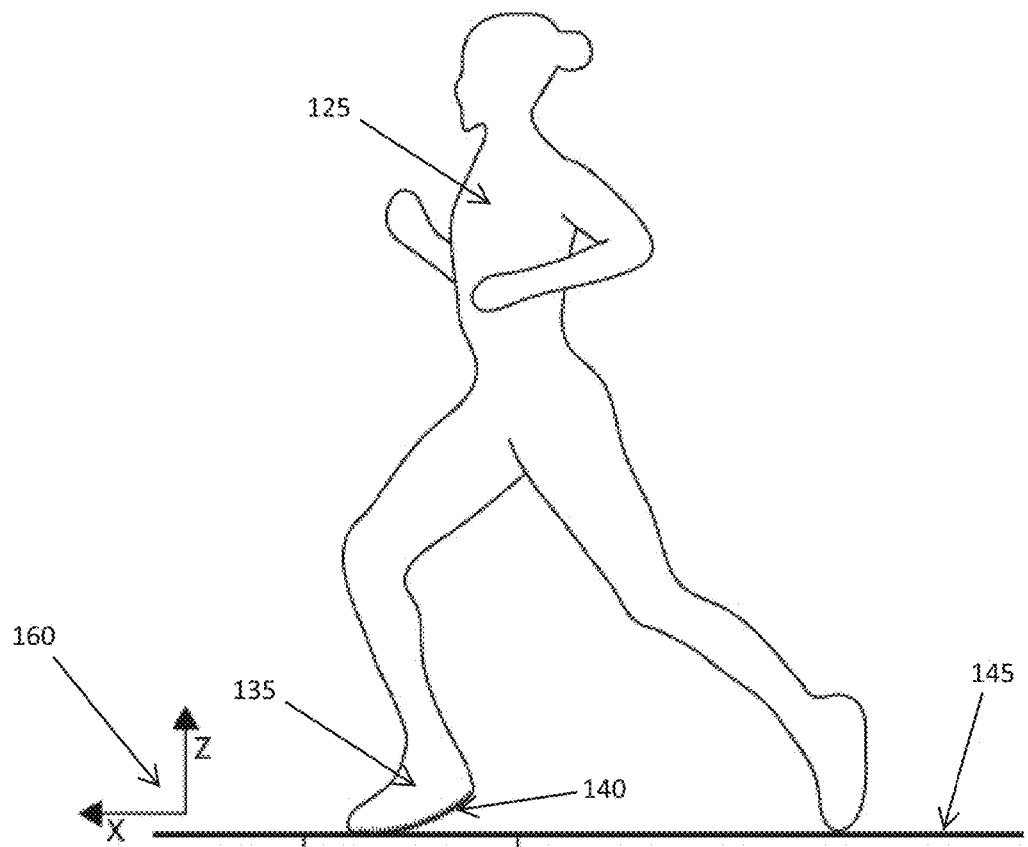
FIG. 2 is a schematic view of a system for obtaining experimental data representative of a performance characteristic of an athlete, in accordance with one embodiment of the invention.
Figure 3:
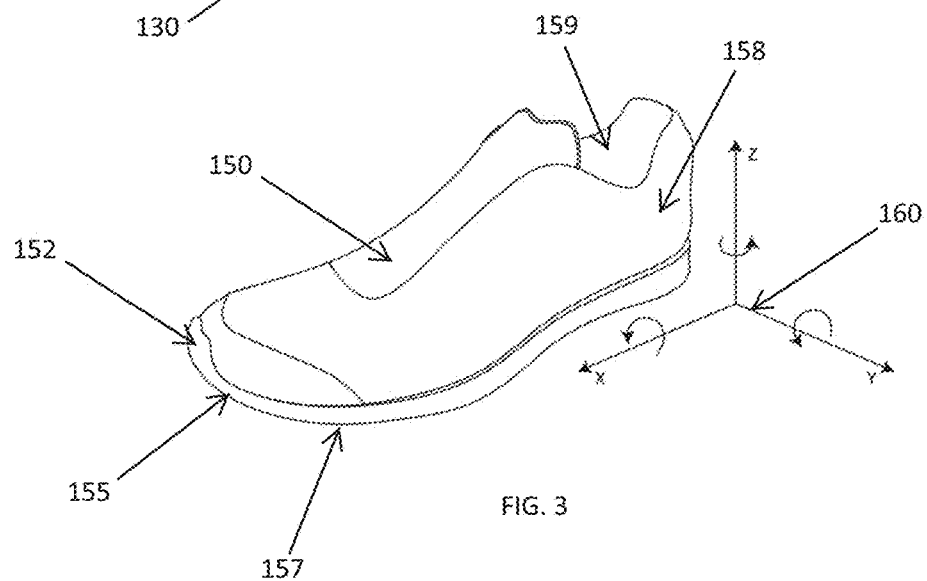
FIG. 3 is a schematic perspective view of an article of footwear, in accordance with one embodiment of the invention.

In one embodiment of the invention the input parameters used to design the customized shoe component include experimental data representative of a performance characteristic of the foot during at least a portion of a ground contact phase of a gait cycle or other athletic motion. An exemplary system for obtaining the experimental data is shown in FIG. 2. In this embodiment, an athlete 125 performs the athletic activity for which the shoe is to be customized (e.g., track running) in an environment including data gathering equipment designed to capture and record data representative of various performance characteristics of the foot of the athlete 125 during the athletic activity. In the example of FIG. 2, the data gathering equipment includes a force plate 130 for capturing the force between the foot 135 of the athlete 125 and the ground 145, and an array of pressure sensors 140 located between the foot 135 and the ground 145. The pressure sensors 140 may be located in an insole placed within a shoe 150 of the athlete 125. In alternative embodiments the pressure sensors 140 can be embedded within a midsole 155 of the shoe 150 or located within or attached to a ground contacting outsole 157 of the shoe 150. Alternatively, or in addition, pressure sensors, or any other sensors utilized in the methods described herein, can be located at any appropriate location on the foot, leg, and/or upper body of an athlete. An exemplary shoe 150 for an athlete 125 is shown in FIG. 3, with an exemplary coordinate system 160 providing axes of orientation for the data capturing systems. The shoe includes an upper 158 and a sole 152 (including an insole and the outsole 157 and midsole 155), with a foot receiving cavity 159 defined by the upper 158 and sole 152. The shoe 150 may be a slip-on style shoe or have tightening/fastening means such as, but not limited to, lacing, hook-and-loop fastening, zippers, cords, elastic elements, buttons, and/or buckles.

In one embodiment the pressure sensors 140 form part of a portable data capture system worn by the athlete 125 during athletic activity, with the pressure sensors 140 located within the shoe 150 and coupled to a data capture system that can power the sensors, record the data obtained from the sensors, and/or wirelessly transmit the data to a data processing system for analysis. In an alternative embodiment the pressure data capture system can merely record the pressure data during athletic activity and then transfer the data to the data processing system through either a wireless or wired connection at a later time. In a further alternative embodiment the data processing system may be located within the portable data capture system.

Figure 5A:
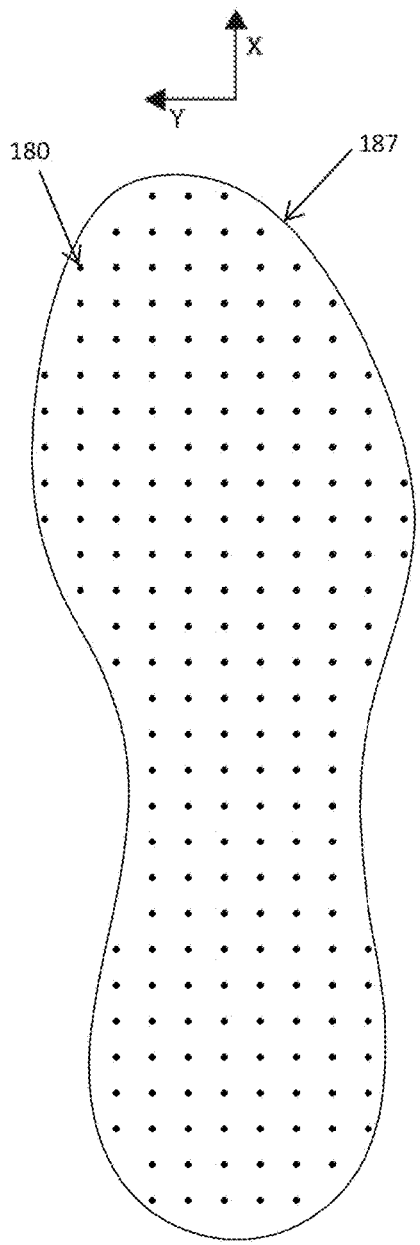
FIG. 5A is a plan view of a pressure sensing insole for an article of footwear, in accordance with one embodiment of the invention.
Figure 5B:
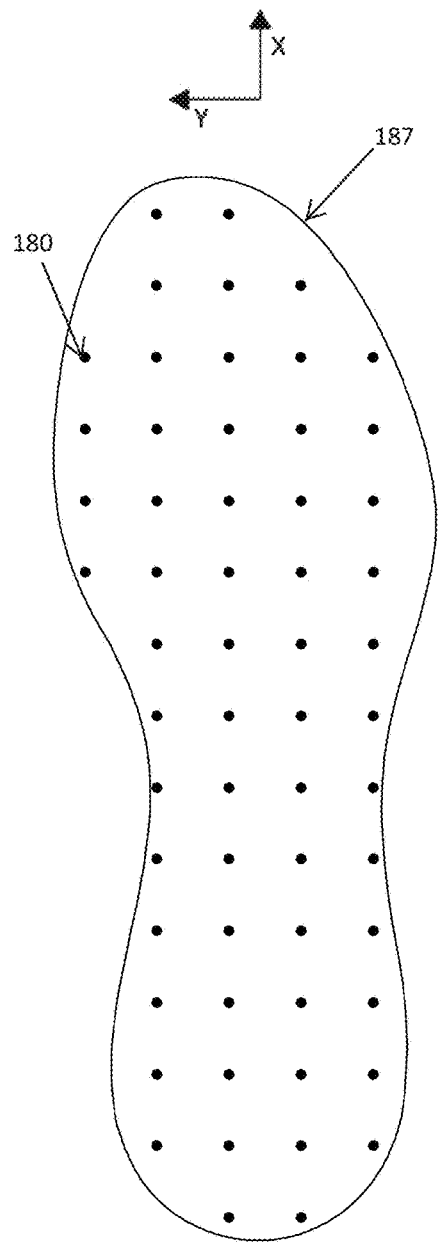
FIG. 5B is a plan view of another pressure sensing insole for an article of footwear, in accordance with one embodiment of the invention.

In one embodiment the pressure sensors 140 include a distribution of separate sensor elements 180 arranged in an array for placing between the sole of the foot 135 and the ground 140 (for example within an insole 187 placed within the shoe 150 of the athlete 125). Exemplary sensor arrays can be seen in FIGS. 5A and 5B, with FIG. 5A showing an array having two hundred and nineteen sensor elements 180 arranged in a regular distribution, and FIG. 5B showing an array having fifty nine sensor elements 180 arranged in a regular distribution. In alternative embodiments any size of sensor array may be utilized (e.g., 10, 20, 50, 99, 100, 200, 500, etc. sensor elements 180), with the sensor elements 180 arranged regularly or in an irregular pattern (e.g., with high importance/impact regions containing more sensor elements 180). As discussed above, each sensor element 180 can form part of a portable data capture including elements for powering the system, recording data from each pressure element 180, and/or transmitting the data for analysis.

In one embodiment the force plate 130 is embedded within, fixed to, or placed on the ground 140, with the athlete running over the force plate 140 during data capture. In an alternative embodiment force sensors may be positioned on or in the sole of the shoe 150 and may form part of the portable data capture system.

Figure 4A:
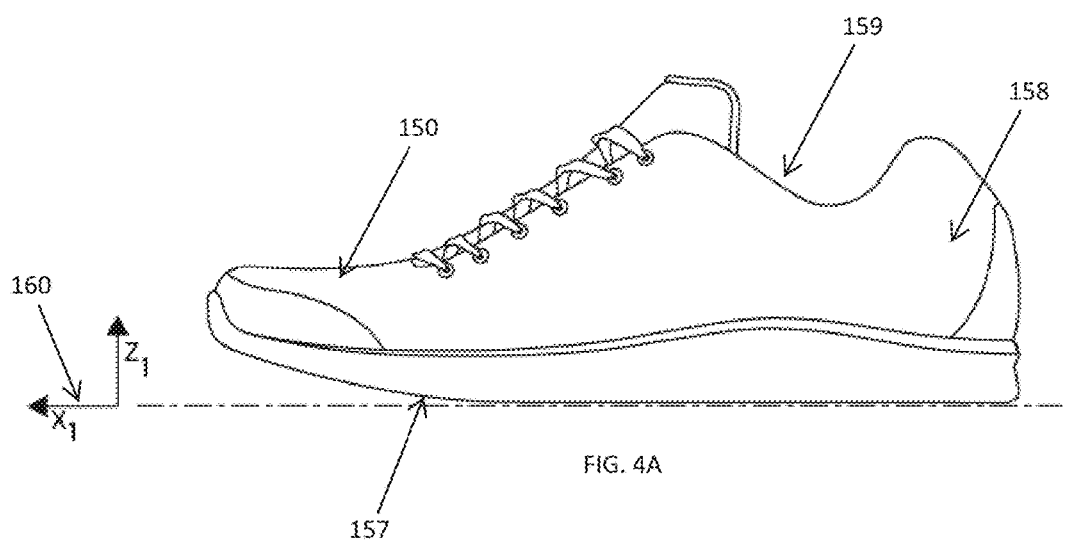
FIG. 4A is a side view of a coordinate system for an article of footwear, in accordance with one embodiment of the invention.
Figure 4B:
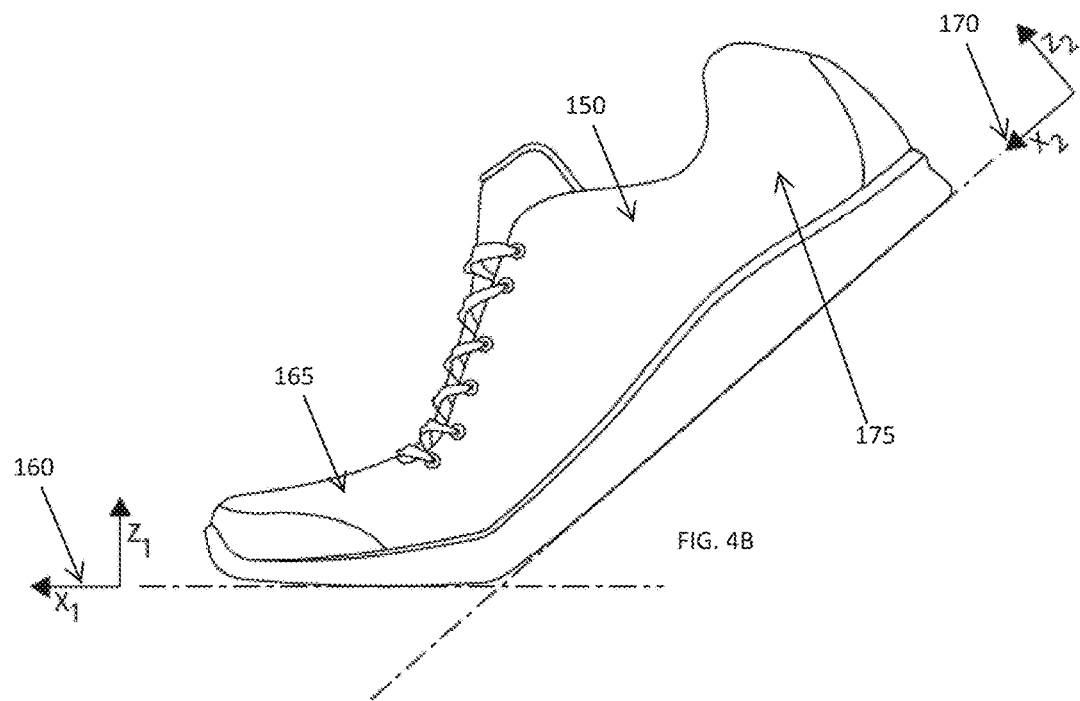
FIG. 4B is a side view of another coordinate system for an article of footwear, in accordance with one embodiment of the invention.

In one embodiment, a single coordinate system associated with either the outsole 155 of the shoe 150, the ground 145, the sole of the foot itself, or any other appropriate element of the foot can be utilized to capture and process the data. An exemplary embodiment with a single coordinate system 160 is shown in FIG. 4A. In an alternative embodiment multiple coordinate systems relating to various elements of the foot 135 and shoe 150 can be utilized. For example, FIG. 4B shows a system having a first coordinate system 160 associated with the forefoot 165 of the shoe 150 and a second coordinate system 170 associated with a heel portion 175 of the shoe 150. Utilizing multiple coordinate systems allows the gathered data to be processed and oriented with respect to the sole of the foot 135, or any other appropriate element of the foot, at numerous locations along the foot 135 regardless of the flexing of the foot during the ground contact phase of the gait cycle. This may, in certain embodiments, allow for more accurate processing and analysis of the data with respect to the performance metrics required for a particular customization goal, although in certain embodiments a single axis system, as shown in FIG. 4A, may be sufficient to provide accurate analytical results.

The system of FIG. 2 allows for the simultaneous measurement of both the pressure distribution over the sole of the foot 135 throughout the ground contact phase of the gait cycle and the force interaction between at least a portion of the sole of the foot and the ground surface during at least a portion of the ground contact phase of the gait cycle. In one embodiment, the pressure sensors 140 measure only the normal pressure between the ground 145 and the foot 135, while the force plate 130 measures the force between foot 135 and ground 140 in all three directions of the coordinate system 160, thereby allowing for the calculation of both the magnitude and vertical and horizontal direction of the force between the foot 135 and ground 140 throughout the ground contact phase. Measuring both normal pressure distribution over the sole of the foot 135 and force vector data allows for the calculation of performance metrics identifying both the magnitude of the force being applied between foot 135 and ground 140 and the direction of that interaction at multiple locations on the foot 135 throughout the ground contact phase.

In an alternative embodiment the pressure sensors 140 may measure the pressure in all three directions of a coordinate system (i.e., normal, posterior, and lateral) associated with the foot 135, thereby allowing for directional data to be obtained without the need for separate three-dimensional force measurements. In a further alternative embodiment, the normal pressure distribution data over the sole of the foot 135 may be integrated with respect to time to produce directional vector data representative of the direction of the force between the foot 135 and the ground 140 throughout the ground contact phase, again allowing for directional data to be obtained without the need for a separate force plate.

Exemplary pressure data for four different athletes can be seen in FIGS. 6A through 9C. More particularly, FIGS. 6A, 7A, 8A, and 9A show pressure distribution data for four athletes at approximately the point of initial contact with the ground during a footstrike, with FIG. 6A showing the pressure distribution for an initial strike of the ground within the region of the heel (a heel-strike) by a first athlete during a straight run, FIGS. 7A and 8A showing the pressure distribution for an initial strike of the ground within the region of the midfoot (a midfoot-strike) for second and third athletes during a straight run, and FIG. 9A showing the pressure distribution for an initial strike of the ground within the region of the forefoot (a forefoot-strike) for a fourth athlete during a straight run. Similarly, FIGS. 6B, 7B, 8B, and 9B show the pressure distribution on the sole of the foot of the four athletes just prior to the foot leaving the ground at the end of the footstrike event (i.e., prior to toe-off) during a straight run. FIGS. 6C, 7C, 8C, and 9C show pressure distributions on both the left and right feet of the four athletes prior to toe-off while the athletes are running around a corner on a standard 400 m athletic track. The pressure distribution maps of FIGS. 6A through 9C show contour maps of pressure in kilopascals (kPa) based on experimental pressure data retrieved from a ninety-nine sensor array embedded within an insole 190 of a shoe of each athlete, with the center(s) 195 of each shaded contour map representing the locations of highest pressure normal to the surface of the insole 190, and the unshaded portions 197 representing areas where no substantial normal pressure was measured (for example because that portion of the foot was not in contact with the ground at that time).

As can be seen, the pressure distributions during the initial footstrike phase of the ground contact vary considerably from athlete to athlete, with the center of pressure for the heel-striking athlete located within the heel region 200, while the center of pressure for the midfoot striking athletes is distributed through the midfoot region 205, and the center of pressure for the forefoot striking athlete is located within the forefoot region 210. In addition, the maximal pressure readings located at the center of pressure in the midfoot striking athletes has a significantly lower maximal value than that measured for the heel striker and forefoot striker, as the load at initial ground contact is distributed over a larger area for a midfoot striker than for a heel and toe striker.

Figure 7A:
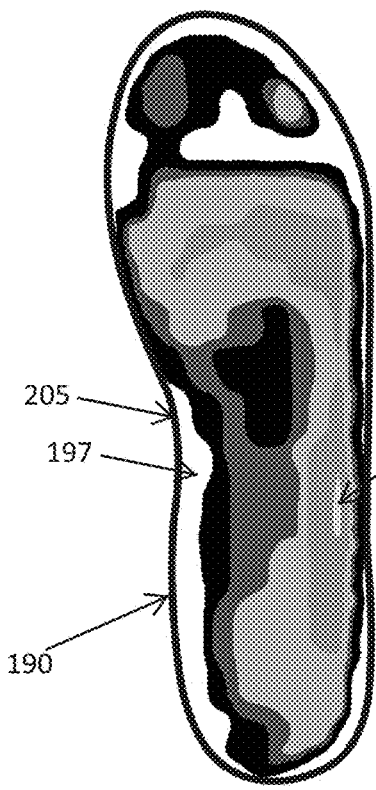
FIG. 7A is a schematic view of a pressure distribution for a foot of an athlete undergoing an initial midfoot-striking ground contact during a running motion, in accordance with one embodiment of the invention.
Figure 7B:
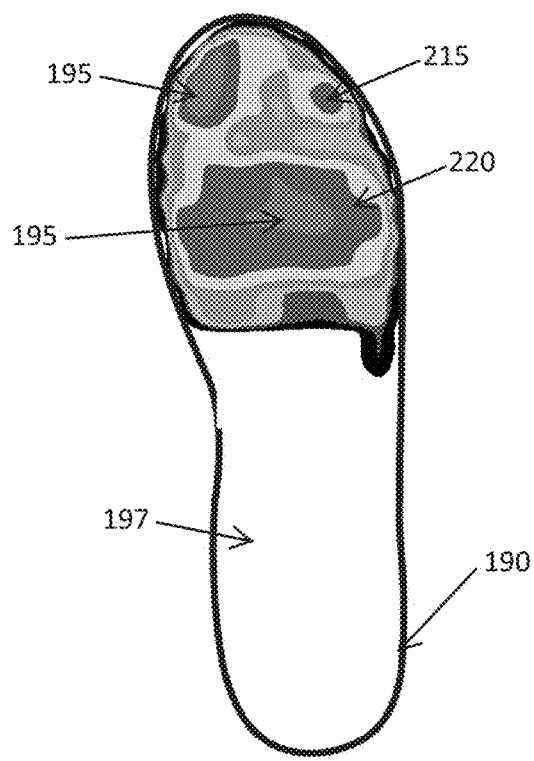
FIG. 7B is a schematic view of a pressure distribution for a foot of the athlete of FIG. 7A undergoing a toe-off phase of a running motion.
Figure 7C:
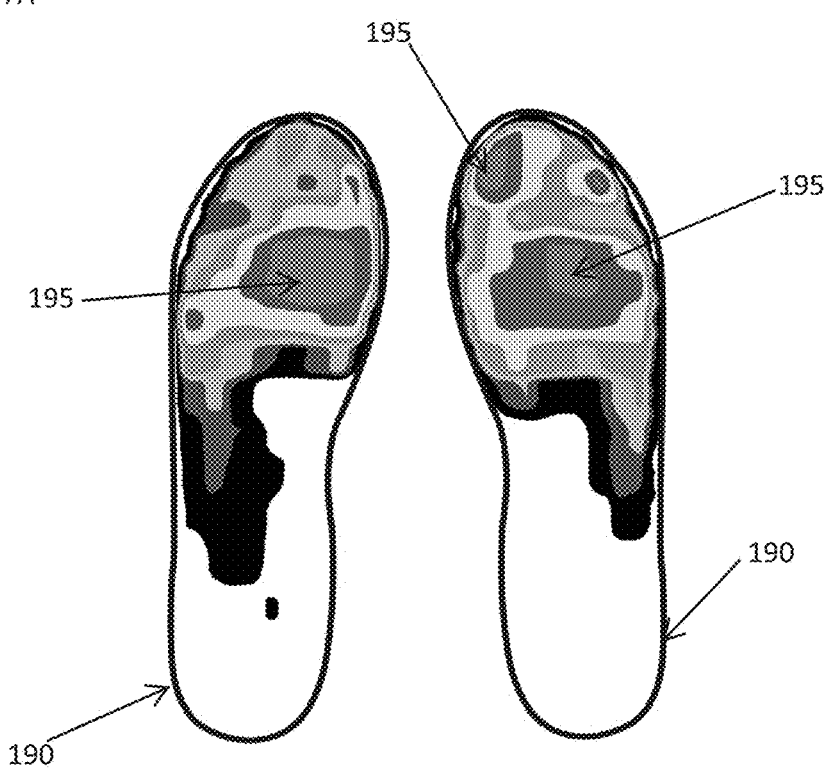
FIG. 7C is a schematic view of a pressure distribution for both a left and right foot of the athlete of FIG. 7A undergoing a toe-off phase of a running motion while running around a corner portion of an athletic track.
Figure 8A:
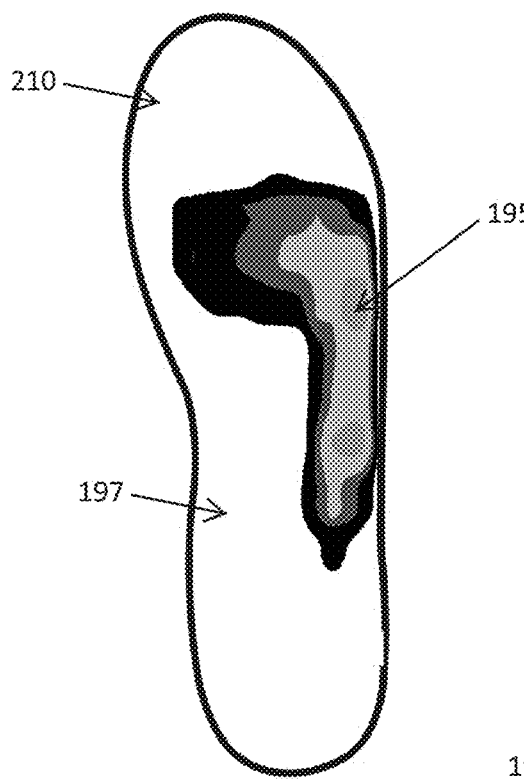
FIG. 8A is a schematic view of a pressure distribution for a foot of another athlete undergoing an initial midfoot-striking ground contact during a running motion, in accordance with one embodiment of the invention.
Figure 8B:
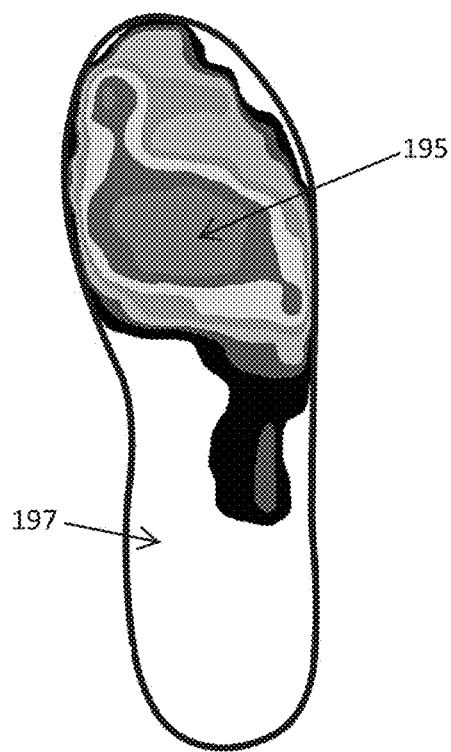
FIG. 8B is a schematic view of a pressure distribution for a foot of the athlete of FIG. 8A undergoing a toe-off phase of a running motion.
Figure 8C:
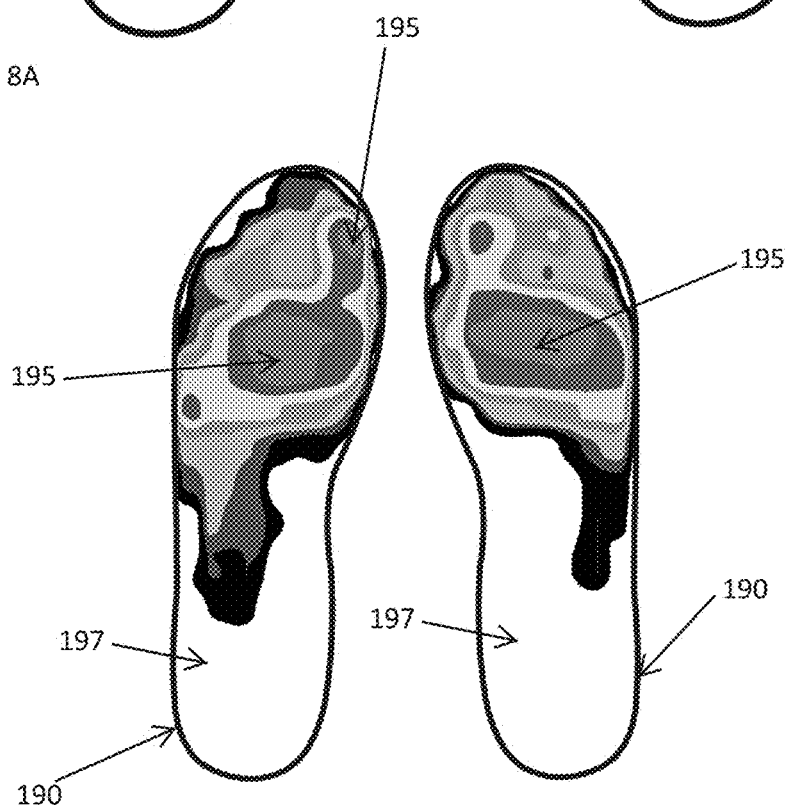
FIG. 8C is a schematic view of a pressure distribution for both a left and right foot of the athlete of FIG. 8A undergoing a toe-off phase of a running motion while running around a corner portion of an athletic track.
Figure 9A:
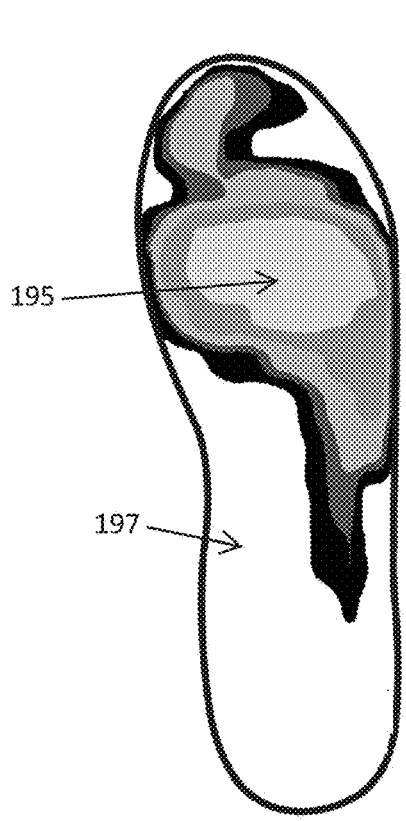
FIG. 9A is a schematic view of a pressure distribution for a foot of another athlete undergoing an initial forefoot-striking ground contact during a running motion, in accordance with one embodiment of the invention.
Figure 9B:
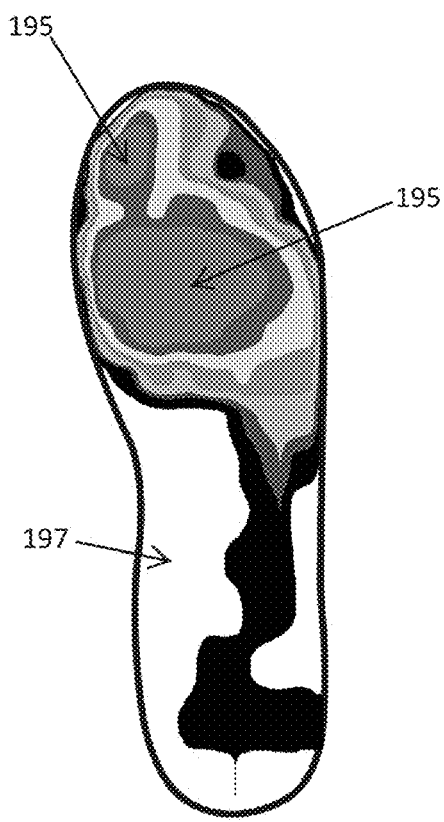
FIG. 9B is a schematic view of a pressure distribution for a foot of the athlete of FIG. 9A undergoing a toe-off phase of a running motion.
Figure 9C:
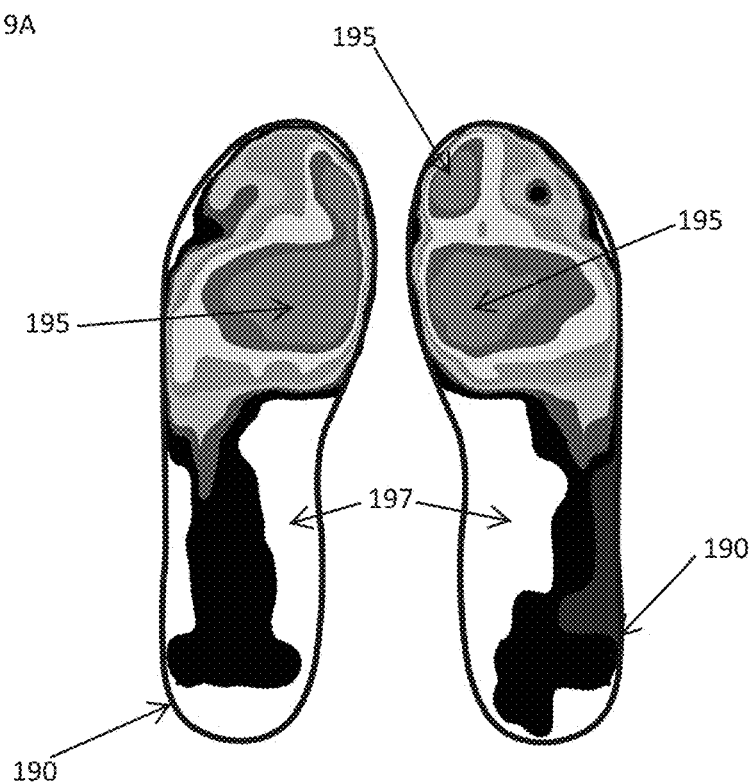
FIG. 9C is a schematic view of a pressure distribution for both a left and right foot of the athlete of FIG. 9A undergoing a toe-off phase of a running motion while running round a corner portion of an athletic track.

While the pressure distributions during the toe-off phase are more similar, again differences in the pressure distributions between athletes can be observed, with the center of pressure and distribution of pressure differing considerably from athlete to athlete. For example, the athlete of FIG. 7B shows a pressure spike near the fourth toe region 215, which is not observed for the other athletes, and each athlete shows a different pressure distribution around their metatarsal head region 220 (i.e., the head of the metatarsal bones adjoining the toe bones). The variation in results at the metatarsal region is due, for example, to variations in running style and also to differences in the shape and configuration of the metatarsal heads in each athlete. As a result, it is clear to see that the interaction between the foot and the ground for different athletes can vary considerably depending, for example, on the running technique of each athlete and the physical characteristics of the foot of each athlete. This identification of the unique features of the ground interaction for a given athlete can be measured and analyzed by appropriate algorithms to ensure that the shoe of the wearer is optimally designed to enhance the performance of each athlete based on their own individual input parameters.

Further variation between the pressure distributions can be seen in FIGS. 6C, 7C, 8C, and 9C, which show the pressure distributions on both the left and right feet of the four athletes prior to toe-off while the athletes are running (in a standard anti-clockwise direction) around a corner on a standard 400 m athletic track. As can be seen, the pressure distributions on the left and right feet of each athlete are not perfectly symmetrical, with the different ground interactions between the ground and the shoe on each foot being affected by the cornering action of the athlete. In addition, while the pressure distributions are not perfectly symmetrical, the force measurements for each foot are significantly different, with the force oriented toward the outer edge of a curved track (i.e., on the inner foot the force is oriented towards the instep of the foot while on the outer foot the force is oriented towards the outer side of the foot). Allowing customization between left and right foot to account for this differentiation in pressure and force distribution may be beneficial for an athlete when running in an event requiring cornering at high speed. In various embodiments the methods and systems described herein can be utilized to provide customized footwear for any type of running track such as, but not limited to, standard 200 m tracks or 400 m tracks and/or tracks having any angle of banking in corners and/or along the straight.

Figures 10A, 10B:
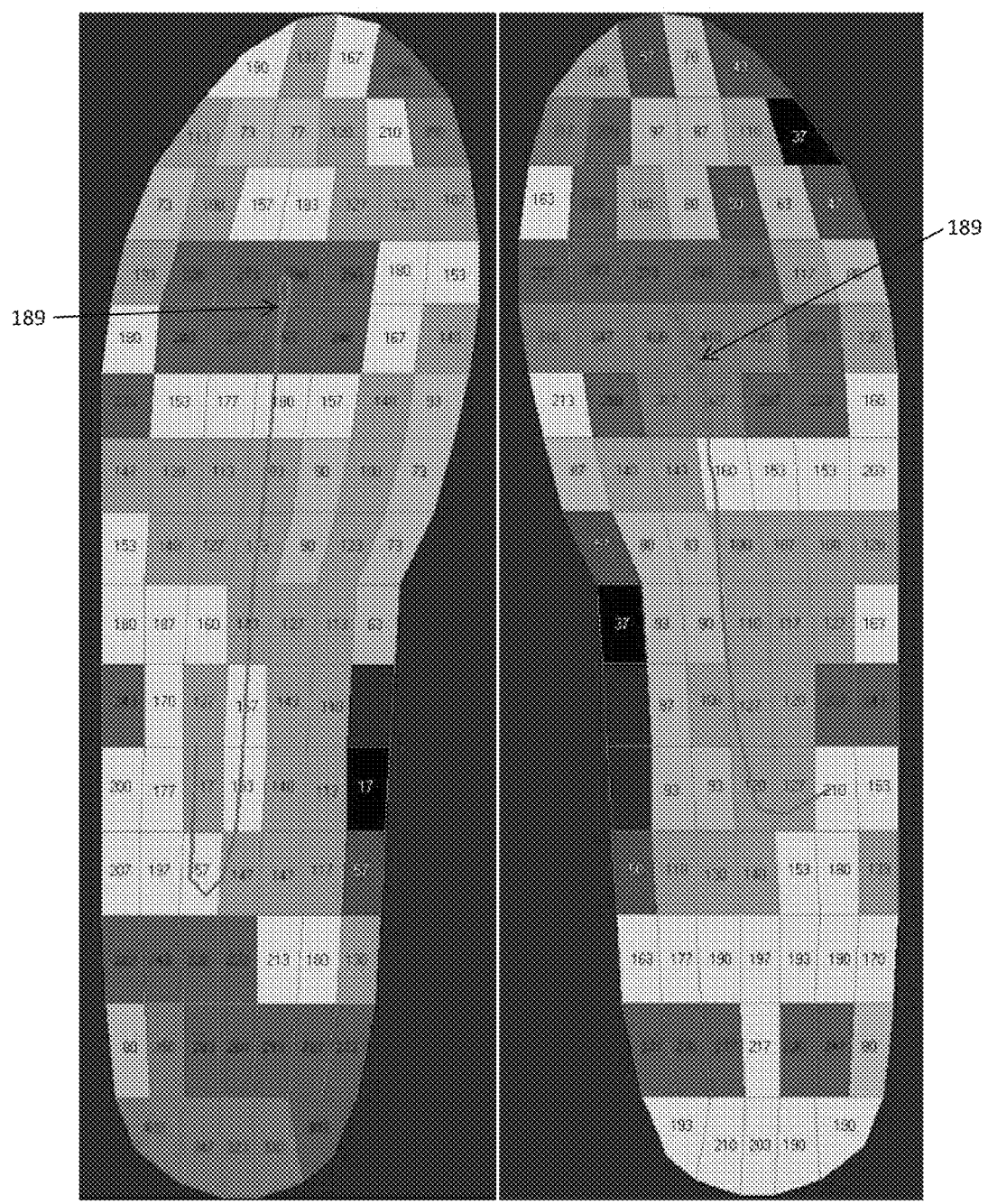
FIG. 10A is a schematic view of pressure data measurements and center of pressure calculations for an athlete undergoing a heel-striking style ground contact phase of a running motion, in accordance with one embodiment of the invention.
FIG. 10B is a schematic view of pressure data measurements and center of pressure data for an athlete undergoing a midfoot-striking style ground contact phase of a running motion, in accordance with one embodiment of the invention.
Figures 10C, 10D:
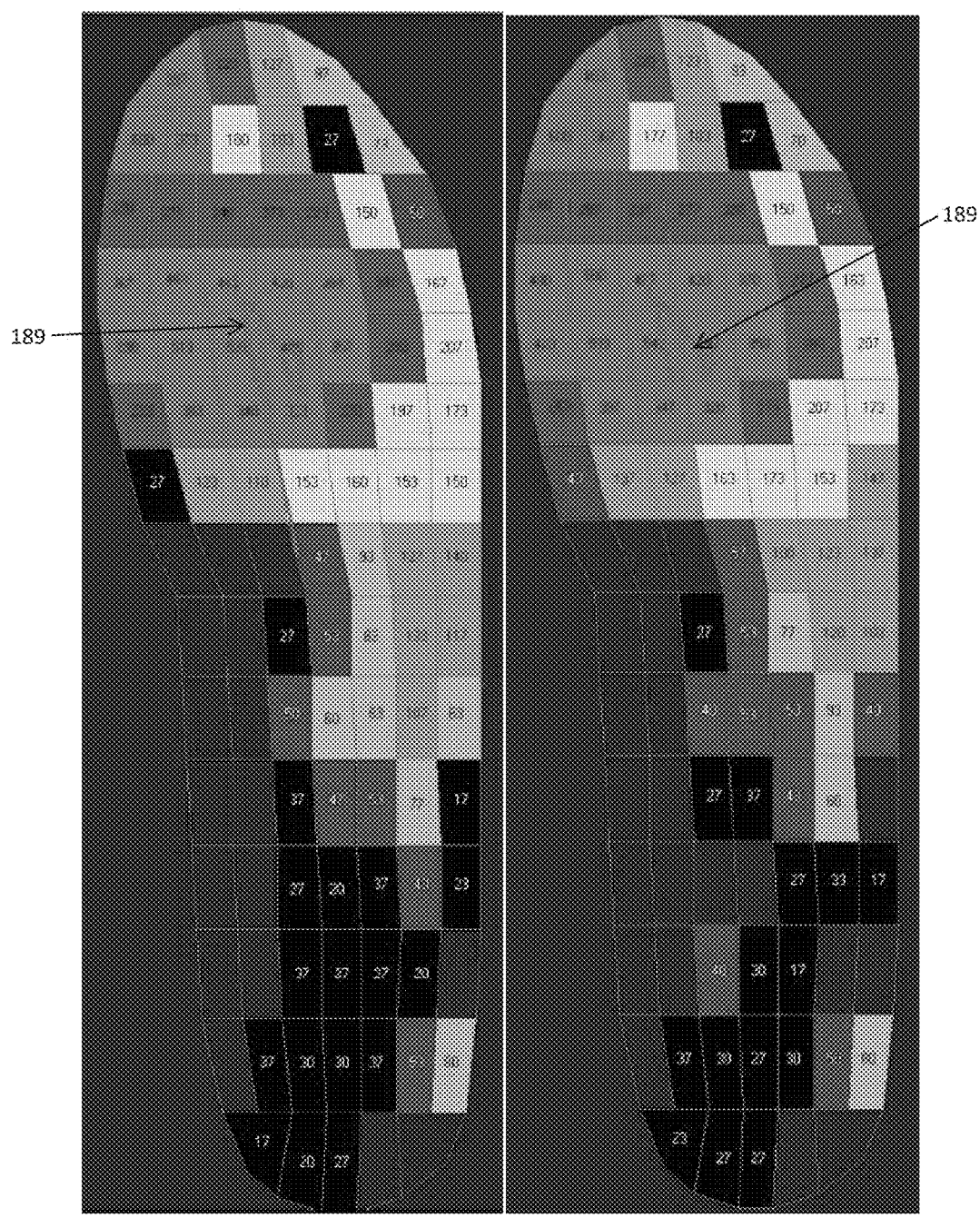
FIG. 10C is a schematic view of pressure data measurements and center of pressure data for another athlete undergoing a midfoot-striking style ground contact phase of a running motion, in accordance with one embodiment of the invention.
FIG. 10D is a schematic view of pressure data measurements and center of pressure data for another athlete undergoing a forefoot-striking style ground contact phase of a running motion, in accordance with one embodiment of the invention.

Exemplary raw pressure measurement data showing pressure data in kPa for a ninety-nine pressure sensor element insole for the four different athletes at the point of initial ground contact can be seen in FIGS. 10A through 10D, with FIG. 10A showing the heel-strike athlete data, FIGS. 10B and 10C showing the two midfoot strike athlete data sets, and FIG. 10D show the forefoot striking athlete data. Also shown for each data set is the center of pressure vector 189 for each athlete over the full course of a footstrike event.

Figure 11A:
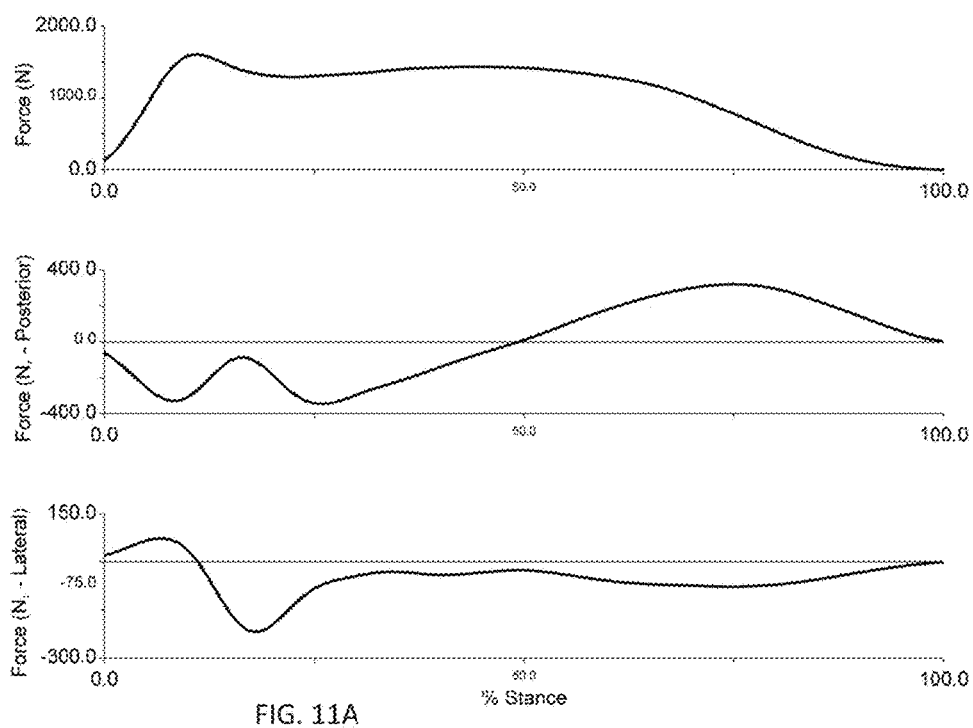
FIG. 11A is a graph of force measurements between an article of footwear and the ground during the ground contact phase of a running motion for a heel-striking running style, in accordance with one embodiment of the invention.
Figure 11B:
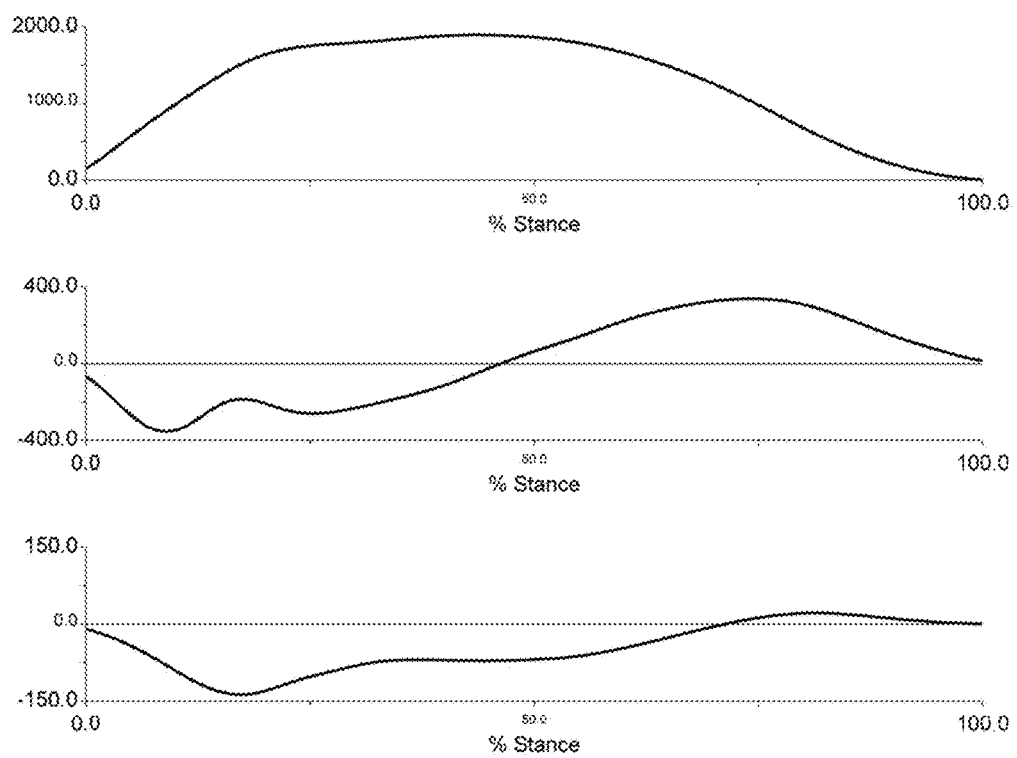
FIG. 11B is a graph of force measurements between an article of footwear and the ground during the ground contact phase of a running motion for a midfoot-striking running style, in accordance with one embodiment of the invention.

Exemplary force data taken from a force plate 130 over the full length of a footstrike event can be seen in FIGS. 11A and 11B, with FIG. 11A showing the force data for a heel-striking athlete and FIG. 11B showing force data for a midfoot striking athlete. In the graphs the vertical axis represents the measured force in a given axis (in Newtons (N)) while the horizontal axis represents the time (normalized such that '0.0' represents the initial ground contact and '100.0' represents the toe-off). For each figure, the top graph, with the vertical axis labeled "Force (N)", represents the vertical component of force applied to the foot 135 by the ground 145 perpendicular to the ground (i.e., along the axis 'Z' in the coordinate system 160), the middle graph, with the vertical axis labeled "Force (N-Posterior)", represents the horizontal component of force applied to the foot 135 by the ground 145 parallel with the direction of travel (i.e., along the axis 'X' in the coordinate system 160), and the lower graph, with the vertical axis labeled "Force (N-Lateral)", represents the horizontal component of force applied to the foot 135 by the ground 145 perpendicular to the direction of travel (i.e., axis 'Y' in the coordinate system 160). As can be seen, the force between the foot 135 and the ground 145 changes dramatically over the length of the footstrike event for each athlete and also differs considerably for a heel-strike type running motion and a midfoot-strike type running motion.

In one embodiment, a plurality of pressure sensors may be positioned on the ground rather than be embedded in or attached to a portion of the foot, with the sensors measuring the pressure applied by a foot as it makes contact with the sensor array located on the ground.

In various embodiments the experimental data may include other measurements in addition to, or instead of, the pressure and/or force data captured by the system of FIG. 2. Such measurement systems may include sensors for measuring elements such as, but not limited to, position, velocity, acceleration, rotational velocity, rotational acceleration, a change in shape of at least a portion of a foot, friction, mass distribution, energy distribution, stress, strain, temperature, distortion, moisture levels, and/or a time over which an event occurs. Such sensors can be used to measure events such as ground contact time, initial footstrike location, toe-off position, pronation/supination characteristics and/or a change in shape and/or position of at least a portion of the foot of the user during at least a portion of the ground contact phase of the gait cycle or other athletic motion, in addition to, or instead of, measuring force/pressure vectors associated with the interaction between the foot 135 and ground 140. An exemplary portable system adapted to identify parameters associated with an athlete's performance (such as, but not limited to, foot-strike location) during athletic activity is described in U.S. Patent Publication No. 2013-0041617 A1, the disclosure of which is incorporated herein by reference in its entirety.

Various sensor(s) for use with the methods and systems described herein may include, or consist essentially of, accelerometers, pressure sensors, force sensors, optical stress/strain sensors, temperature sensors, chemical sensors, global positioning systems, piezoelectric sensors, rotary position sensors, magnetometers, gyroscopic sensors, heart-rate sensors, and/or goniometers. Other sensors, such as, but not limited to, electrocardiograph sensors, electrodermograph sensors, electroencephalograph sensors, electromyography sensors, feedback thermometer sensors, photoplethysmograph sensors, and/or pneumograph sensors may also be utilized in various embodiments of the invention. Parameters relating to moisture in the body may, for example, be measured using any appropriate sensor for measuring skin conductance factors (e.g., galvanic skin response (GSR), electrodermal response (EDR), psychogalvanic reflex (PGR), skin conductance response (SCR) or skin conductance level (SCL) sensors).

For example, one embodiment of the invention may include one or more shear stress sensors on the sole of the shoe, with the distributed shear stress measurements providing directional data representative of the direction of interaction between the foot 135 and the ground 140. Stress and/or strain measurements on the sole on a shoe can also be used to determine flexing of the shoe and foot during a foot-strike event. This data may be used in addition to, or instead of, pressure and/or force data to determine the magnitude and direction of the interactions between the foot 135 and ground 140 during a footstrike event.

The above list of measurement options is not limiting, and in various embodiments of the invention any appropriate sensor, or combination of sensors, may be utilized to capture data representative of the performance of an athlete 125 in carrying out an athletic activity, with this data being used as input parameters for analyzing the athlete's particular performance traits to allow for the designing of customized footwear elements. More particularly, each of the data sets and performance characteristics identified through the above measurement options can change dramatically depending upon the specific athletic technique and physical characteristics of an athlete, and the measurement of any of these elements may therefore be extremely helpful in identifying performance metrics that can be used to customize a shoe for a particular athlete.

The data gathered for any of the experimental measurements described herein can be sampled at any appropriate rate, but generally at a rate sufficient to capture the progression of the measurements throughout a ground contact portion of a gait cycle in sufficient detail to allow for customization to the level of accuracy required by the athlete. In various examples, sample rates of about 10 Hz, 20 Hz, 50 Hz, 100 Hz, or 200 Hz may be utilized, although different rates, and larger or smaller rates, may be used as appropriate. In one embodiment the gathered data may be averaged over any appropriate number of foot-strike events to provide an averaged representation of the athlete's performance characteristics. In one embodiment the raw data may be filtered using any appropriate filtering technique (e.g., high-pass, low-pass, and/or Butterworth filtering) to filter out non-essential information and ensure that only the appropriate data is analyzed in the customization algorithms. For example, in one embodiment high-pass type filtering may be applied to the results to filter out data below a set magnitude and only allow higher magnitude data to be processed in the customized design algorithms. In addition, various forms of data smoothing may be applied to the data to provide further filtering of the results (for example where an arrangement of traction elements needs to be structured to control differences in size, shape, orientation, etc. between adjacent traction elements).

In one embodiment the input parameters for the customized design process may include one or more physical characteristics of a foot 135 of the athlete 125 in addition to, or instead of, the experimental data described herein. Such physical characteristics may include, but are not limited to, physiological structural characteristics of the foot and/or body such as at least one of a shape, a size, a wear pattern, an injury profile, a bone structure, a ligament structure, a sweat gland distribution, a moisture level, a circulation arrangement or metric, a muscle activity, a friction metric, a blood pressure, a heart rate, a volume change, a hydration level, a perspiration level, a ligament structure, a toe shape and/or distribution (e.g., length and relative position of toes, relative location of metatarsal heads, etc.), an arch shape, and/or a heel shape (e.g., calcaneus shape). Such physical characteristics may, for example, be measured manually, scanned and recorded through an automated 2D or 3D scanning device, or determined through 3D processing of photographic images of the foot 135.

An exemplary method for analyzing the input parameters, and more specifically input parameters such as normal pressure distribution data and three-component force data, to produce performance metrics to be used in the customization of footwear can be seen in FIGS. 12A through 16A. In this embodiment, the pressure data and force data can be processed and multiplied together to create vectors (having both a magnitude and direction) representative of the interaction between the ground 145 and the foot 135, over the full sole area of the foot, with the resulting vectors being used to identify locations and distributions of structural characteristics of the footwear that best address the requirements of the individual athlete.

Figure 12A:
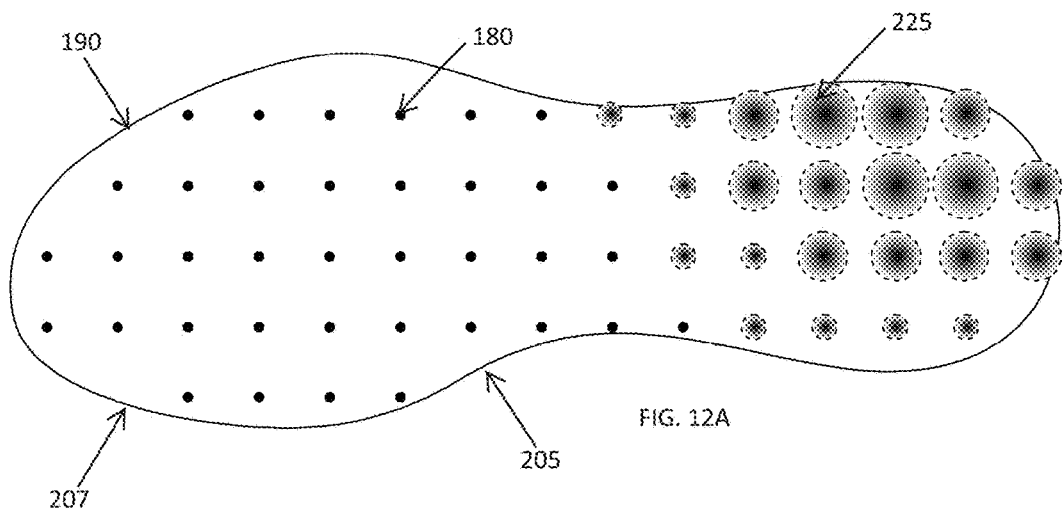
FIG. 12A is a schematic representation of pressure measurements on a plurality of pressure sensors in an insole of an article of footwear during an initial heel-striking ground contact phase of a running motion, in accordance with one embodiment of the invention.
Figure 12B:
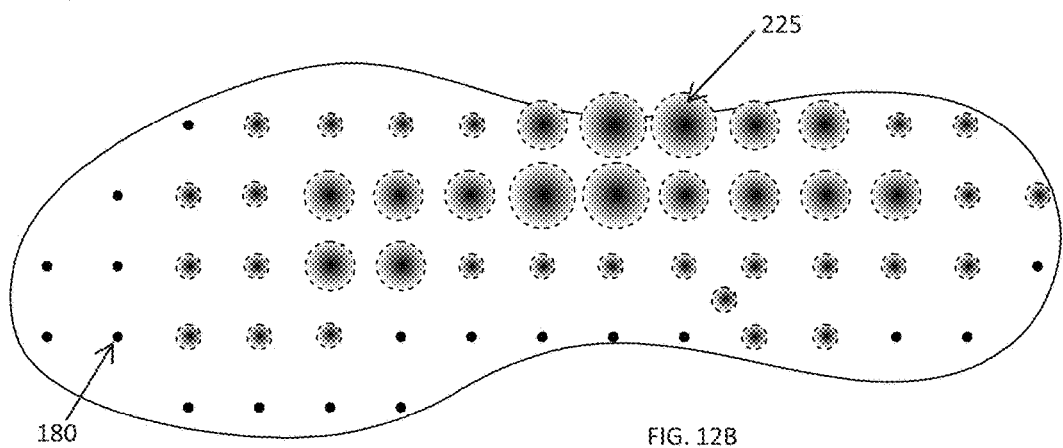
FIG. 12B is a schematic representation of pressure measurements in the insole of FIG. 12A during an intermediate ground contact phase of a running motion.
Figure 12C:
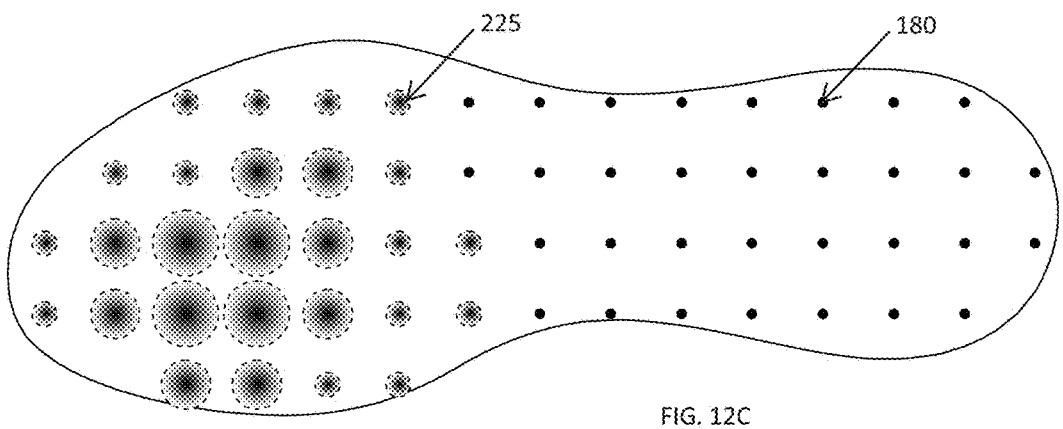
FIG. 12C is a schematic representation of pressure measurements in the insole of FIG. 12A during a toe-off phase of a running motion.

FIGS. 12A-12C show schematic representations of pressure data measured by pressure sensor elements 180 using the insole 187 of FIG. 5B, with FIG. 12A showing pressure measurements at or around initial ground contact for a heel-striking athlete, FIG. 12B showing pressure measurements for that athlete at approximately a midpoint of the ground contact phase, and FIG. 12C showing pressure measurements for that athlete just prior to toe-off. The magnitude of the pressure normal to the surface of the insole 187 is represented by the size of the shaded circles 225 placed over each sensor element 180, with a larger pressure indicated by a larger circle and smaller pressures represented by a smaller circle. As can be seen, the measurements show a movement of the pressure from near the heel 190 of the insole (at initial heel-strike), through the midfoot region 205, and towards the forefoot region 207 (at toe-off) during a full ground contact event. As discussed above, the specific variation in pressure magnitude and distribution can vary greatly from athlete to athlete. While only three time steps within a footstrike event are shown in FIGS. 12A though 12C any appropriate number of time steps may be used in a full analysis of the input parameters depending upon the sample rates of the measurement devices utilized and the requirements of the processing algorithms being utilized.

Figure 13A:
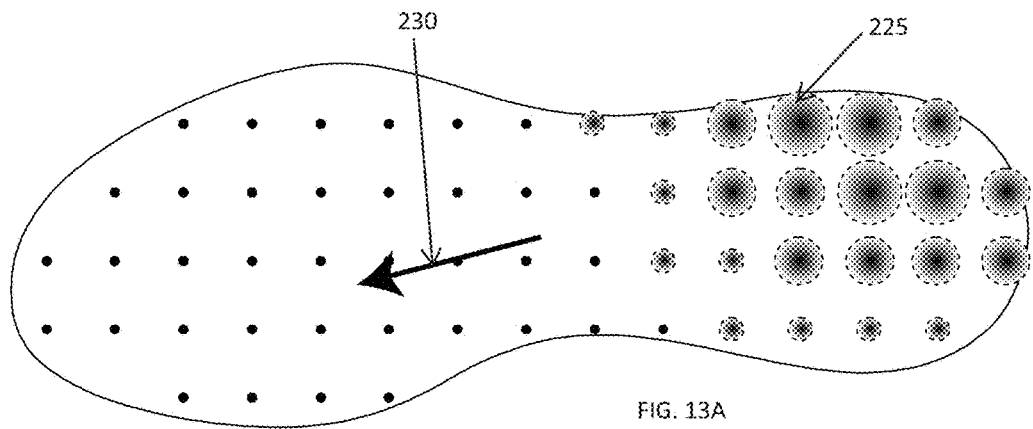
FIG. 13A is a schematic view of both force and localized pressure data during an initial heel-striking ground contact phase of a running motion, in accordance with one embodiment of the invention.
Figure 13B:
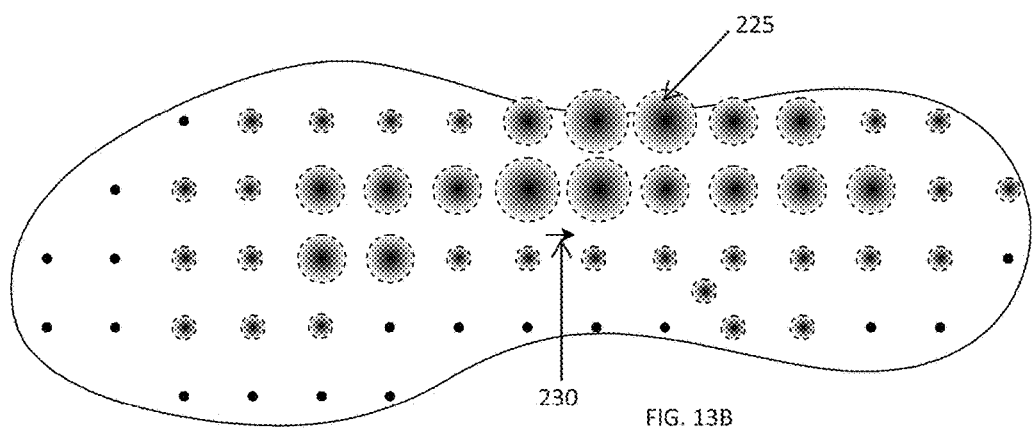
FIG. 13B is a schematic view of both force and localized pressure data for the shoe of FIG. 13A during a ground contact phase of a running motion.
Figure 13C:
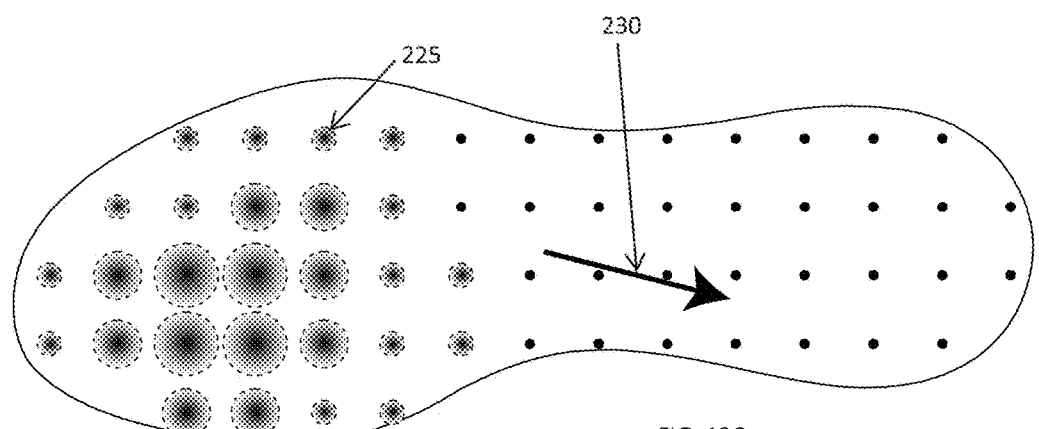
FIG. 13C is a schematic view of both force and localized pressure data for the shoe of FIG. 13A during a toe-off phase of a running motion.

FIGS. 13A through 13C show the same pressure data as in FIGS. 12A-12C but also add in the horizontal component of force 230 exerted by the foot 135 on the ground 145 measured by the force plate 140 at that time (with the horizontal component of force represented by a vector 230 showing the direction of the horizontal component of force (with the relative magnitude of the force represented by the length of the vector). As can be seen, for the heel-strike type ground contact represented, the foot 135 exerts a relatively large force in substantially the direction of travel of the foot upon initial footstrike, with relatively little horizontal force applied during the middle of the footstrike event, and with a relatively large force substantially backwards in the opposite direction to the direction of travel at toe-off.

The pressure and force data can then be processed to determine appropriate performance metrics to be used in customization. In this embodiment, the pressure data at each point is multiplied by the force vector at that time to produce a vector representative of the foot/ground interaction at each point on the sole of the foot at each time step within the footstrike event to obtain Performance Metric Vectors (PMV) according to the following formulation:

$$PMV_{at\ each\ time\ step} = \text{Function of } \{C_1 \times \text{Pressure} \times \text{Force}\}_{at\ each\ time\ step}$$

Where $C_1$ is an appropriate multiplication/adjustment factor.

Figure 14A:
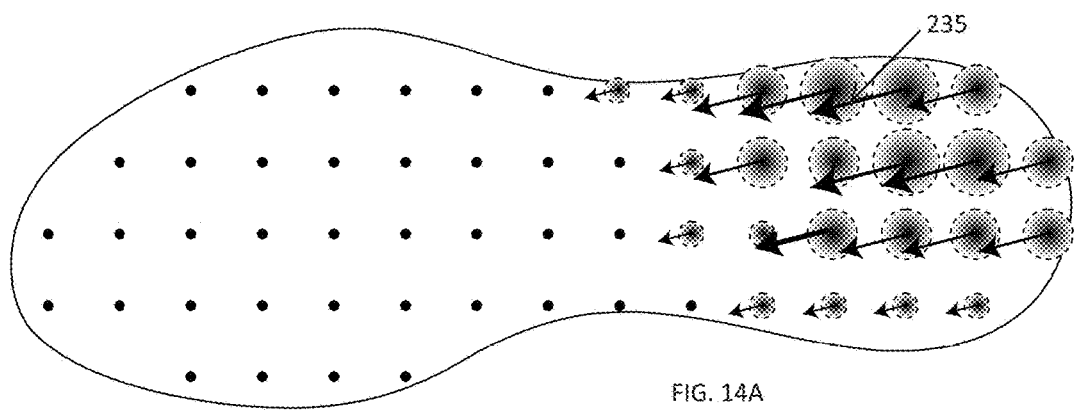
FIG. 14A is a schematic view of pressure and distributed performance metric data during an initial heel-striking ground contact phase of a running motion, in accordance with one embodiment of the invention.
Figure 14B:
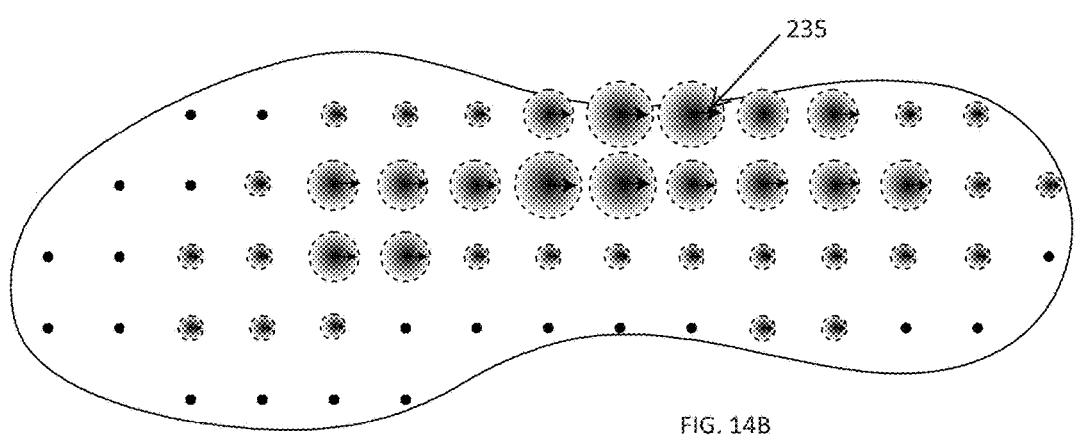
FIG. 14B is a schematic view of both pressure and distributed performance metric data for the shoe of FIG. 14A during a ground contact phase of a running motion.
Figure 14C:
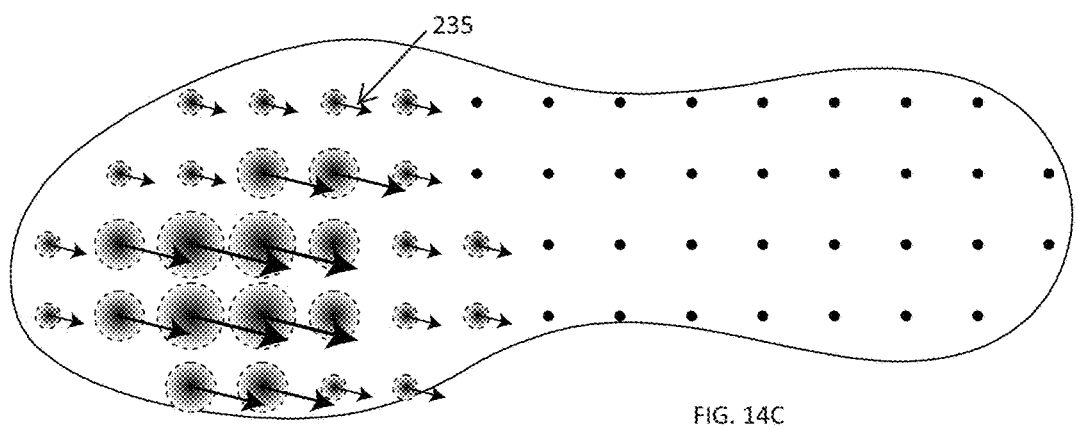
FIG. 14C is a schematic view of both pressure and distributed performance metric data for the shoe of FIG. 14A during a toe-off phase of a running motion.
Figure 15A:
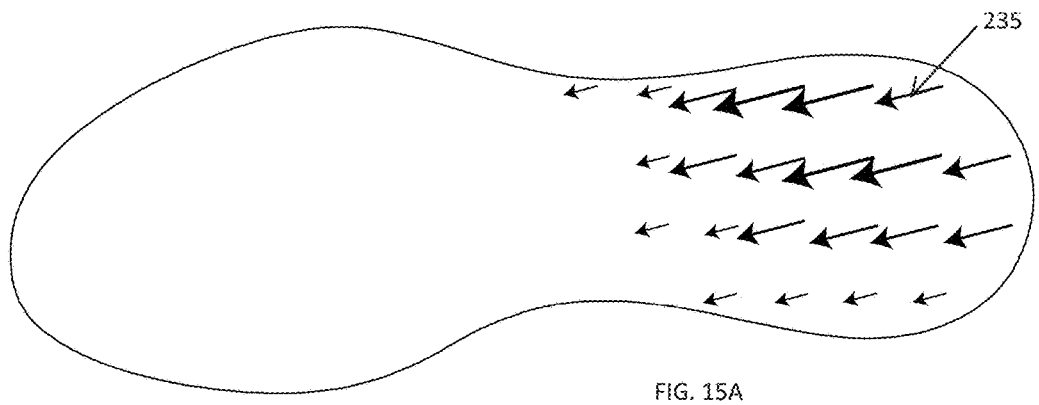
FIG. 15A is a schematic view of the distributed performance metric data of FIG. 14A.
Figure 15B:
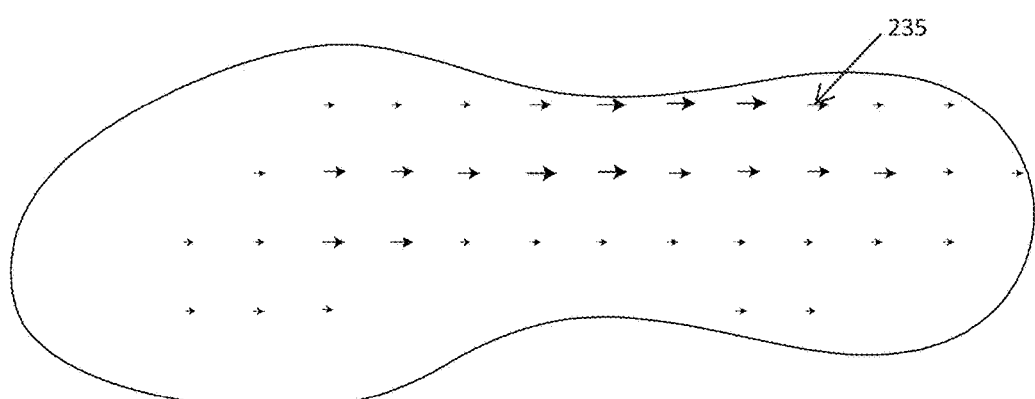
FIG. 15B is a schematic view of the distributed performance metric data of FIG. 14B.
Figure 15C:
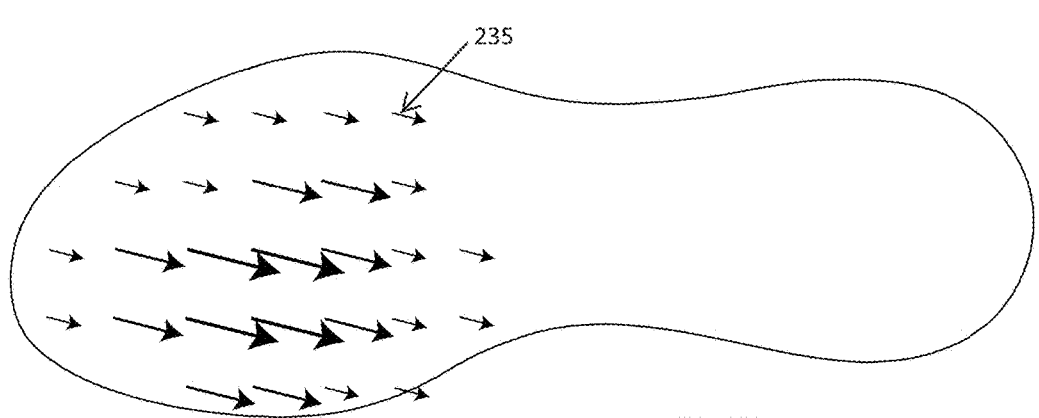
FIG. 15C is a schematic view of the distributed performance metric data of FIG. 14C.

FIGS. 14A through 14C show the resulting performance metric vectors 235 calculated using the data of FIGS. 13A through 13C, with the pressure data at each point indicated by the circles 225, with the length of the vectors 235 representative of the magnitude of the vector. FIGS. 15A through 15C shows the performance metric vectors 235 at the three shown time steps with all other information removed from the figures. Once the performance metric vectors 235 have been calculated for each time step, the final performance metrics at each location over the sole can be determined by, in one embodiment, summing the individual Performance Metric Vectors at each location for each time step according to the following function:

$$PMV_{aggregate} = \text{Sum of } [C_2 \times PMV\{t_1, t_2, t_3, \ldots t_N\}]$$

Where $C_2$ is an appropriate multiplication/adjustment factor.

Figure 16A:
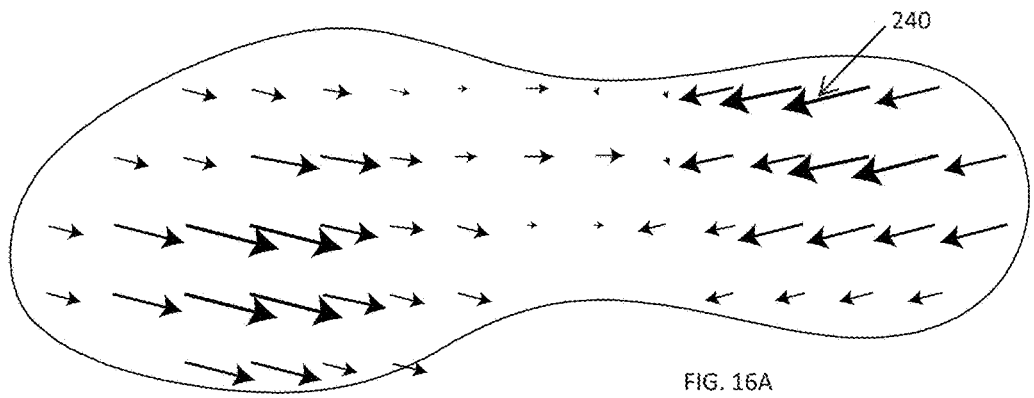
FIG. 16A is a schematic view of the combined distributed performance metric data of FIGS. 14A to 14C, in accordance with one embodiment of the invention.

The resulting distribution of performance metric vectors (PMV) can be seen in FIG. 16A, with each vector 240 representative of the sum total of the performance metric vectors at each time step at that location on the sole. These vectors 240 provide an indication of the magnitude and direction of the horizontal component of the interaction between ground 145 and foot 135 over the course of the ground contact event.

In various embodiments correction factors $C_1$ and $C_2$ can be used to weight and/or adjust the results to ensure that the resulting performance metric vectors are representative of the performance characteristics of importance in the analysis. For example, correction factors may be used to ensure that the results at each location focus on the magnitude and direction of the vectors during peak loading of the sole at that location while filtering out magnitude and direction results during low loading time periods of the ground-strike event. In an alternative embodiment no correction factor is required.

Once the performance metric vectors have been generated, this information can be utilized to determine a structural characteristic of at least a portion of a sole of an article of footwear for the user based on the performance metric. For example, for embodiments where the footwear is to be customized to improve traction during a ground contact event, the performance metric vectors can be used to orient and distribute traction elements over the surface of an outsole or ground contacting midsole portion of a shoe (or portions thereof), with the size, shape, and/or distribution of the traction elements dependent upon the magnitude of the performance metric vectors in a specific region of the outsole. Exemplary outsoles for an article of footwear including customized traction elements 245 based on the performance metric vectors 240 of FIG. 16A can be seen in FIGS. 16B and 16C.

Figure 16B:
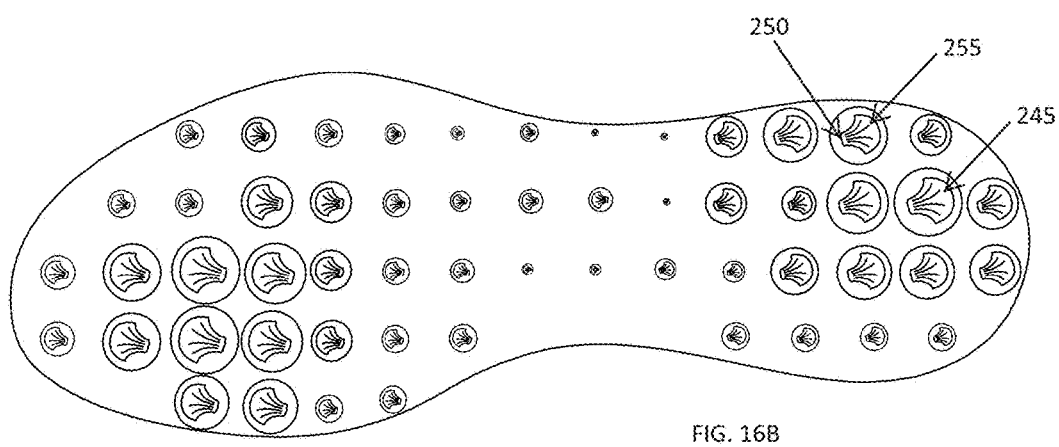
FIG. 16B is a schematic plan view of an outsole for an article of footwear having structural characteristics based on the performance metric data of FIG. 16A.
Figure 16C:
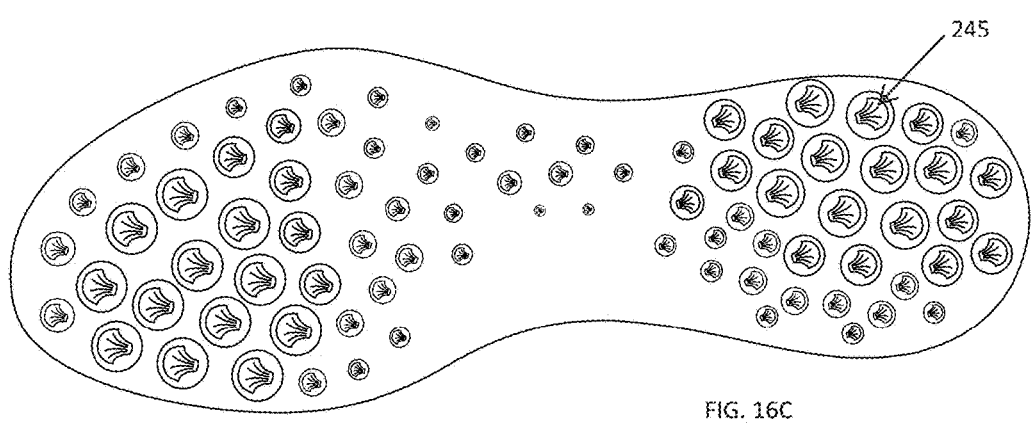
FIG. 16C is a schematic plan view of another outsole for an article of footwear having structural characteristics based on the performance metric data of FIG. 16A.

In FIG. 16B, the traction elements 245 are arranged in a regular pattern corresponding to the locations of the pressure sensor elements 180 utilized during the measurement of the input parameters. In an alternative embodiment, such as that shown in FIG. 16C, the traction elements 245 can be located in any regular or non-regular pattern independent of the specific locations of the pressure sensor elements 180 utilized during the measurement of the input parameters.

Figure 17A:
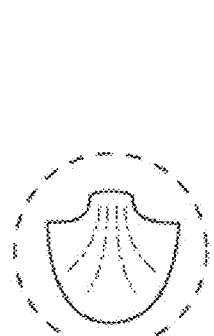
FIGS. 17A-17B are plan and side views of a traction element for an outsole element of an article of footwear, in accordance with one embodiment of the invention.
Figure 17B:
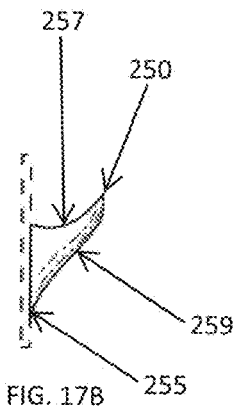
Figure 17C:
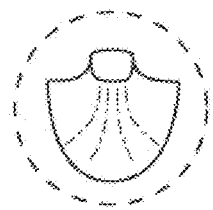
FIGS. 17C-17D are plan and side views of another traction element for an outsole element of an article of footwear, in accordance with one embodiment of the invention.
Figure 17D:
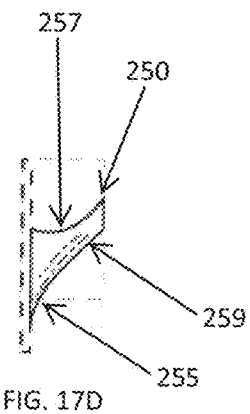
Figure 17E:
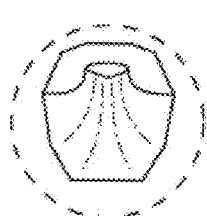
FIGS. 17E-17F are plan and side views of another traction element for an outsole element of an article of footwear, in accordance with one embodiment of the invention.
Figure 17F:
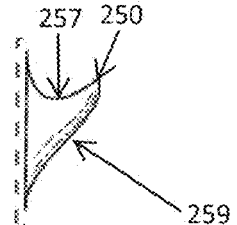
Figure 17G:
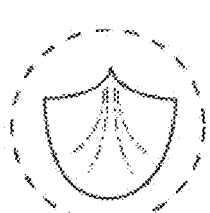
FIGS. 17G-17H are plan and side views of another traction element for an outsole element of an article of footwear, in accordance with one embodiment of the invention.
Figure 17H:
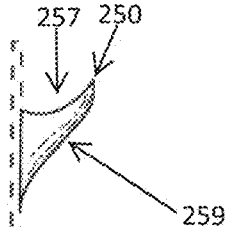
Figure 17I:
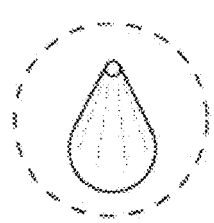
FIGS. 17I-17J are plan and side views of another traction element for an outsole element of an article of footwear, in accordance with one embodiment of the invention.
Figure 17J:
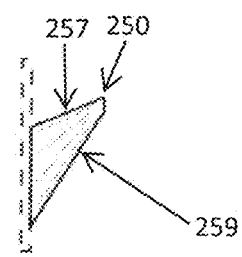
Figure 17K:
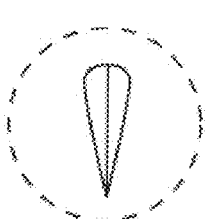
FIGS. 17K-17L are plan and side views of another traction element for an outsole element of an article of footwear, in accordance with one embodiment of the invention.
Figure 17L:
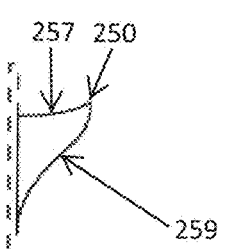
Figure 17M:
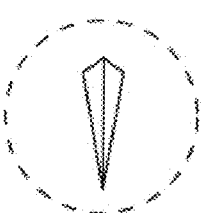
FIGS. 17M-17N are plan and side views of another traction element for an outsole element of an article of footwear, in accordance with one embodiment of the invention.
Figure 17N:
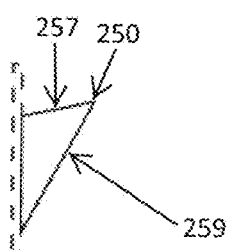
Figure 17O:
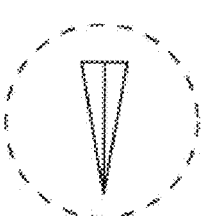
FIGS. 17O-17P are plan and side views of another traction element for an outsole element of an article of footwear, in accordance with one embodiment of the invention.
Figure 17P:
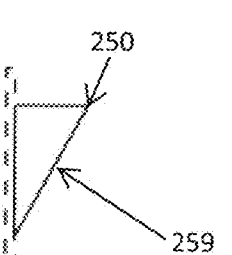
Figure 18:
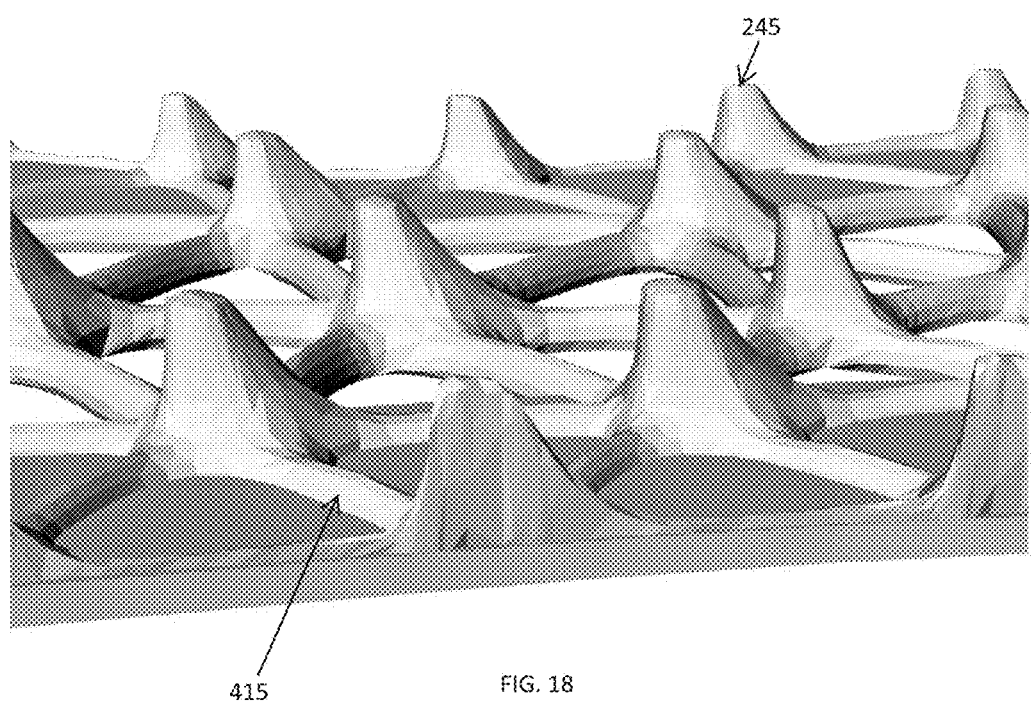
FIG. 18 is a perspective view of an outsole element for an article of footwear having a plurality of traction elements thereon, in accordance with one embodiment of the invention.
Figure 19A:
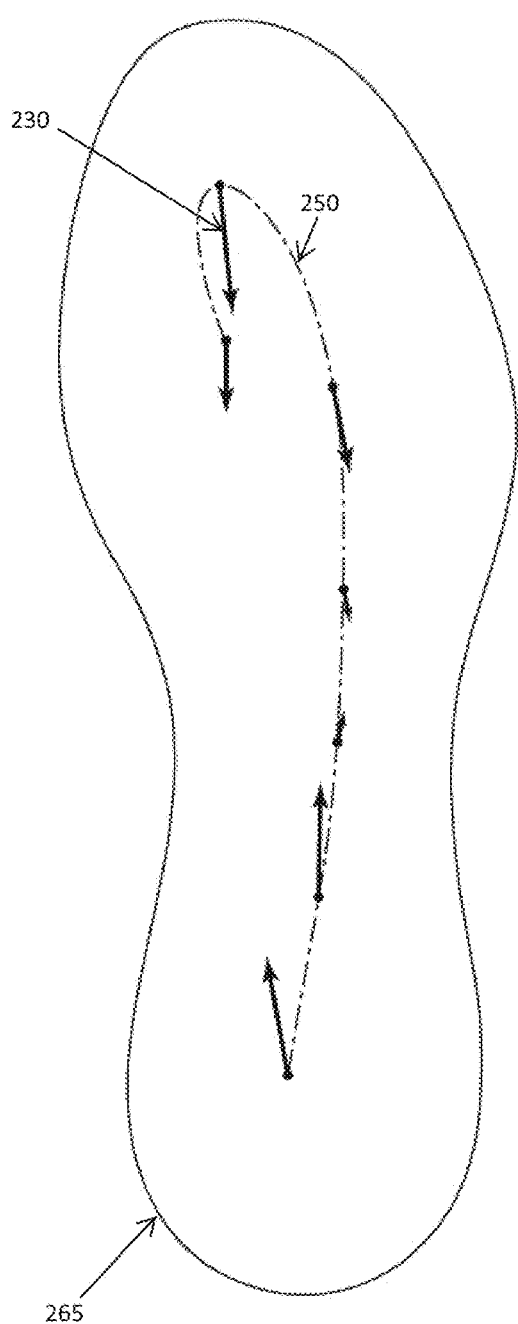
FIG. 19A is a schematic representation of a center of pressure vector for a foot of an athlete undergoing a heel-striking style ground contact phase of a running motion, in accordance with one embodiment of the invention.
Figure 19B:
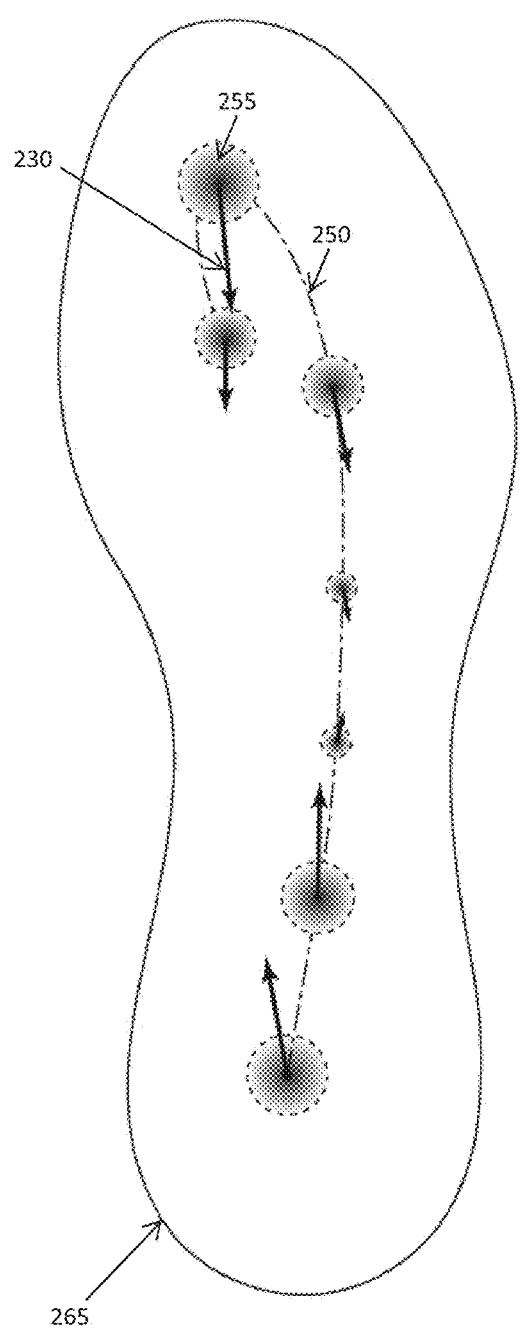
FIG. 19B is a schematic plan view of the center of pressure vector of FIG. 16A with exemplary data representative of the pressure at various locations along the center of pressure vector.
Figure 20A:
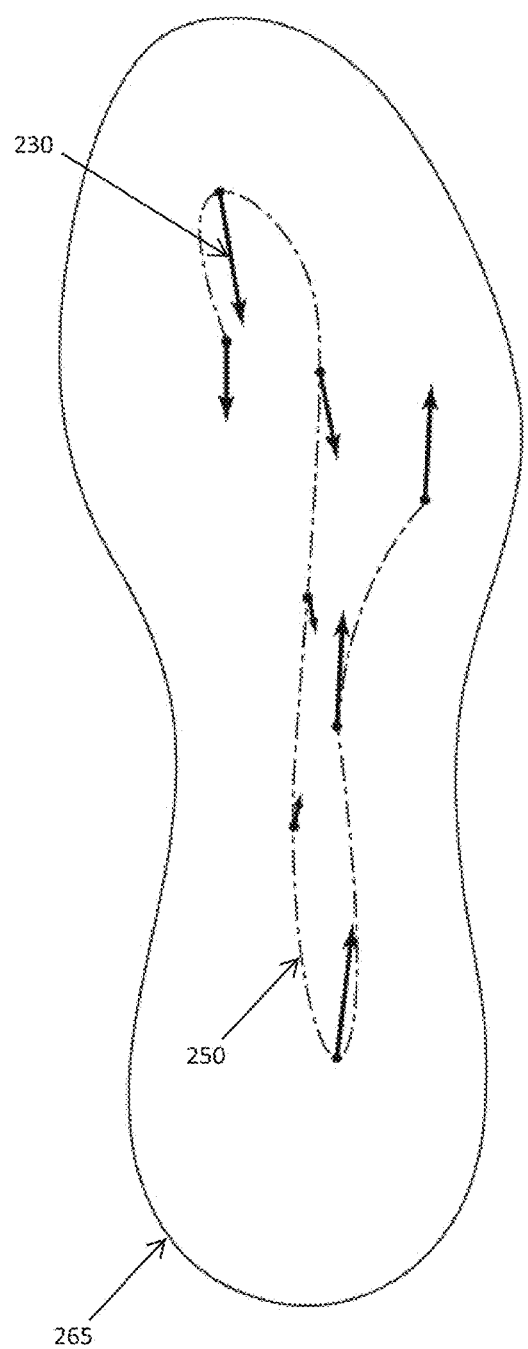
FIG. 20A is a schematic representation of a center of pressure vector for a foot of an athlete undergoing a midfoot-striking style ground contact phase of a running motion, in accordance with one embodiment of the invention.
Figure 20B:
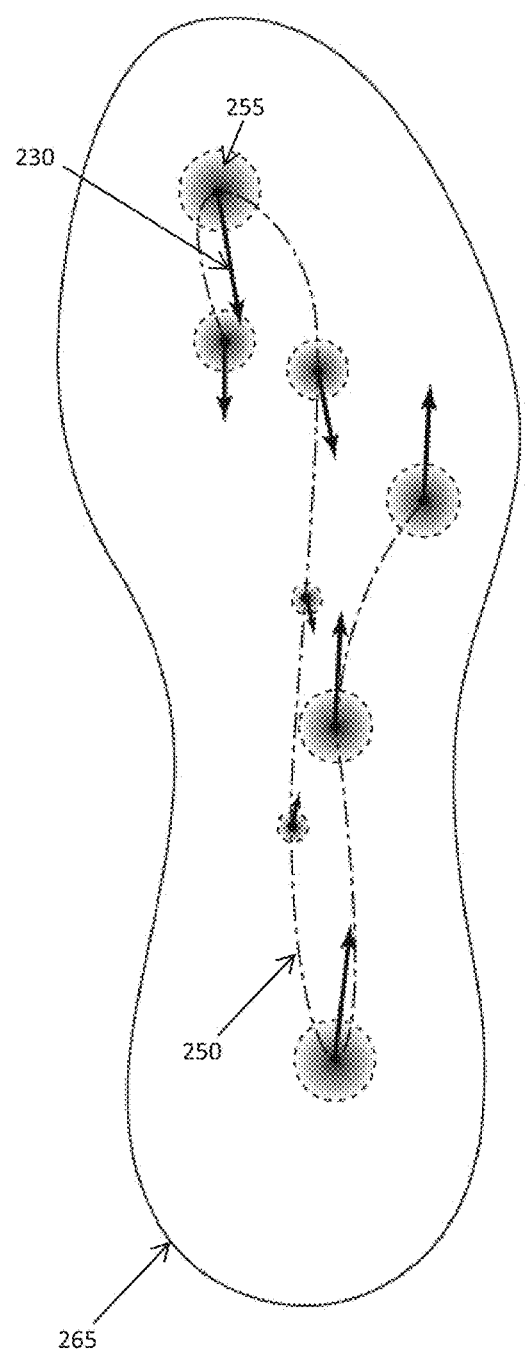
FIG. 20B is a schematic plan view of the center of pressure vector of FIG. 18A with exemplary data representative of the pressure at various locations along the center of pressure vector.

The traction elements 245 may be asymmetrically constructed such that they include a leading edge 250 and a trailing edge 255, with the traction provided by the traction elements 245 being optimized when oriented such that the leading edge 250 is perpendicular to the direction of the performance metric vectors, hereby providing customized and optimized traction in the direction most important to the performance of the specific athlete. Various exemplary directionally oriented traction elements 245 are shown in FIGS. 17A through 18, with each traction element 245 having a preferred orientation with a leading edge 250 (either an elongate edge or a point) oriented in the direction of the performance metric vectors for a specific athlete.

Various embodiments of the traction elements 245 can include an undercut 257 which is designed to produce a sharper leading edge 250, thereby improving traction in the direction facing the leading edge 250. The size and shape of the undercut 257 can also affect and control the flexibility of the traction elements 245 during ground interaction, with a larger undercut 257 producing a thinner, and therefore more flexible, traction element 245 (for the same configuration of sloped back portion 259). Certain embodiments of the traction elements 245 can include a sloped back portion 259, which can potentially reduce the traction produced by the traction element 245 in the direction facing the sloped back portion 259. As a result, traction can be customized to produce greater traction in certain directions (e.g., the directions associated with the ground interaction at various locations on the foot throughout a foot-strike event, while reducing traction, and therefore reducing friction, in directions in which high traction is not required and in fact may be detrimental to performance. Careful shaping of the traction elements 245 can also allow for minimization of the material used (and therefore the weight of material required) without compromising the performance of the traction elements 245.

In one embodiment the traction elements 245 can be customized such that the size of the traction elements 245 varies depending upon the magnitude and/or direction of the performance metric vector in that region. Alternatively, or in addition, the number of traction elements 245 can vary depending upon the magnitude and/or direction of performance metric vectors in that region with, for example, a larger number of traction elements 245 clustered in regions having high magnitudes of performance metric vectors. In various embodiments any appropriate distribution of traction elements, tread patterns, and/or spike patterns, and traction element/tread/spike orientation, shape, and/or configuration, can be utilized to customize the outsole, depending upon the specific performance characteristics required of the athletic activity at issue and/or the athletes aesthetic and/or performance preferences.

Various embodiments of the invention may include different and/or additional methods of processing the input parameter information to obtain performance metric information for use in customizing a shoe. For example, rather than providing separate performance metric vectors for each measured location on the sole of the foot, the information can be averaged over a number of predetermined zones (e.g., a heel zone, a midfoot zone, and a forefoot zone) with different performance metric vectors, and therefore different sizes and orientations of traction elements, for each different zone, and with the same orientation and size of traction element being distributed throughout an individual zone. This may be achieved, for example, by using the raw pressure distribution data at each time step to estimate a center of pressure for that time step, and then generating a vector using the center of pressure data for each time step to provide the center of pressure vector for a footstrike for an individual athlete. As with the distributed pressure data, the center of pressure data can differ greatly for different athletes and can therefore provide valuable differentiating information to allow for the customization of the footwear for a specific athlete.

Figure 21A:
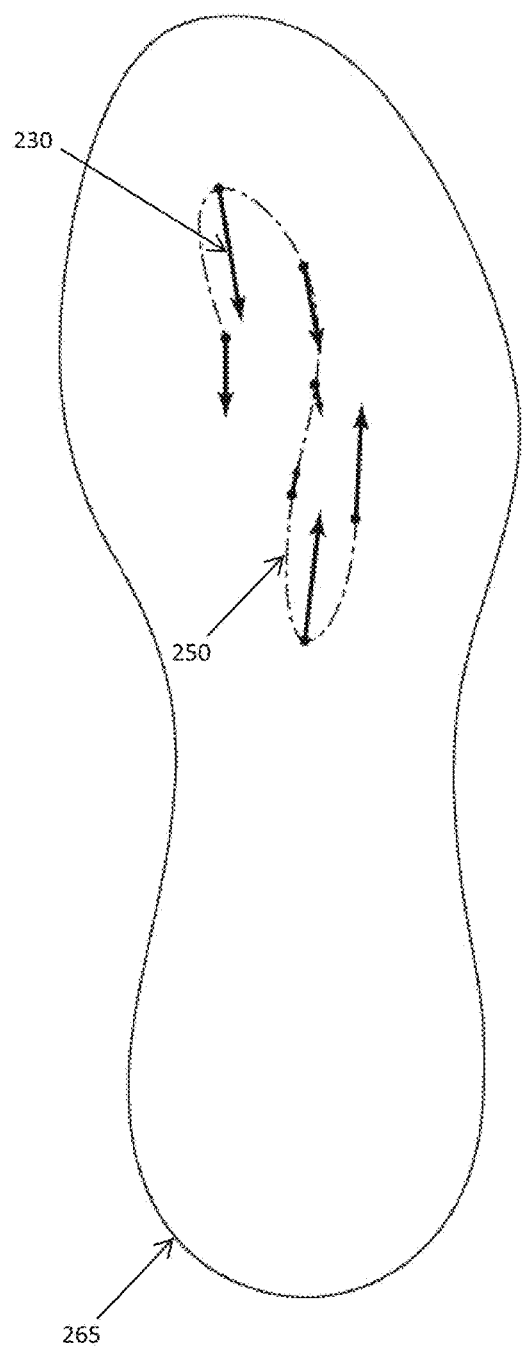
FIG. 21A is a schematic representation of a center of pressure vector for a foot of an athlete undergoing a forefoot-striking style ground contact phase of a running motion, in accordance with one embodiment of the invention.
Figure 21B:
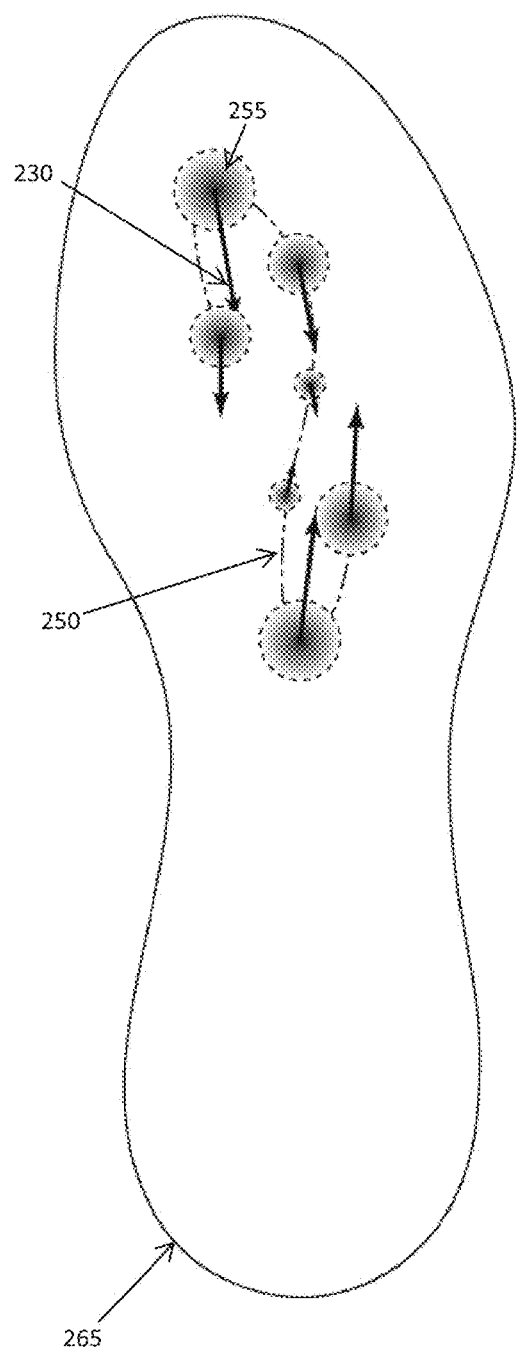
FIG. 21B is a schematic plan view of the center of pressure vector of FIG. 19A with exemplary data representative of the pressure at various locations along the center of pressure vector.
Figure 22A:
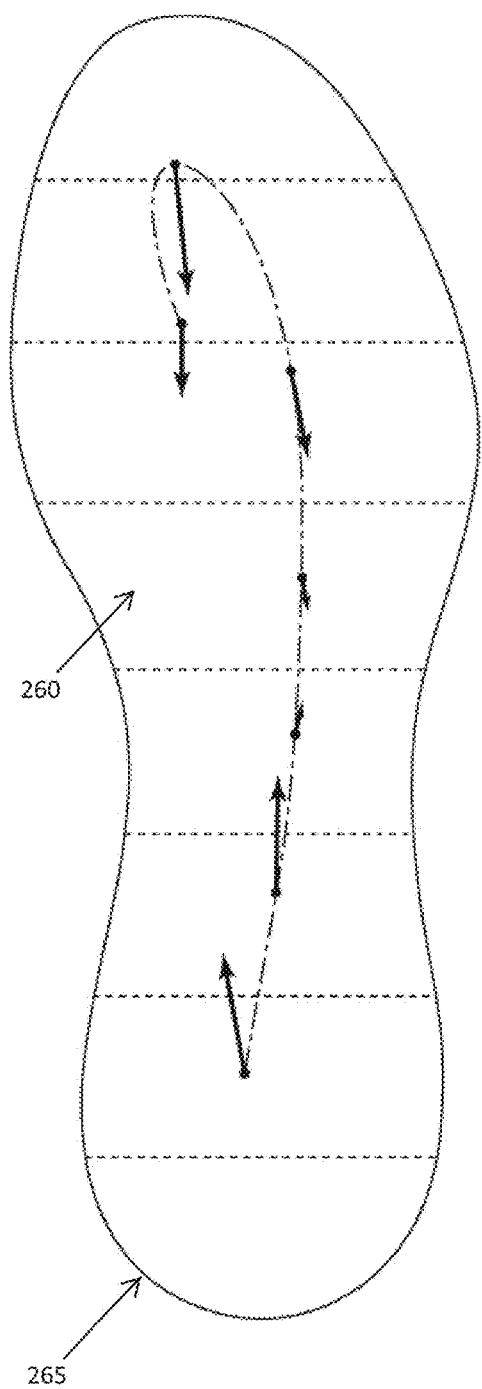
FIG. 22A is a schematic plan view of a distribution of grid sections for the foot of FIG. 17A, in accordance with one embodiment of the invention.
Figure 22B:
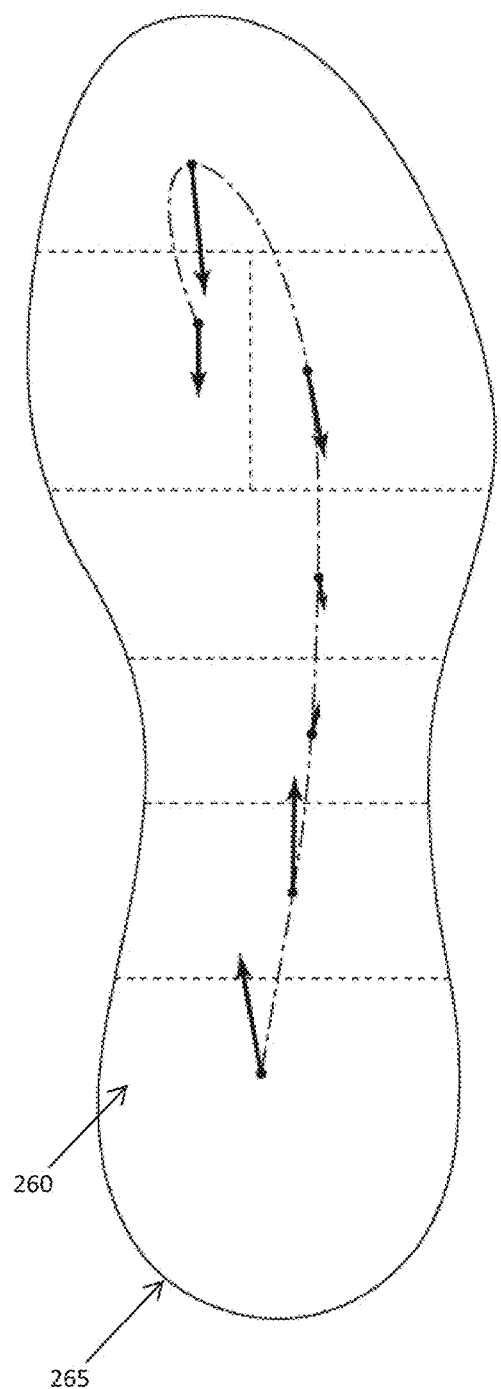
FIG. 22B is a schematic plan view of another distribution of grid sections for the foot of FIG. 17A, in accordance with one embodiment of the invention.

Exemplary schematic center of pressure vectors 250 for various footstrike types can be seen in FIGS. 19A through 21B, with a center of pressure vector 250, along with representative force vectors 230 and summed pressure measurements 255 shown for a heel striker (FIGS. 19A and 19B), a midfoot striker (FIGS. 20A and 20B), and forefoot striker (FIGS. 21A and 21B). Exemplary zones 260 into which the performance metric vectors for each location along the center of pressure vector 250 are utilized in the customization process can be seen in FIGS. 22A and 22B, with FIG. 22A showing a sole 265 divided into eight separate zones 260 divided equally along the length of the sole 265, and FIG. 22B showing seven zones 260 of differing lengths and shapes covering the sole 265. In various embodiments any distribution of zones 260 may be utilized depending upon the level of customization required.

In one embodiment, the performance metric information (e.g., performance metric vectors) may be further analyzed to determine the specifics of the distribution of traction elements within the outsole. Exemplary geometrical and mathematical modeling techniques that may be utilized to analyze the input parameters and/or performance metric information to design the customized footwear elements may include, but are not limited to, circle packing, Delaunay triangulation, and/or Voronoi decomposition (or Voronoi tessellation/Voronoi diagrams).

Figures 23A, 23B, 23C:
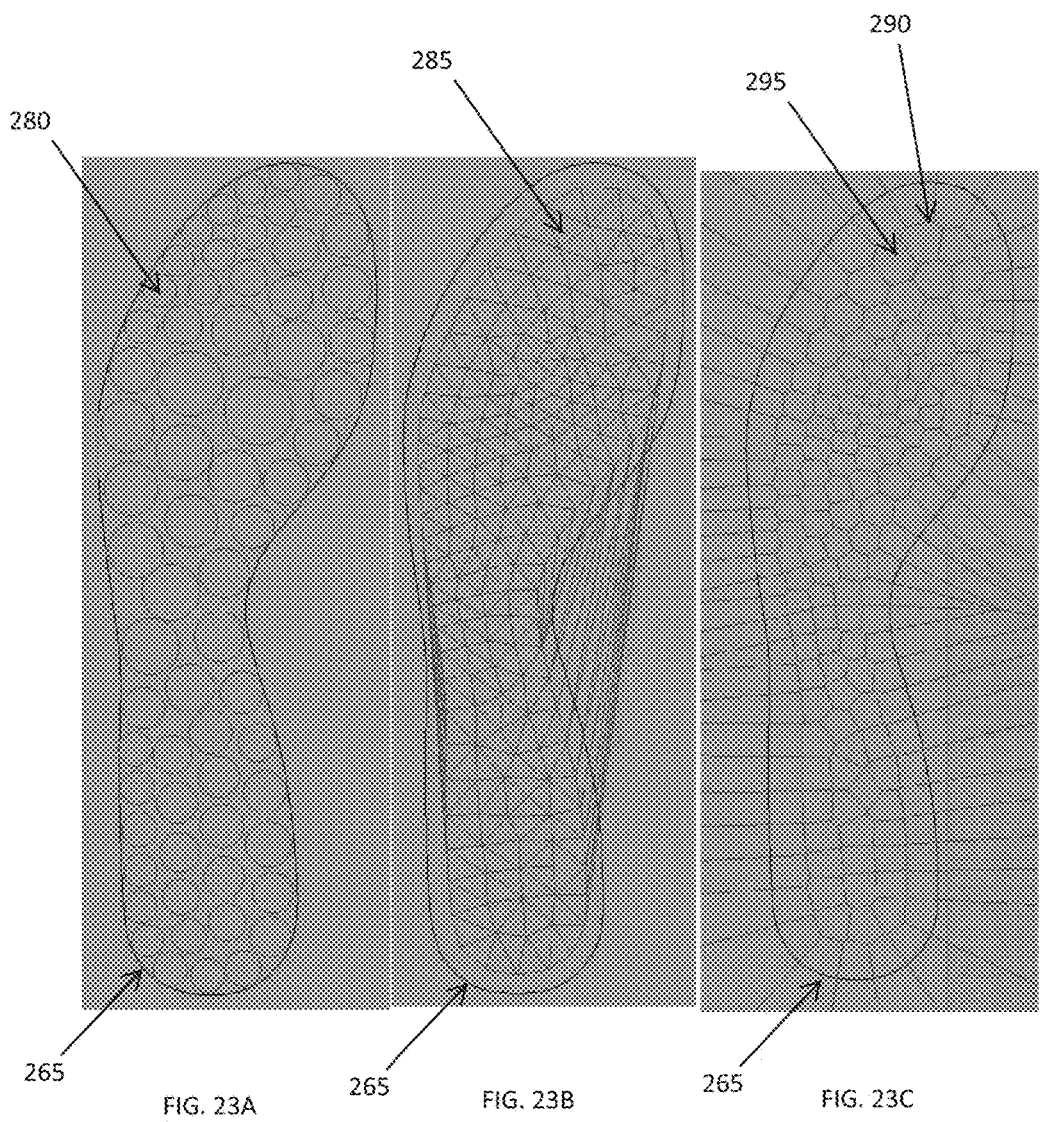
FIG. 23A is a schematic representation of a method of creating a structural characteristic for an article of footwear based on performance metric information using a circle packing analytical technique, in accordance with one embodiment of the invention.
FIG. 23B is a schematic representation of a method of creating a structural characteristic for an article of footwear based on performance metric information using a Delaunay triangulation analytical technique, in accordance with one embodiment of the invention.
FIG. 23C is a schematic representation of a method of creating a structural characteristic for an article of footwear based on performance metric information using a Voronoi diagram analytical technique, in accordance with one embodiment of the invention.

An exemplary analytical method, as shown in FIG. 23A, includes the use of circle packing, whereby an arrangement of circles 280 of equal or varying sizes on a given surface (e.g., a shoe sole 265) can be optimized such that no overlapping occurs and so that all circles 280 touch another. The number of circles, the size of the circles (either uniform or of differing sizes), and the localized distribution of the circles can be controlled depending upon the specific requirements of the system. In one embodiment performance metric information (e.g., the magnitude of the performance metric vectors at various locations throughout the sole) can be used as an input to the circle packing algorithm, with the magnitude of the performance metric vectors in a given region controlling the size and/or number of circles 280 in that region. Using control inputs such as, but not limited to, the number of circles 280 to be distributed throughout the sole 265 and/or the maximum and minimum size of the circles to be distributed throughout the sole 265 as additional inputs allows the circle packing algorithm to process the performance metric information to generate an optimized distribution of traction elements 245 based on the specific inputs provided with, for example, a traction element 245 positioned at the center of each circle 280.

Another analytical method, as shown in FIG. 23B, includes the use of Delaunay triangulation to distribute the traction elements 245 at optimal positions within the sole 265 through optimized triangulation of the input parameter data and/or performance metric data. In this analytical method, the raw input parameter data and/or performance metric data can be utilized to create a plurality of triangles 285 optimally distributed through the sole 265, with traction elements thereafter located at the central apex of each triangle 285. Another, related, analytical method includes the use of a Voronoi tessellation, which is a method of dividing space into a number of regions where a plurality of points (otherwise known as seeds, sites, or generators) is specified beforehand and where the algorithm results in the utilization of the seed point to generate a plurality of Voronoi vertices or nodes 290, which represent points equidistant to three (or more) sites. Utilization of input parameter data and/or performance metric data as control elements for the Voronoi tessellation algorithms allows for the creation and distribution of Voronoi cells 295 (the region between nodes) that can be optimized to identify locations for traction elements 245.

In addition to using experimental data representative of a performance characteristic of the foot and/or physical characteristics of a foot of the user as input parameters, aesthetic and/or performance based preferences of an athlete can be used to assist in the customization of the footwear. For example, the importance of elements such as, but not limited to, the size, distribution, and shape of traction elements, the level of traction required, the durability of the footwear, the flexibility of the footwear, and/or the weight of the footwear may vary from athlete to athlete. As a result, one embodiment of the invention allows for an athlete to control the design of the customized footwear depending upon the relevant importance of various controllable user preference-based input parameters or selection criteria. In this embodiment, the experimental performance data and/or the physical characteristic data is used to create a baseline customized sole with traction elements distributed to optimize traction for specific user. This baseline customization can then be modified to account for user preferences, for example by reducing the size of the traction elements and/or creating voids between traction elements to reduce weight (where low weight is more important to the athlete than improved traction) or to vary the shape, size, and distribution of the traction elements where one specific traction element type is considered more comfortable, better performing, and/or more aesthetically pleasing to an athlete. In one embodiment different traction element and spike shapes may be selected depending upon underfoot conditions and surfaces, weather conditions, and/or athletic activity being performed. In addition, as straight running and running around a curve produce different performance metrics for an athlete and each shoe of the athlete, an athlete can select, as an input parameter, the extent to which the traction element distribution and orientation is weighted by the straight running input parameter data and the curved running input parameter data. In one embodiment different performance requirements and traction requirements may be needed or preferred for different races (e.g., for a sprint, a middle distance event, a long distance event, a hurdling event, etc.).

In one embodiment a shoe may be adapted to receive detachable and interchangeable outsole elements (e.g., outsole spike plates) or ground contacting midsole elements, allowing the traction of the shoe to be adjusted by replacing the outsole elements depending upon the specific requirements of the athlete. For example, an athlete may have a number of different outsole elements customized for various weather conditions, underfoot conditions, races, and other relevant parameters, with the athlete free to select the most appropriate plates for a specific event.

In one embodiment the customized physical characteristic of the outsole of the footwear may include, or consist essentially of, a tread pattern, with the specific pattern shape and orientation customized to address the specific performance metric information and user preference information of a specific athlete.

In one embodiment the weight can be reduced by removing material from carefully selected regions of the outsole through the creation of cavities or voids. The voids may be placed strategically to only be located in regions where less significant traction is needed (such as in the midfoot region for a heel striker) and/or in regions where the addition of voids would not adversely affect the structural integrity of the outsole. The creation of voids and/or cavities can also create regions of increased flexibility, which may beneficially affect the performance of the footwear for some athletes.

Figures 24A, 24B, 24C:
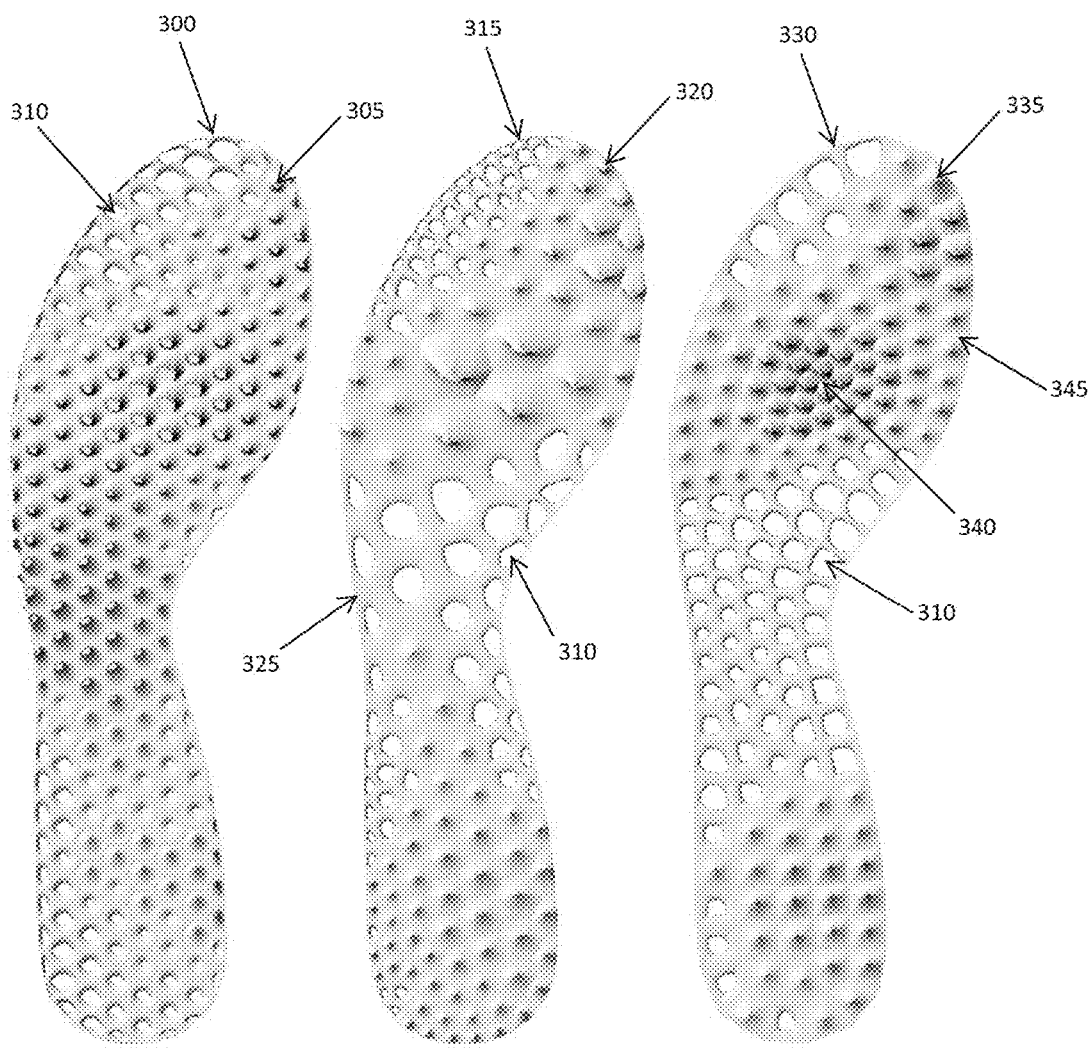
FIGS. 24A to 24C are plan views of outsole plates for an article of footwear based on a single athlete's measured performance data but with different sets of selection criteria, in accordance with one embodiment of the invention.

Exemplary configurations of footwear outsoles, and more particularly outsole plates for a track spike shoe, are shown in FIGS. 24A through 24C. Each of the three plates shown is generated from the same input parameters and performance metrics, with the variations in the finished designs and configurations based upon the selection of different user preferences. In the embodiment of FIG. 24A, for example, the plate 300 is designed with regularly distributed traction elements 305 and voids 310, with the size of each traction element 305 based on the magnitude of the performance metric data in that region. In addition, the user preference is set with traction being a relatively important factor while weight reduction is of lesser importance, resulting in a greater number of traction elements 305 and a fewer number of weight reducing voids 310.

In the embodiment of FIG. 24B the plate 315 is designed with irregular traction element 320 and void 310 distribution, with the size of the traction elements 320 relating directly to the magnitude of the performance metric data in that region, and with more emphasis being place on low weight and higher flexibility, resulting in a greater number of voids, especially within the midfoot region 325. In the embodiment of FIG. 24C the plate 330 is designed with irregularly distributed traction elements 335, with the traction elements 335 clustered together in a tighter formation in regions having a high magnitude of performance metric data (such as in the central portion 340 of the forefoot region 345.

Figures 25A, 25B:
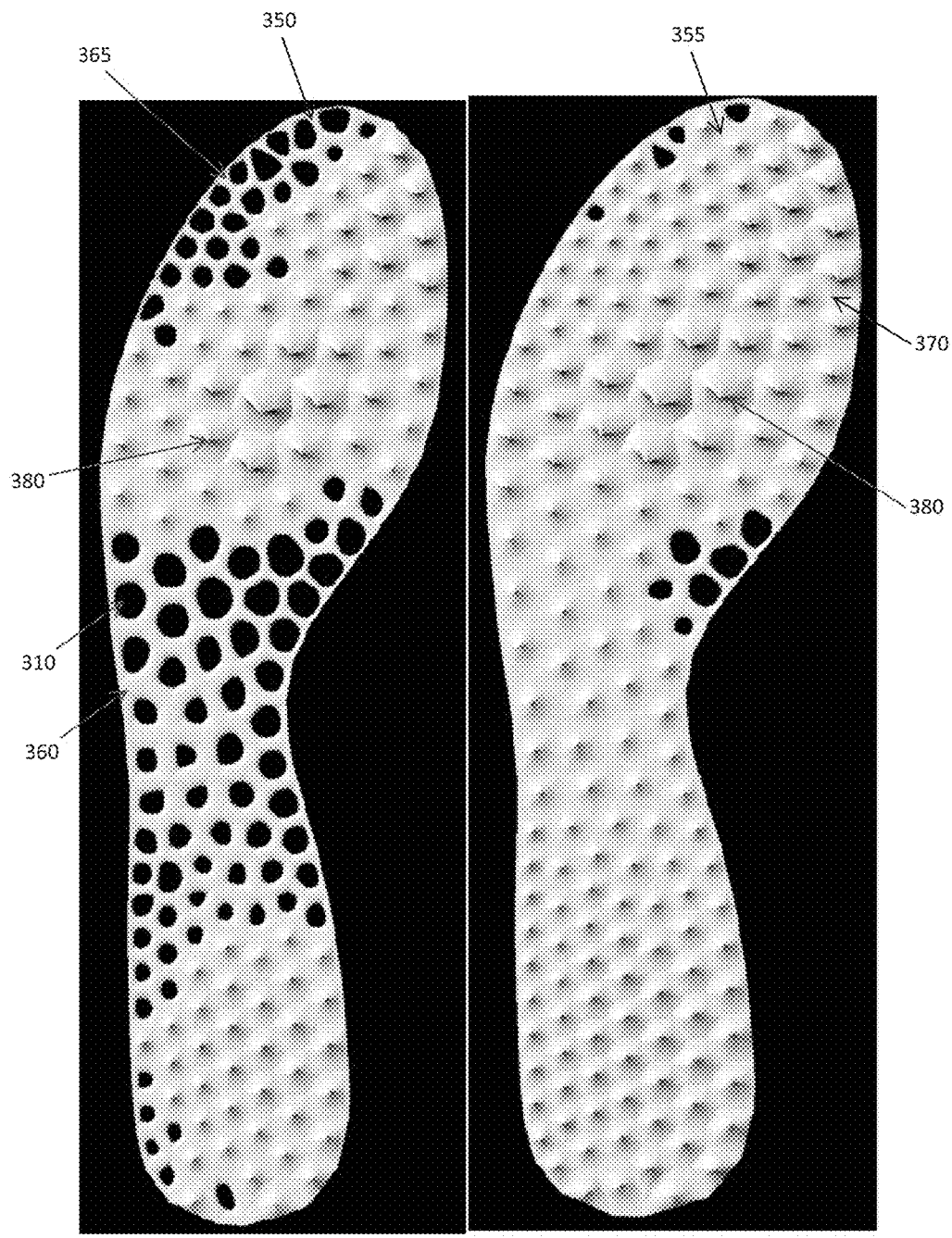
FIGS. 25A to 25E are plan views of other outsole plates for an article of footwear based on a single athlete's measured performance data but with different sets of selection criteria, in accordance with one embodiment of the invention.

Further examples of variations in customized design based on variations in user preference criteria for a single set of input parameters and performance metrics can be seen in FIGS. 25A to 25E. For example, FIGS. 25A and 25B show two plates (350, 355) with identical input parameters and performance metrics but with the plate 350 designed to lower weight (by increasing void 310 distribution and size, especially within the midfoot region 360 and the outer edge 365 of the forefoot region 370 where the magnitude of the performance metric data is lower), while plate 355 is designed with traction being set as a more important parameter than weight reduction (resulting in fewer voids 310 and more traction elements 380).

Figures 25C, 25D:
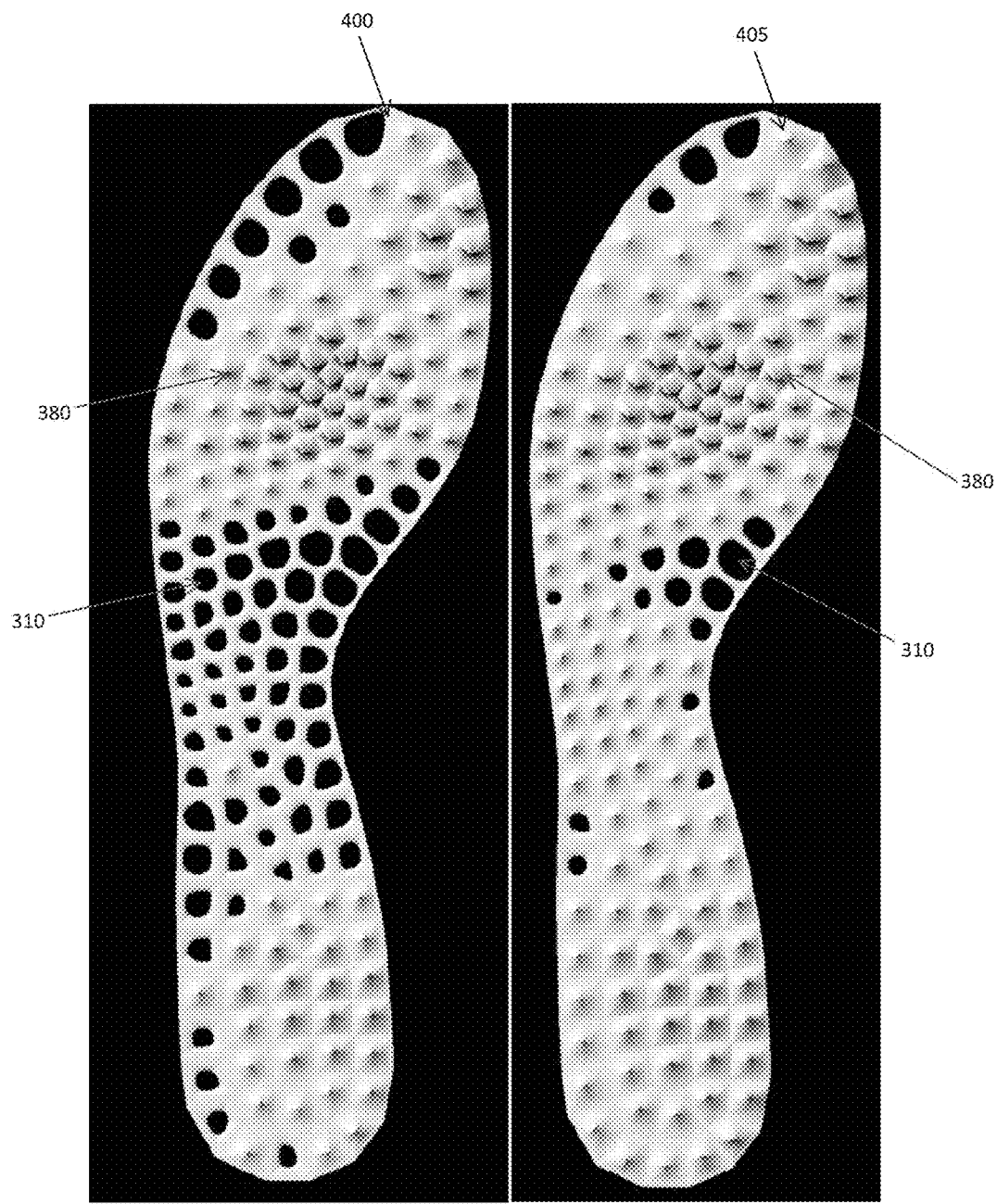

Similarly, FIGS. 25C and 25D show plates (400, 405) having a different design configuration for the same input parameters and performance metrics as in FIGS. 25A and 25B, with the size of the traction elements 380 of the plates (400, 405) limited to a set size smaller than that allowed in the embodiments of FIGS. 25A and 25B, and with the traction elements 380 clustered closer together in regions having large magnitude performance metric data. The plates (400, 405) are again designed to have the same characteristics but with the plate 400 emphasizing low weight over high traction, and with the plate 405 emphasizing traction to a greater extent that the plate 400, resulting in fewer voids 310.

Figure 25E:
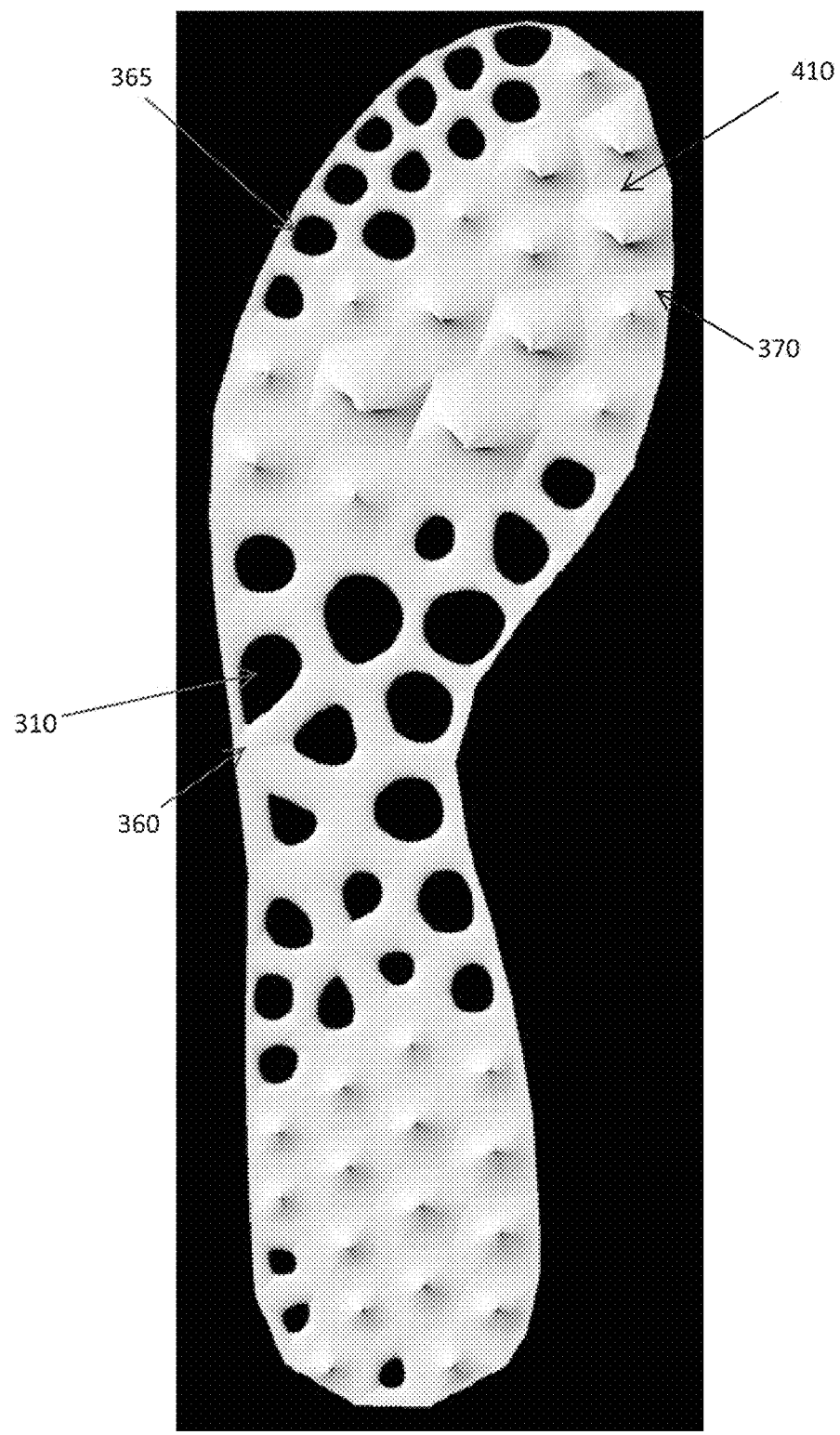

FIG. 25E shows another configuration of outsole plate 410 designed using the same input parameters and performance metrics as in FIGS. 25A and 25D. In this embodiment the selection criteria has been set to reduce the number of traction elements 380 but to allow for significantly increased size of traction element 380 in regions corresponding to a larger magnitude of performance metric results. Again, the selection criteria has been set to reduce weight by increasing void 310 distribution and size, especially within the midfoot region 360 and the outer edge 365 of the forefoot region 370 where the magnitude of the performance metric data is lower. In various alternative embodiments distributions of traction elements 380 and voids 310 can be controlled by a number of selection criteria relating to a number of performance and aesthetic aspects, such as, but not limited to, traction element and/or void size, shape, distribution, number, and/or size variation.

In one embodiment, as shown in FIGS. 24A to 25E, the sole plate including the traction elements can be formed as a plate-like structure with traction elements extending from the plate and voids or cavities formed within certain portions of the plate. In an alternative embodiment, as shown in FIGS. 26A to 31B, the sole plate can be formed as a plurality of traction elements with a web-like structure of interconnection elements (e.g., bars) 415 connecting the traction elements. In further alternative embodiments the plate can be formed in any appropriate manner having the necessary structural requirements to meet the performance demands of the wearer.

Figures 26A, 26B:
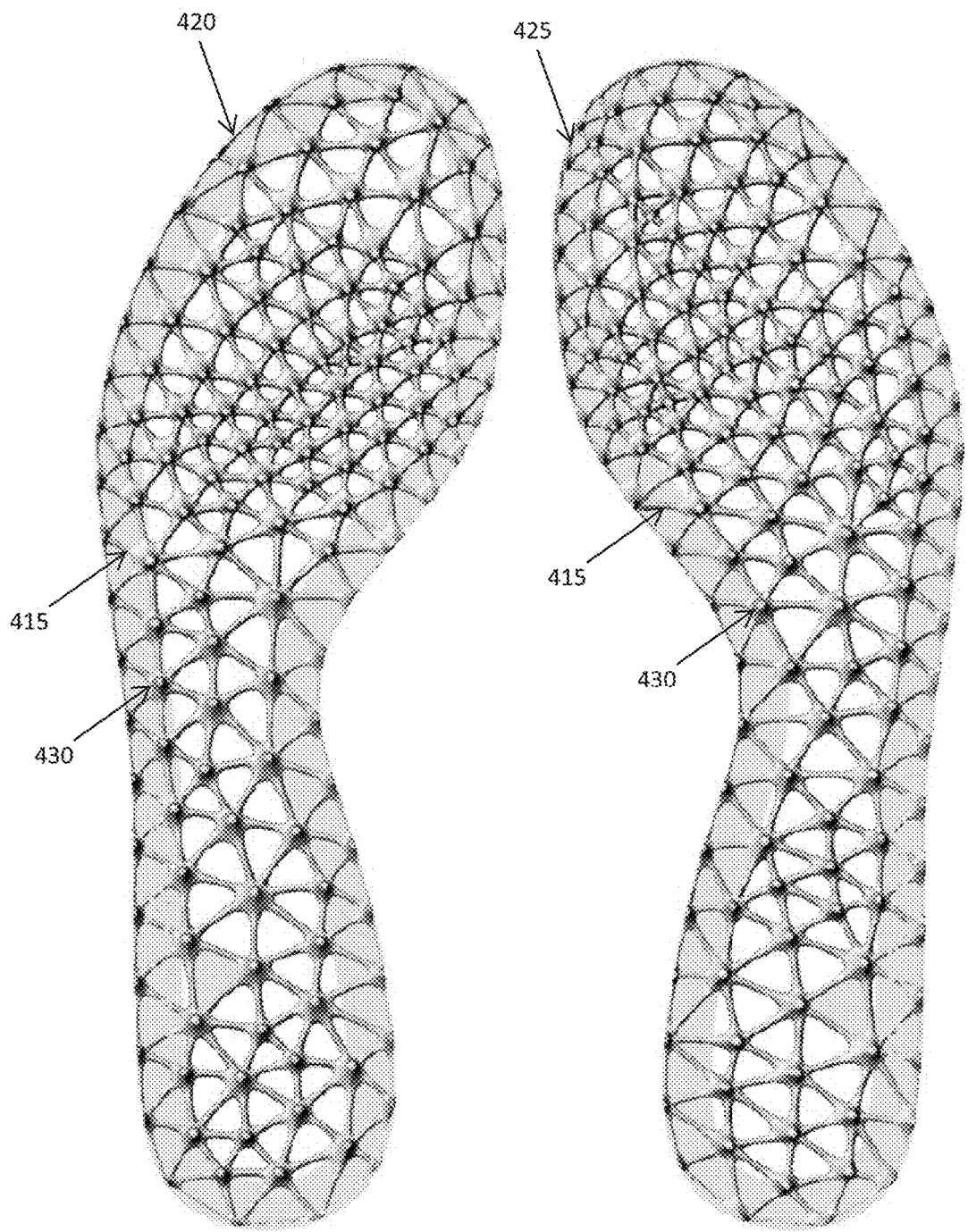
FIGS. 26A and 26B are plan views of outsole plates for an article of footwear based on a first and second athletes measured performance data analyzed using the same selection criteria, in accordance with one embodiment of the invention.
Figures 29A, 29B:
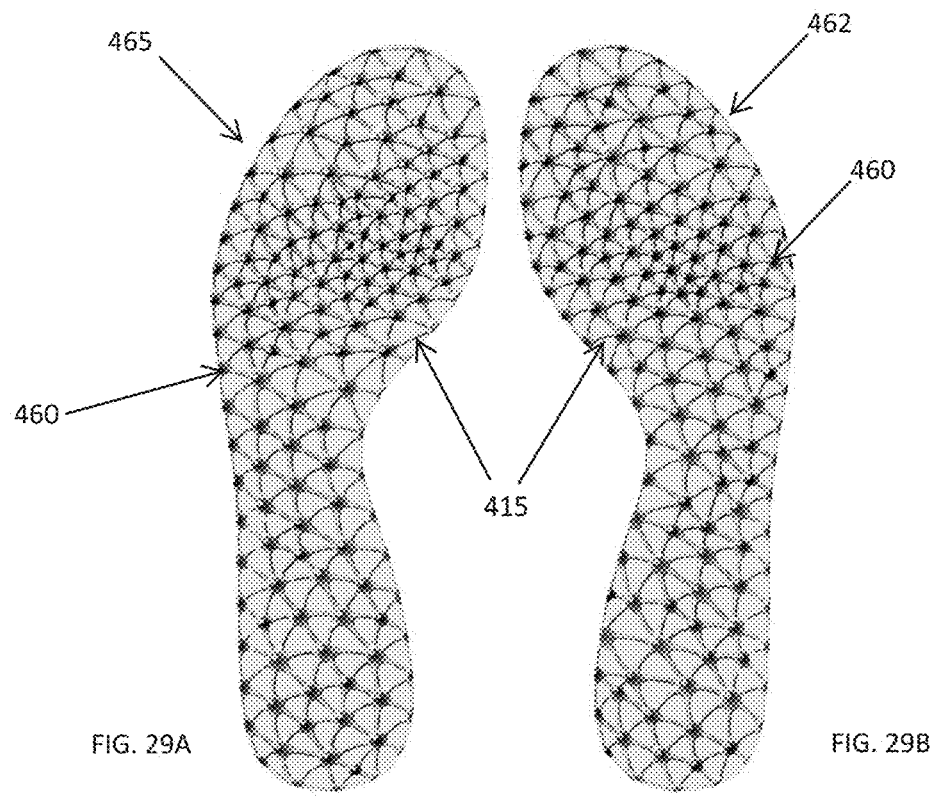
FIGS. 29A and 29B are plan views of outsole plates for left and right shoes of another athlete based on measured performance data while running round a corner portion of a track, in accordance with one embodiment of the invention.
Figures 30A, 30B:
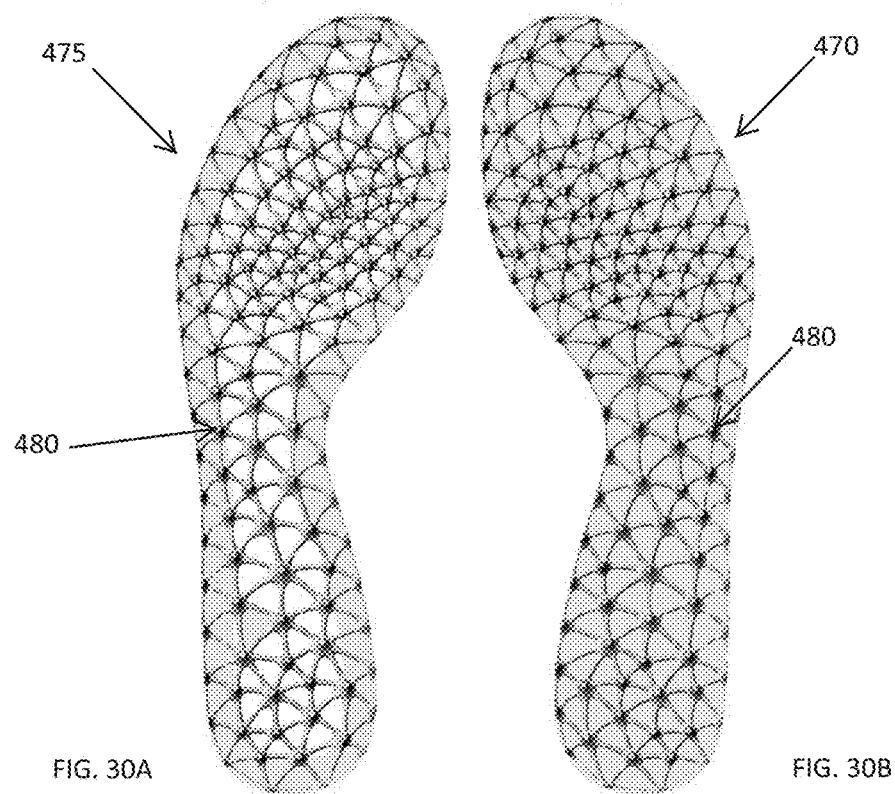
FIGS. 30A and 30B are plan views of outsole plates for left and right shoes of the athlete of FIGS. 29A and 29B based on measured performance data while running along a straight portion of a track, in accordance with one embodiment of the invention.

FIGS. 26A and 26B show plates (420, 425) designed using the same user selection criteria (e.g., traction element shape, size, distribution, etc.) and the same plate structure (with bars 415 connecting individual traction elements 430 in web-like or lattice structure) but with input parameters (e.g., pressure and force data) and performance metrics (e.g., analyzed and processed input data based on a preselected algorithm) from two different athletes. As can be seen, the algorithms used to process the input parameters, even for the same user selection criteria, produce different traction element 430 distributions due to the different input parameters generated by different athletes. The addition of a web-like structure with bars 415 or other elongate elements allows for the incorporation of structural elements designed to provide controlled stability, flexibility/stiffness, support, and/or protection depending on the shape, thickness, and orientation of the elongate elements.

In one embodiment an outsole plate for a track spike-type running shoe can be formed with mounting elements allowing detachable spikes to be mounted to the plate to provide further traction in addition to the traction elements integrally formed with the plate. These mounting elements may be of any size, shape, and configuration, depending on the specific spikes and spike configuration required. In various embodiments any number of spikes can be mounted to the plate, with 3, 4, 5, or 6 spikes being utilized by many track athletes. An exemplary outsole plate 440 for a track spike-style shoe with mounting elements 445 for track spikes is shown in FIG. 27.

In one embodiment plates can be formed to account for the different ground interactions between the ground and the shoe for both a left foot and a right foot while an athlete runs around a curved track. Exemplary plates for a left shoe 450 and a right shoe 455 can be seen in FIGS. 28A and 28B, with the different input parameters (e.g., pressure and force data) for each foot resulting in different traction element 460 configurations for each plate. In one embodiment, a pair of shoes specifically adapted for running around a curved track could include both customized sole plates and specially designed, and potentially customized, uppers, such as the uppers described in U.S. Patent Publication No. 2010/0229426, the disclosure of which is incorporated herein by reference in its entirety. Another pair of outsole plates (462, 465) designed from input parameters taken during curved track running can be seen in FIGS. 29A and 29B, with the results calibrated for a different sole plate shape to that of FIGS. 28A and 28B, and for a different athlete's input parameters. In various embodiments the processing algorithms may be designed to distribute traction elements and/or voids in the surface of any shape of plate or outsole, depending upon the specific shape of the shoe.

Figures 31A, 31B:
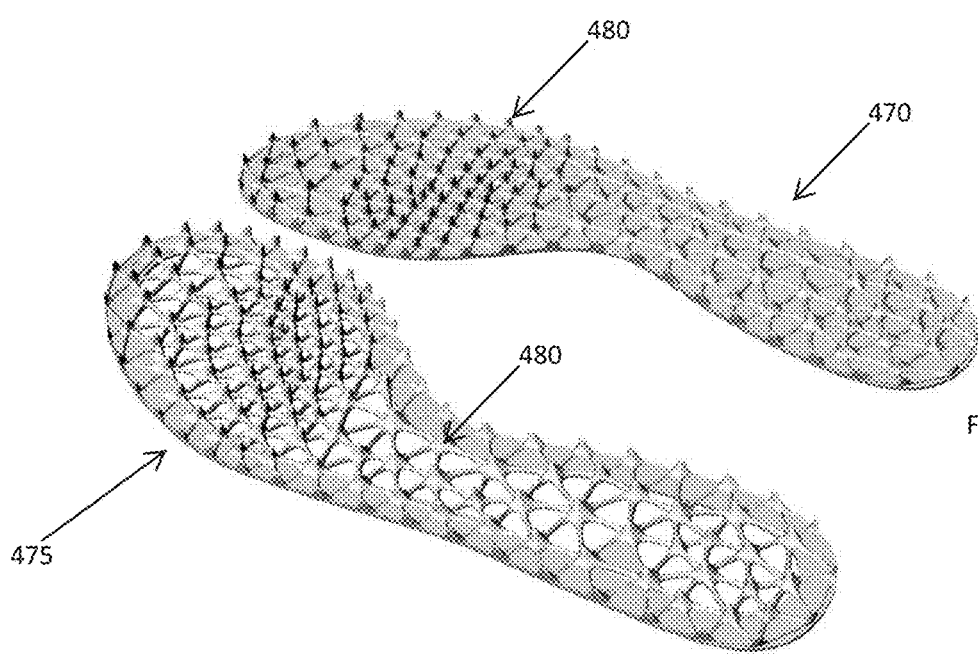
FIGS. 31A and 31B are perspective views of the outsole plates of FIGS. 30A and 30B.

A pair of outsole plates (470, 475) utilizing input parameter measurements taken during straight running is shown in FIGS. 30A through 31B, with a left foot plate 470 and a right foot plate 475 shown in both plan view and perspective view. As shown in FIGS. 31A and 31B the plates (470, 475) may be formed as substantially flat structures with traction elements 480 extending therefrom. In an alternative embodiment, such as the soleplate 440 shown in FIG. 27, the plates can be manufactured with a curved or angled profile to allow the plate to mate to a shoe sole, or a portion thereof (e.g., an outsole having a curved or angled lower surface profile). In various alternative embodiments any appropriate shape of sole plate or outsole element may be designed.

In one embodiment of the invention the input parameters maybe utilized to determine performance metrics that can be used to design a customized midsole or a customized midsole component (e.g., a heel cup and/or forefoot drop-in component) in addition to, or in place of, a ground contacting structure with traction elements. An exemplary midsole designed from analysis of pressure and force measurement input parameter data can be seen in FIGS. 32A to 32C. In this embodiment, a midsole 500 is formed as a lattice or web-like structure with a plurality of elongate elements 505 extending between nodes 510. The distribution of elongate elements 505 and nodes 510 within the lattice structure is determined by the performance metric data obtained from the input parameters of a specific athlete and the selection criteria of that athlete. More particularly, the elongate elements 505 and nodes 510 can be arranged to provide areas of increased or decreased support, increased or decreased cushioning, and/or increased or decreased stability in different regions of the midsole 500.

Figure 32A:
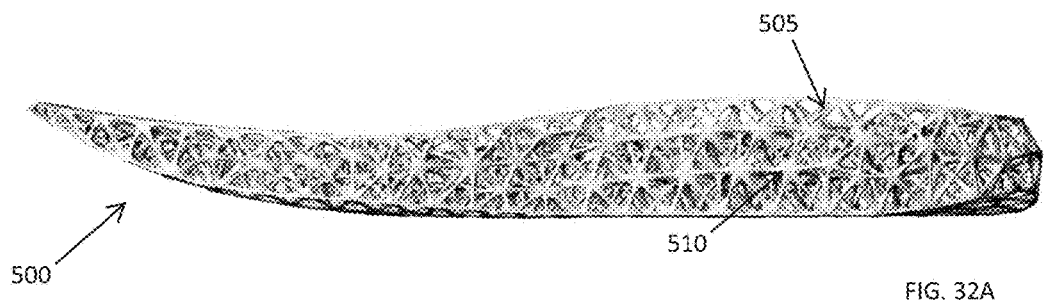
FIG. 32A is a side view of a midsole for an article of footwear, in accordance with one embodiment of the invention.
Figure 32B:
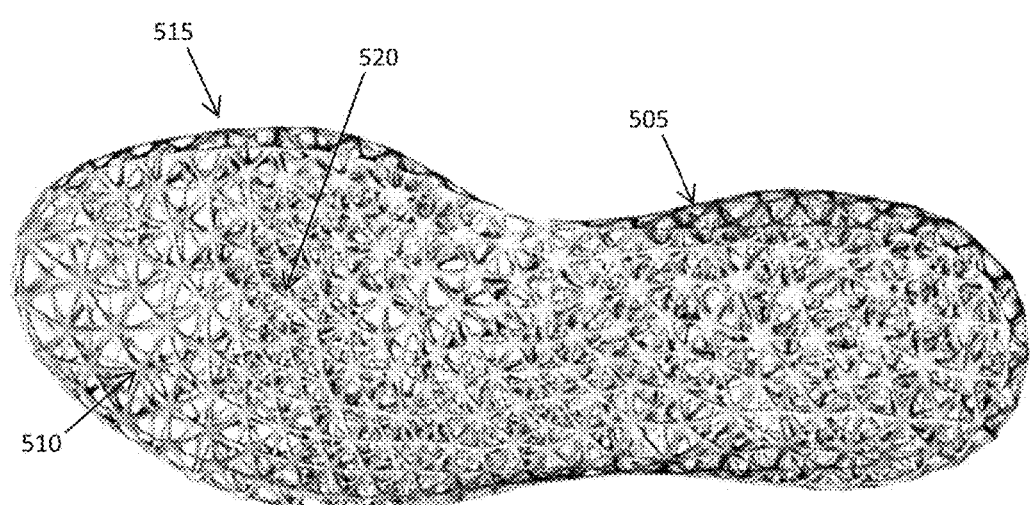
FIG. 32B is a plan view of the midsole of FIG. 32A.
Figure 32C:
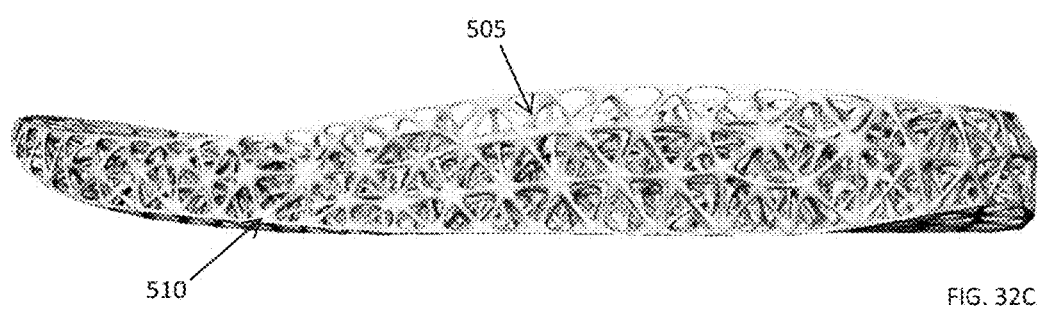
FIG. 32C is a perspective view of the midsole of FIG. 32A.

In the embodiment of FIGS. 32A through 32C the lattice structure is arranged such that more nodes 510, with shorter elongate elements 505 are positioned in regions of high performance metric values, thereby providing additional structural support in those regions, such as in the central forefoot region 515 proximate the position of the metatarsal heads of the athlete 520. In various embodiments the properties of the lattice structure can be controlled by specifying various aspects of the structure such as, but not limited to, the length of each elongate element 505, the thickness of each elongate element 505, the density of each elongate element 505, and/or the material(s) for each elongate element 505. In addition, properties such as, but not limited to, the size, shape, density, and/or material(s) of the nodes 510 may also be controlled to ensure certain performance characteristics of the midsole 500 are met. In the embodiment of FIGS. 32A through 32C the elongate elements 505 and nodes 510 form triangular structures. In alternative embodiments any appropriate structural formation may be utilized. In one embodiment, elongate elements 505 and nodes 510 form a plurality of polyhedron shapes such as, but not limited to, tetrahedrons (i.e., a polyhedron having four triangular faces), cubes, octahedrons, dodecahedrons, icosahedrons, etc. For example, a midsole 500, or a portion thereof, may be formed from a matrix of elongate elements 505 forming a plurality of tetrahedron shaped "cells". The relative size, shape, and structural properties of the cells may be varied throughout the midsole 500 to impart different structural characteristics to different regions of a shoe.

Structures such as the lattice structure of FIGS. 32A through 32C may be beneficial to an athlete in that it allows for the customized design of the sole component (e.g., the midsole or midsole element) to meet the performance requirements of the athlete while also minimizing weight by allowing for an open web-like construction with open cavities between the elongate elements 505 and nodes 510. In one embodiment the lattice structure may be left as an open structure. In an alternative embodiment a material (e.g., lightweight foam) may be injected into the lattice structure to fill the open cavities, thereby providing additional structural support.

Figure 32D:
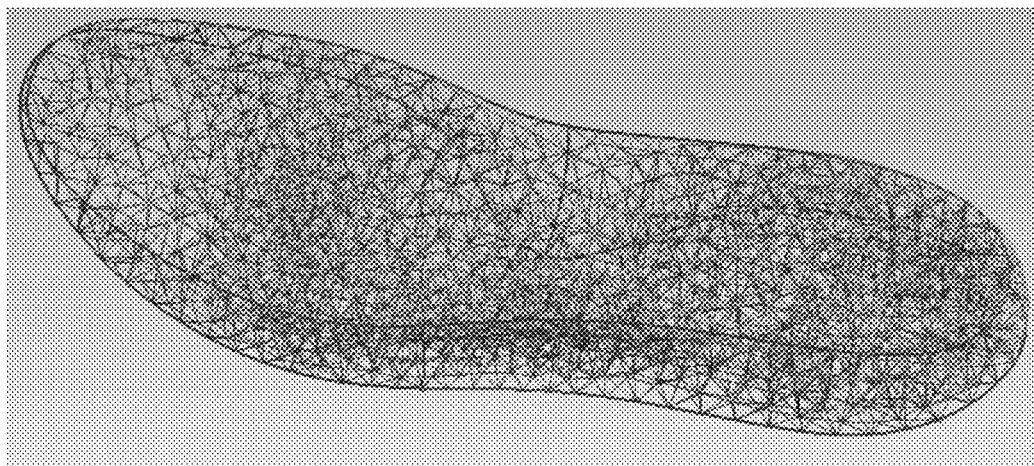
FIG. 32D is a perspective view of a mathematical mesh used to design the midsole of FIG. 32A.
Figure 33:
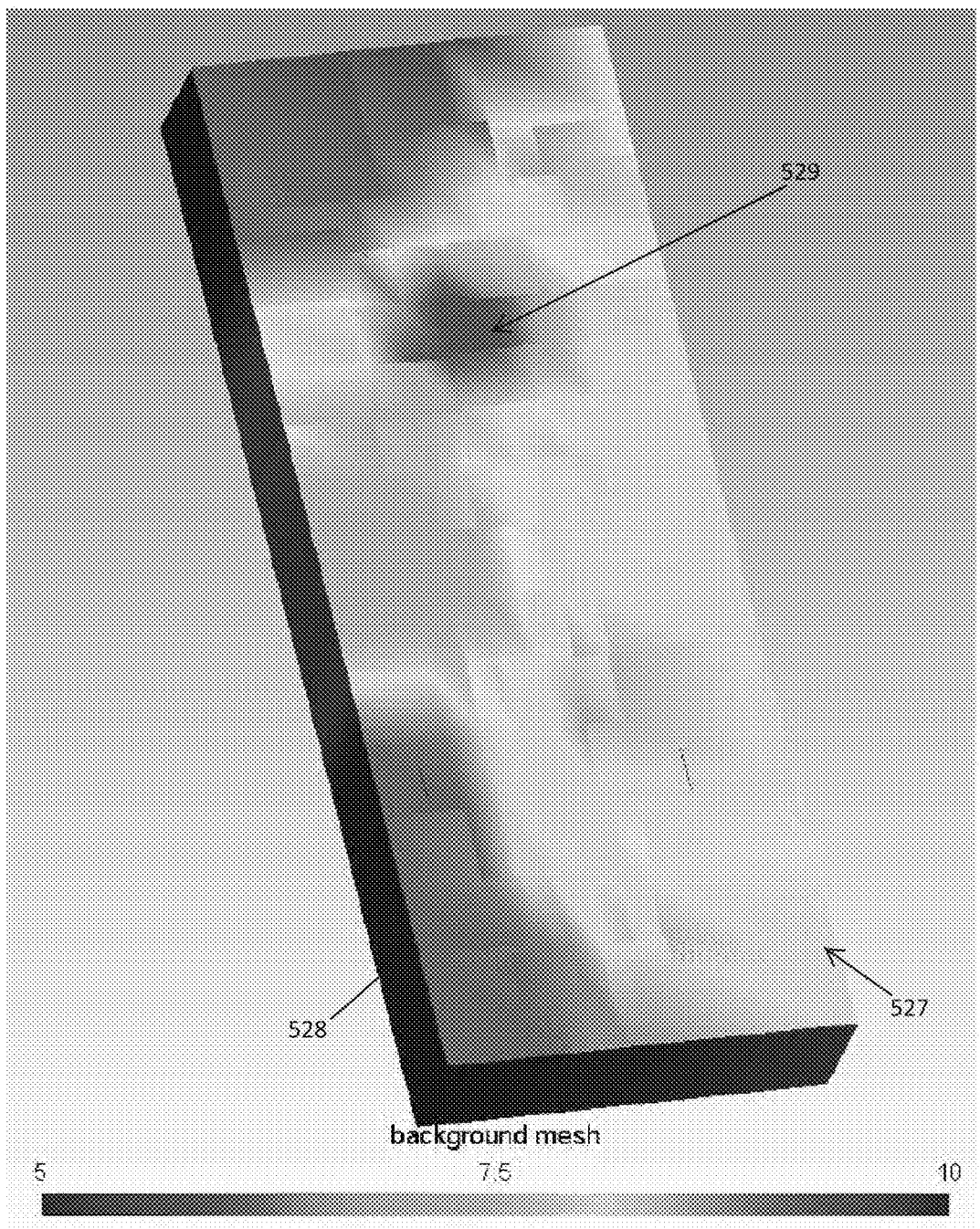
FIG. 33 is a schematic perspective view of a scalar hexahedron pressure mapping distribution for calculating a midsole mesh, in accordance with one embodiment of the invention.
Figure 34E:
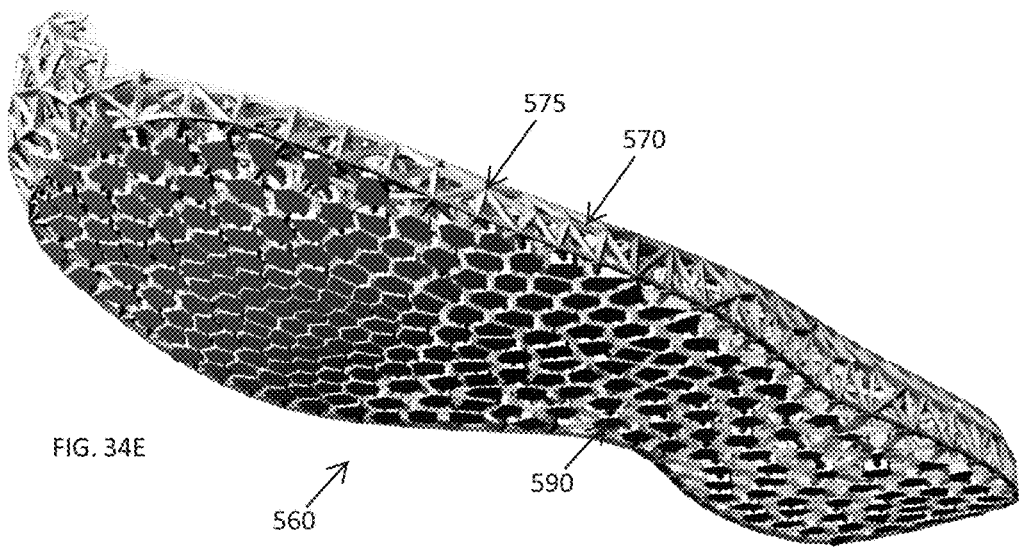
FIG. 34E is a perspective view of the midsole of FIG. 34A.
Figure 34F:
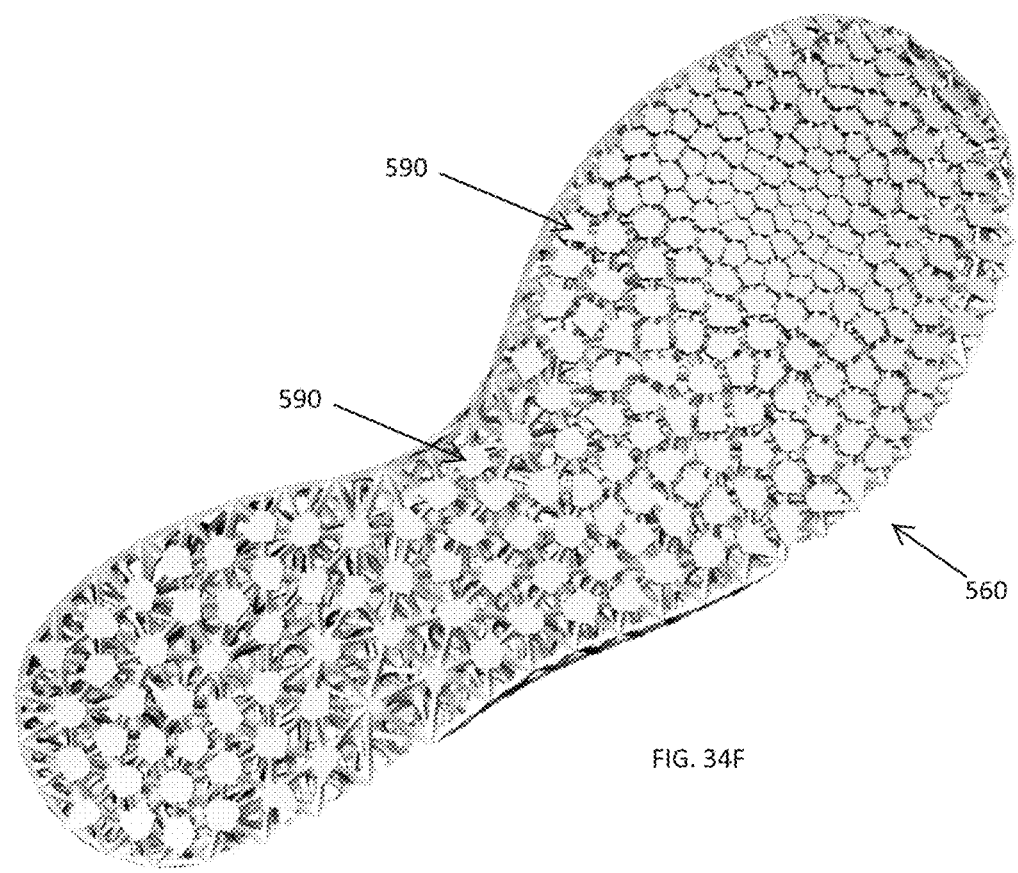
FIG. 34F is a another perspective view of the midsole of FIG. 34A.

In one embodiment the design of the midsole lattice structure may be created through processing of the performance metric data by mathematical algorithms such as, but not limited to, circle packing, Delaunay triangulation, volumetric meshing, and/or Voronoi decomposition. An exemplary structural construct for a midsole using Voronoi decomposition to analyze performance metric data for an athlete is shown in FIG. 32D, with the performance metric data, represented as a scalar hexahedron pressure mapping distribution, for calculating a midsole mesh used in the analysis shown in FIG. 33. In this embodiment, the pressure distribution within a volumetric representation of the sole of an article of footwear is represented by a contour map 527, with high pressure regions 528 and low pressure regions 529 distributed about the volume according to the pressure measurements taken for a particular athlete.

Another exemplary midsole designed and constructed according to the methods and systems described herein is shown in FIGS. 34A to 34F. In this embodiment the midsole 530 includes a forefoot region 535 having a wrapped toe section 540, a midfoot region 545, and a heel region 550. The midsole 530 further includes an upper surface 555 for engaging an upper of a shoe and a lower surface 560 for engaging an outsole of a shoe and/or for providing a ground contact surface (without the need for providing an additional outsole element, or elements). The midsole 530 further includes a side wall 565, which may be exposed when assembled into the finished shoe or which may be fully or partially covered by a clear or opaque covering element when assembled into the finished shoe. The structure of the midsole 530 includes a plurality of elongate elements 570 joining at a plurality of nodes 575, with the combined elongate elements 570 and nodes 575 forming a plurality of open triangular structural segments 580. As discussed above, the specific arrangement of elongate elements 570 and nodes 575 can be customized based on the specific performance metrics for a given athlete, with the midsole 530 thereby providing customized cushioning, support, and flexibility (and other possible performance benefits) for a specific athlete.

In various embodiments any appropriate skin, covering, and/or encapsulate may be added to the structure after formation to provide an outer surface covering for the structure, or portions thereof. This may provide protection for the structure, prevent clogging of the structure with mud, water, etc., provide additional structural properties to the structure, and/or provide unique aesthetic elements to the structure. Skins/coverings may be manufactured from any appropriate material such as, but not limited to, TPU's, TPE's and/or knitted, woven, or non-woven textiles.

The upper surface 555 may be glued, stitched, or otherwise attached to an upper of a shoe and, for example, to a strobel board for an upper of a shoe. In certain embodiments an insole may be placed above the midsole 530 in a finished shoe to provide a separate layer between the midsole 530 and a foot of a wearer of the shoe. In certain embodiments a strobel board positioned above the upper surface 555, to which the upper surface 555 is attached, provides a material layer in between the midsole 530 and the foot of the wearer in addition to, or instead of, a separate insole component. In an alternative embodiment the upper surface 555 is attached to the upper only at the edges, with no strobel board, insole, or other material layer coming between the midsole 530 and the foot of a wearer of the finished shoe.

In the embodiment of FIGS. 34A to 34F the upper surface 530 includes a plurality of voids 585, which can reduce the weight of the midsole 530 and provide for breathability between the midsole 530 and an upper of a shoe. The voids 585 may be arranged in any particular pattern and be of any appropriate shape, depending upon the specific performance, breathability, and weight requirements of the footwear. In one embodiment the location, size, and shape of the voids 585 can be determined based upon the specific performance metrics of an athlete, thereby providing a customized breathability and load distribution plate. In one embodiment the upper surface 555 may not have any voids 585 therein, which may be beneficial, for example, in providing additional surface area onto which the upper can be bonded and may also be beneficial in embodiments where additional breathability is not desired or necessary (e.g., in waterproof footwear). In one embodiment the shape of the upper surface 555 may be contoured specifically to the foot shape of a given athlete, thereby providing a customized fit for the athlete.

Figure 35:
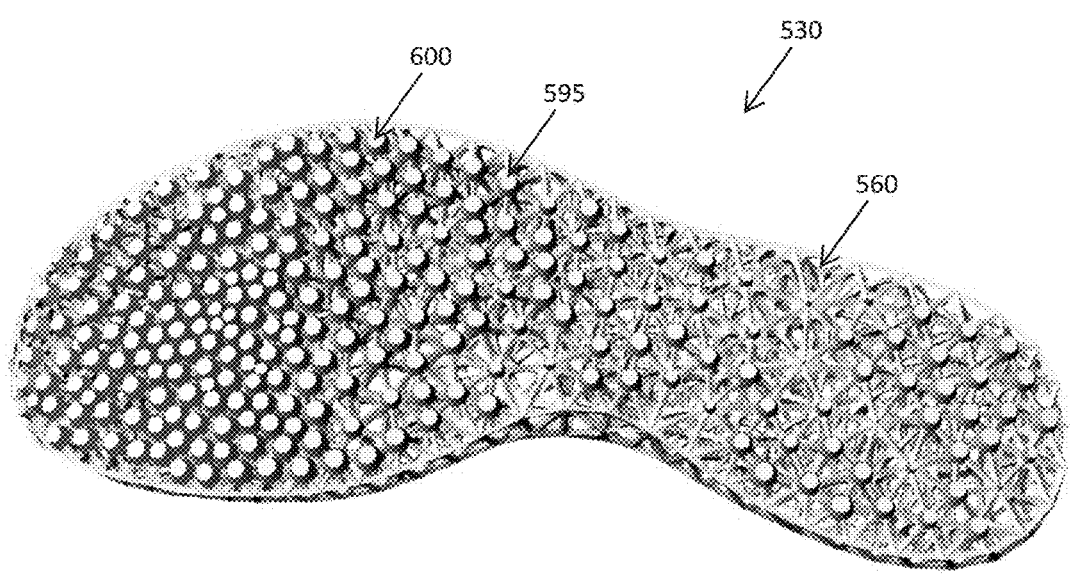
FIG. 35 is a perspective bottom view of another midsole for an article of footwear, in accordance with one embodiment of the invention.
Figure 36A:
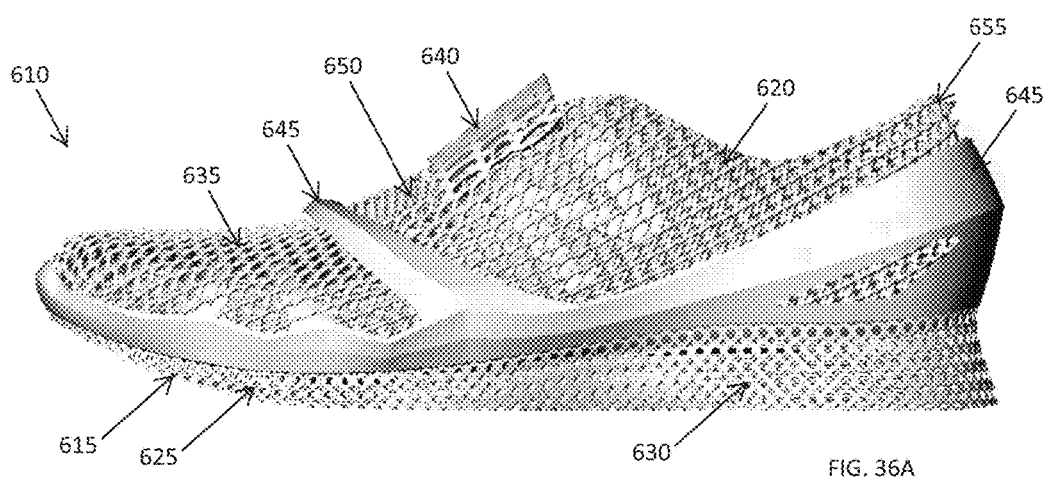
FIG. 36A is a lateral side view of an article of footwear, in accordance with one embodiment of the invention.
Figure 36B:
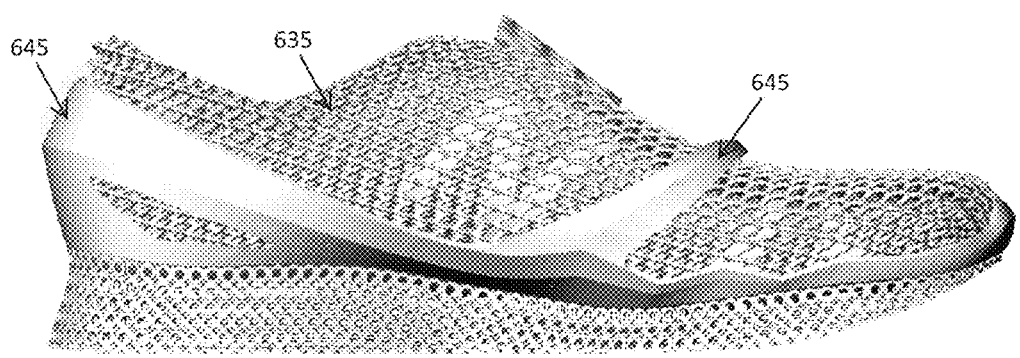
FIG. 36B is a medial side view of the article of footwear of FIG. 36A.
Figure 36C:
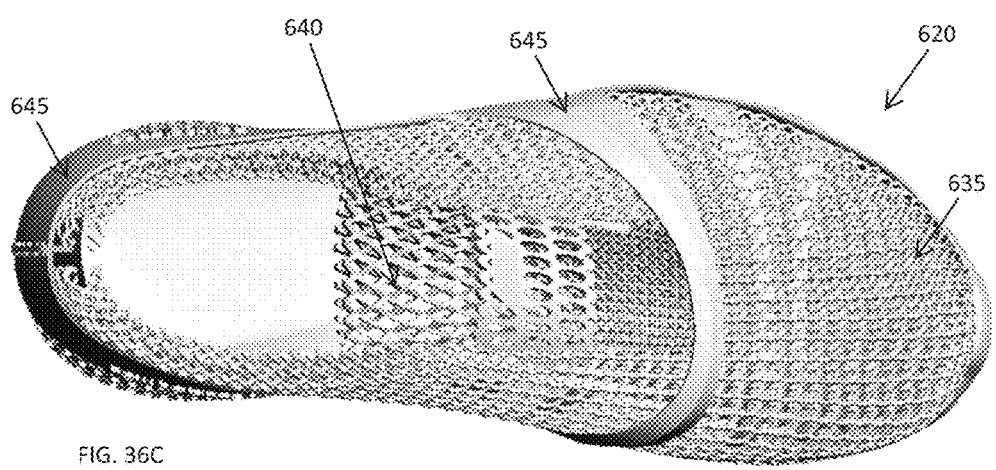
FIG. 36C is a top view of the article of footwear of FIG. 36A.
Figure 36D:
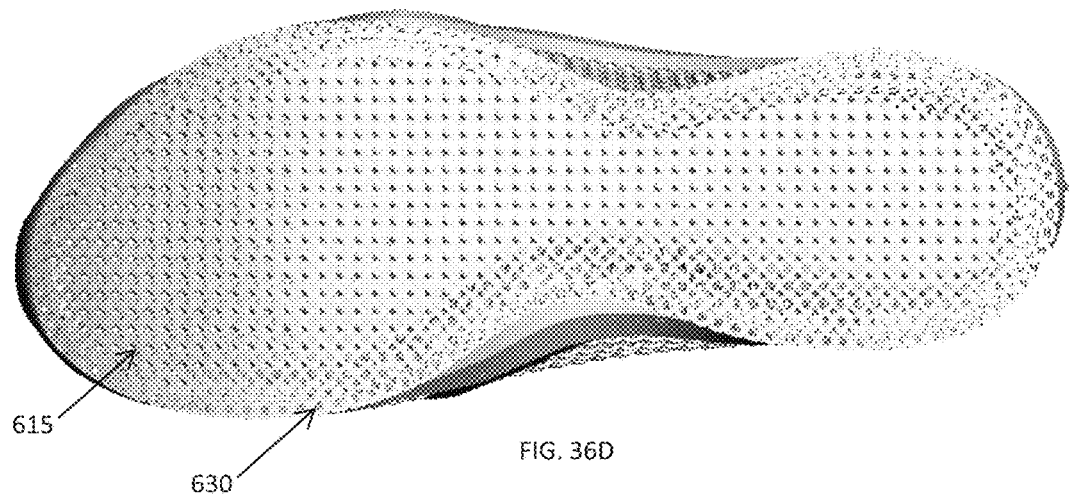
FIG. 36D is a bottom view of the article of footwear of FIG. 36A.
Figure 36E:
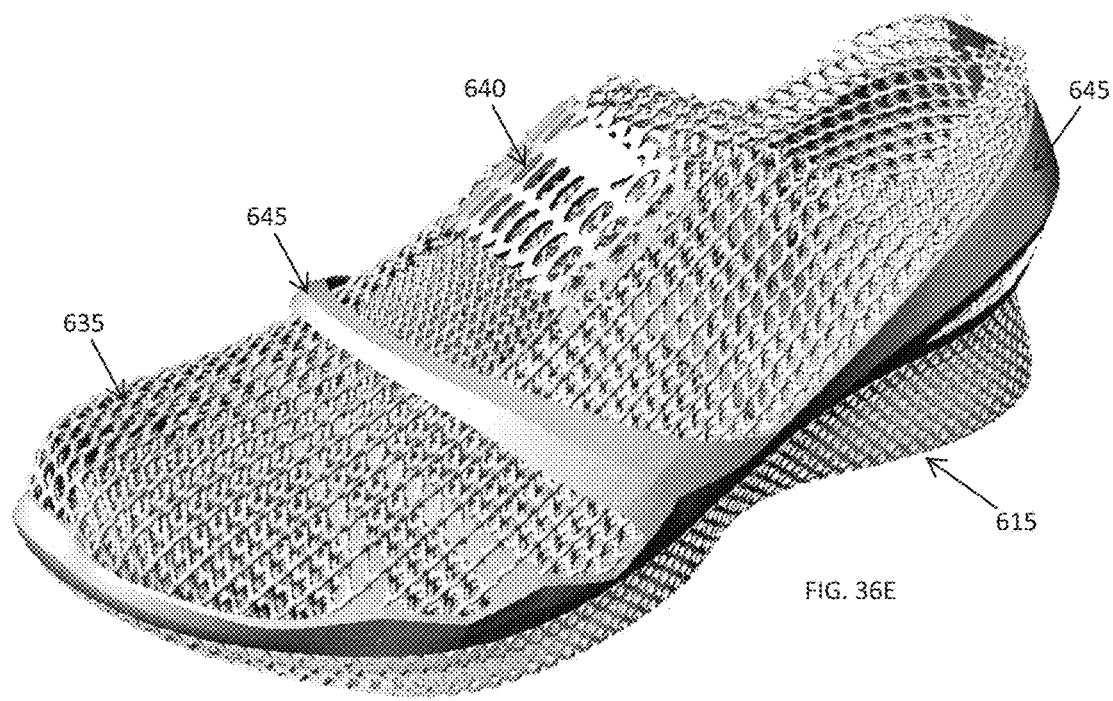
FIG. 36E is a perspective view of the article of footwear of FIG. 36A.

The lower surface 560 of the midsole 530 includes a plurality of flattened lower contact surfaces 590 which can, in various embodiments of the invention, provide a surface onto which one or more outsole elements may be affixed (e.g., by gluing), or which can provide a direct ground contact surface for the midsole 530. The shape, size, and configuration of these lower contact surfaces 590 may be standardized or may be customized through analysis and application of an individual athletes input parameters, performance metrics, and/or selection criteria. In an alternative embodiment the lower surface 560 can be a solid, void free surface. Another embodiment of the invention, including a midsole 530 having a plurality of traction elements 595 extending from the bottom surface 560, can be seen in FIG. 35. In this embodiment, the bottom surface 600 of the traction elements 595 provides a direct ground contact surface for the midsole 530, thereby allowing the midsole 530 to function without the need to add an additional outsole element.

In one embodiment the input parameters and algorithms may be utilized to design an insole for a shoe, with the insole customized to the specific physical characteristics of the athlete and the structure of the insole designed to provide a customized feel and/or performance characteristic for the athlete. In alternative embodiments the methods and systems described herein could be used to design and manufacture any outsole, midsole, and/or insole structures and components such as, but not limited to, full outsoles, midsoles, and/or insoles, inserts for placement within an outsole, midsole, and/or insole (e.g., within the forefoot, midfoot, and/or heel of the shoe and/or in the medial side, lateral side, and/or central section of the shoe. In one embodiment the systems and methods described herein can be utilized to create customized uppers and/or upper portions in addition to, or instead of, the customized sole elements.

An exemplary shoe 610 including a sole 615 and upper 620 manufactured as a single unitary structure in accordance with the methods and processes described herein is shown in FIGS. 35A to 35E. In this embodiment the sole 615 includes a midsole 625 formed from a plurality of adjoining circular elements 630 spaced apart to form an open web-like structure. An upper 620 is integrally formed with the sole 615 to create a unitary structure forming the shoe 610, with the upper 620 including linked mesh-like portions 635 forming the majority of the upper 620, including the tongue 640, with support elements 645 providing additional structural support in regions of high strain (e.g., in the midfoot region 650 and a heel region 655). In an alternative embodiment the customized unitary construction may only form specific regions of the sole and/or upper of a shoe, with additional material and structural elements being attached to the customized structure. In various embodiments the shoe 610 can be constructed with any appropriate closure means, with the closure means formed along with the upper and/or sole elements or attached to the shoe after formation. In one embodiment both sides of a hook and loop-type arrangement can be created in an additive manufacturing process, with the resulting hook and loop structure separable after manufacture to provide a closure means.

In one embodiment an upper, or portion(s) thereof, can be formed through methods described herein (e.g., through additive manufacturing) and thereafter heat welded, fused, bonded, or otherwise attached to a textile or other material to form a finished part. In one embodiment a flat shell for an upper can be formed though additive manufacturing and thereafter heat pressed (or otherwise bonded or attached) to a textile to form a finished upper. In one embodiment a shaped mold/heat press form can be created (either with the shell or separately from the shell) which can then be used to ensure that structural definition (e.g., raised portions) of the shell are not lost during heat pressing procedure.

Utilizing the methods and processes described herein any of the elements of the sole 615 and/or upper 620 of the shoe 610 can be customized, based on the specific input parameters, performance metrics, and/or selection criteria of an athlete, to produce a fully customized shoe. For example, the position, size, shape, pattern, structure, and material properties of the support elements 645 can be customized, based on the input parameters of the athlete, to provide support specifically addressing the running style, foot shape, performance requirements, and aesthetic requirements of an athlete. In addition, elements such as, but not limited to, the position, size, shape, pattern, structure, and material properties of the mesh-like portions 635 may also be customized, based on the input parameters of the athlete, to provide support specifically addressing the running style, foot shape, performance requirements, and aesthetic requirements of an athlete. In an alternative embodiment elements of the sole 615 and/or upper 620 can be formed in any appropriate open or closed structure, having any appropriate dimensions (e.g., shape and size), structure, material properties (e.g., density), to produce the specific performance and aesthetic requirements of an individual athlete.

In various embodiments any of the sensors and measurements described herein may be used to provide appropriate input parameters for customizing the shoe 610 as a whole, or the sole 615 and/or upper 620 alone (or limited regions thereof), depending upon the specific requirements of the athlete. Factors that the shoe can be customized for include, but are not limited to, the performance and technique of the athlete, the physical structure of the foot of the athlete, injury prevention and/or protection, weight considerations, support considerations, and/or aesthetic considerations. In one exemplary embodiment stress/strain gauges can be placed on an upper of a shoe of an athlete during the measurement of input parameters to identify regions of the upper that are subject to high and low stress/strain during the gait cycle of an individual athlete, with the algorithms and methods described herein using this information to identify regions of a customized upper for that athlete that require more support, and regions of the upper that do not require as much support (and can therefore be constructed from a lighter and/or more flexible material and/or material structure).

In an alternative embodiment stress/strain data can be gathered through the use of optical camera scanning (or other appropriate scanning or measurement techniques) of the foot/shoe during athletic motion, with markers on the foot/shoe providing identification of relative positioning of portions of the foot, and changes to that relative positioning over time. Analysis of changes in relative position can be used to calculate the stress and strain at each region of the shoe/foot during an athletic motion.

Another exemplary midsole that may be formed using methods and materials described herein can be seen in FIGS. 37A to 37D. In this embodiment, a midsole 500 is formed as a lattice or web-like structure with a plurality of elongate elements 505 extending between nodes (connection locations) 510. The distribution of elongate elements 505 and nodes 510 within the lattice structure may, in one embodiment, be determined by performance metric data obtained from the input parameters of a specific athlete (or group of athletes) and the selection criteria of that athlete (or group of athletes). Alternatively, the lattice structure may be created more generically to provide standardized support and performance requirements for a category of athletes. In this embodiment, the lattice structure (or volumetric mesh structure) is composed of a matrix including a series of tetrahedrons comprising hexagonal cells 705 which share adjacent elements. In this embodiment a structure is created by connecting the centerpoint of each face of the tetrahedron to the midpoint of each of the sides.

In various embodiments polyhedrons or any appropriate size shape and structural relationship may be utilized to form a lattice of cells providing a required level of support, flexibility, cushioning, and other structural, performance, and/or aesthetic parameters to different regions of a shoe sole, or portion thereof, based on performance and aesthetic considerations. Exemplary polyhedrons that may be used to create structural features of a midsole include, but are not limited to, tetrahedrons, truncated tetrahedrons, cubes, truncated cubes, dodecahedrons, truncated dodecahedrons, octahedrons, truncated octahedrons, higher order polyhedrons or truncated polyhedra, and/or prisms of any appropriate number of sides (e.g., triangular prisms, pentagonal prisms, hexagonal prisms, or higher order prisms). In one embodiment an entire midsole, or portion thereof, can be formed from a single polyhedral structure (with varying size, element thickness, etc. being used to impart different structural properties to different regions, if required). In another embodiment a plurality of differing polyhedrons may be incorporated into a single midsole (or portion thereof). Such structures may also be utilized to form other portions of a shoe (e.g., shoe uppers, or portions thereof) and/or athletic apparel, athletic protection/padding, and/or athletic equipment, or portions thereof.

Figure 37A:
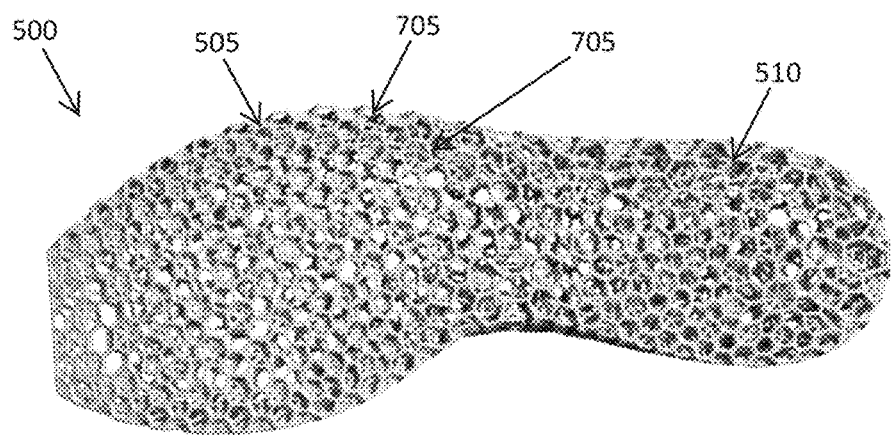
FIG. 37A is a bottom view of a midsole for an article of footwear having hexagonal cells, in accordance with one embodiment of the invention.
Figure 37B:
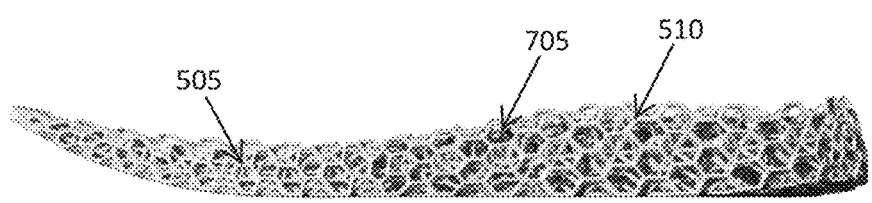
FIG. 37B is a side view of the midsole of FIG. 37A.
Figure 37C:
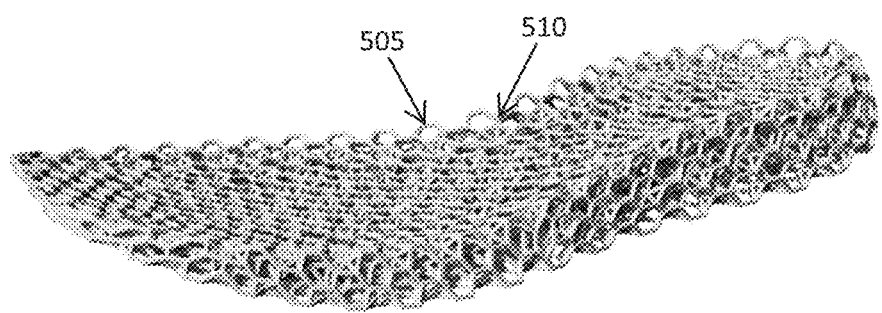
FIG. 37C is a perspective view of the midsole of FIG. 37A.
Figure 37D:
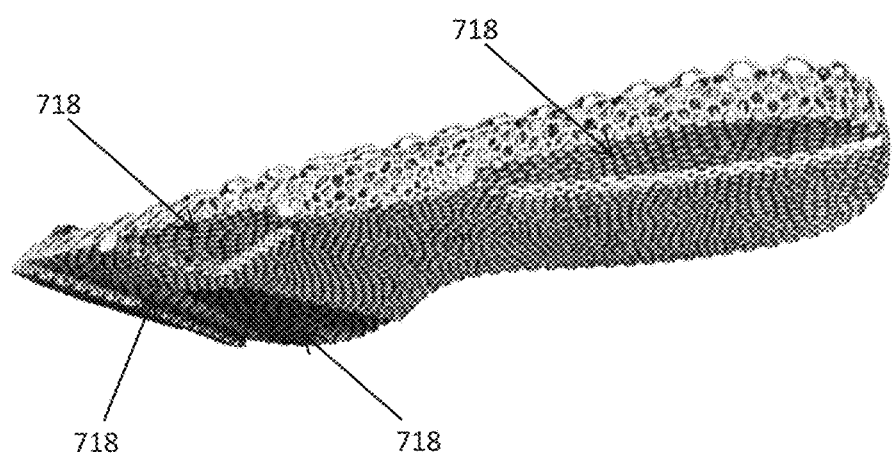
FIG. 37D is perspective view of the midsole of FIG. 37A with indentations in the bottom surface.

In one embodiment, as shown in FIG. 37D, the bottom (or lower) surface 560 of the midsole 500 may include one or more indents 718 into which ground contact elements (e.g., outsole elements) or other structural features may be placed. Other possible structural features may include, but are not limited to, cushioning elements, traction elements, protection elements (e.g., plates), flexion control elements, performance monitoring sensors, etc. In various embodiments one or more indents or cavities may be located at any portion of the midsole (e.g., within a central region, on an upper or lower surface, on a medial and/or lateral side, and/or in a forefoot, midfoot, and/or heel region) to provide a location for one or more structural features to be placed. In one embodiment traction elements may be constructed directly into the midsole, thereby wholly or partly negating the need for additional separate outsole elements.

Figure 38A:
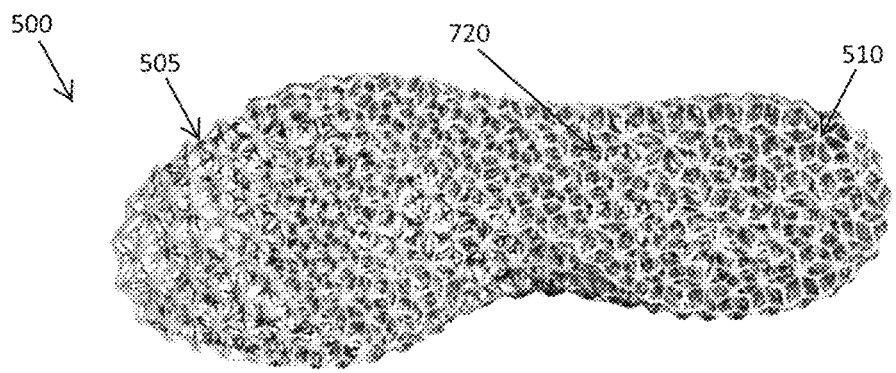
FIG. 38A is a bottom view of another midsole for an article of footwear, in accordance with one embodiment of the invention.
Figure 38B:
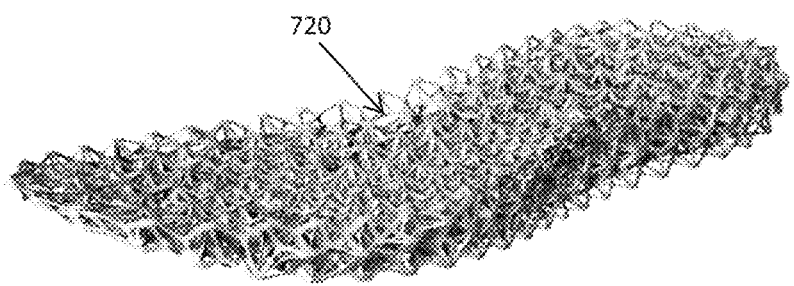
FIG. 38B is a perspective view of the midsole of FIG. 38A.
Figure 39A:
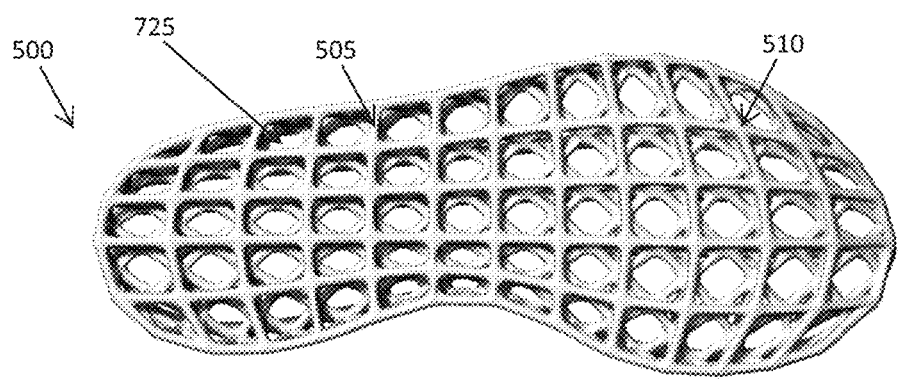
FIG. 39A is a bottom view of another midsole for an article of footwear, in accordance with one embodiment of the invention.
Figure 39B:
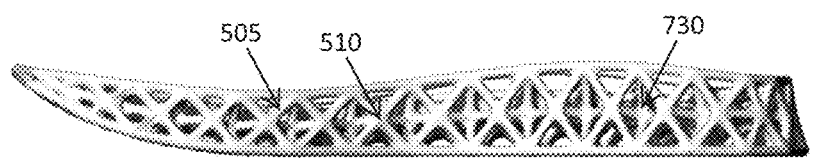
FIG. 39B is a side view of the midsole of FIG. 39A.

Another exemplary midsole formed using methods and materials described herein can be seen in FIGS. 38A and 38B. In this embodiment, a cell structure 720 is created by stemming elongate elements 505 from the center of tetrahedronal elements and joining them at nodes 510 at each corner. A further exemplary midsole, comprising square cells 725 forming a warped square grid alternating with a midlayer of polyhedral cells 730 is shown in FIGS. 39A and 39B.

Another exemplary midsole 500, as shown in FIGS. 40A and 40B, may be formed from a plurality of polyhedrons (in this case tetrahedrons) having circular elements 735 (or rings) forming the faces of the tetrahedrons. The size and thickness of these rings 735 can vary over the volume of the midsole 500 to impart different structural properties to different regions thereof. Another midsole formed from a plurality of polyhedrons (in this case cubes) having circular elements 735 (or rings) forming the faces of the cubes is shown in FIGS. 41A-42. In addition to size and thickness changes, the rings 735 can vary in shape (from circular to elliptical or other curved shapes of any appropriate geometry) to impart different structural properties to different regions thereof.

Figure 50:
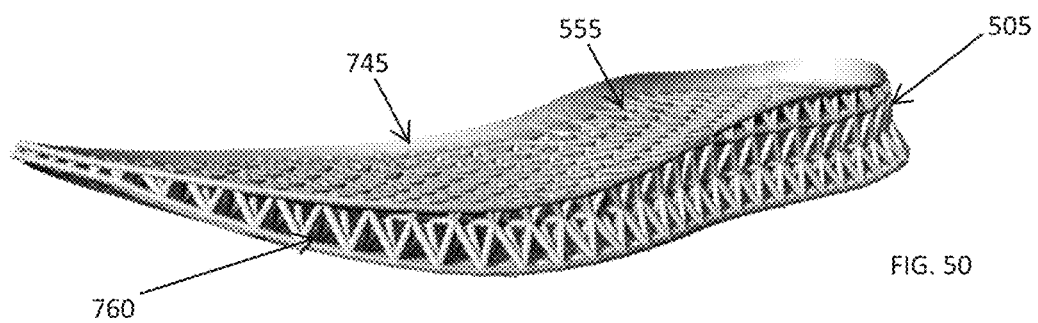
FIG. 50 is a perspective view of another midsole for an article of footwear having triangular cells, in accordance with one embodiment of the invention.

In one embodiment the lower surface 560 of the midsole 500 includes positioning elements 740 onto, or into, which ground contact elements (e.g., outsole elements) or other structural elements can be positioned and affixed. These can, for example, provide stable structures onto which the outsole elements can be permanently (or removably) affixed and held. In one embodiment one or more plates 745 can be integrally formed with (or affixed to) the midsole 500 to provide additional structure and support to the upper surface 555 and/or lower surface 560 midsole 500. An exemplary plate 745 covering the entire upper surface 555 of a midsole 500 is shown in FIG. 42, while a plate 745 comprising a band of material extending around an outer perimeter of an upper surface 555 of a midsole 500 is shown in FIG. 50. Plate 745 may provide cushioning and protection to the foot of a wearer and/or provide a solid surface onto which an upper of a shoe can be adhered or otherwise affixed to.

Figure 43A:
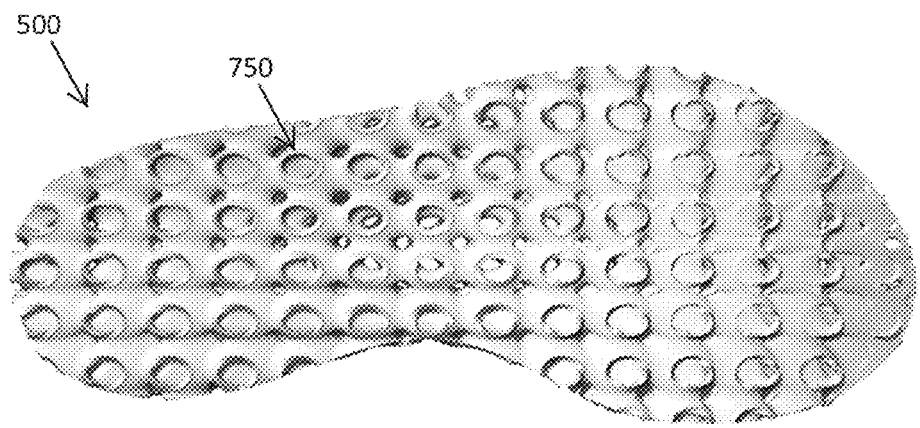
FIG. 43A is a bottom view of another midsole for an article of footwear, in accordance with one embodiment of the invention.
Figure 43B:
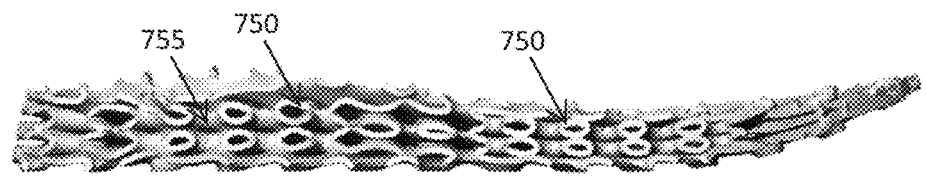
FIG. 43B is a side view of the midsole of FIG. 43A.
Figure 44:
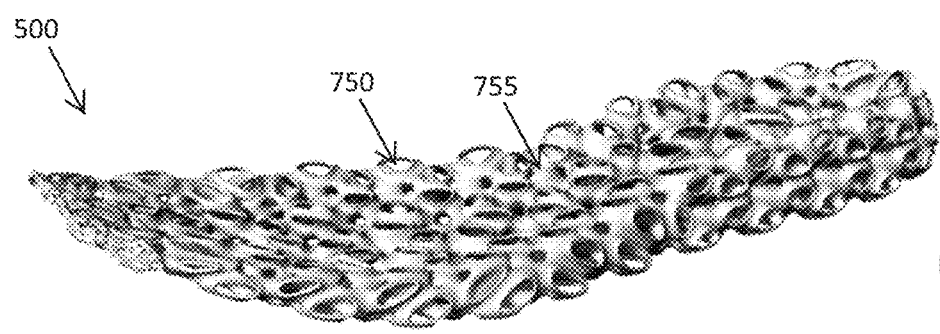
FIG. 44 is a perspective view of another midsole for an article of footwear, in accordance with one embodiment of the invention.
Figure 45:
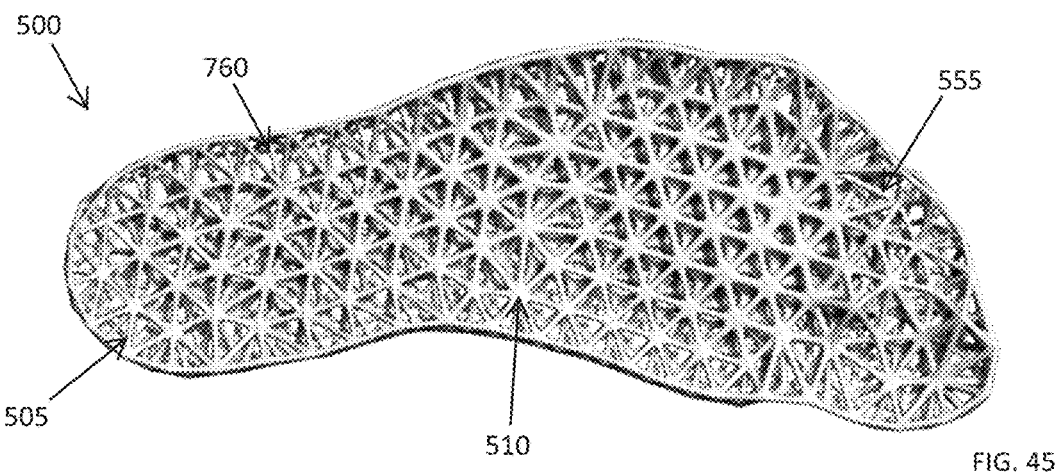
FIG. 45 is a top view of a midsole for an article of footwear following a shape of a foot, in accordance with one embodiment of the invention.
Figure 46:
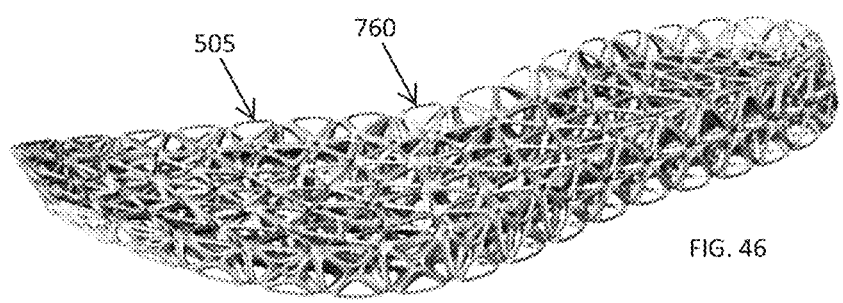
FIG. 46 is a perspective view of a midsole for an article of footwear having triangular cells, in accordance with one embodiment of the invention.
Figure 47A:
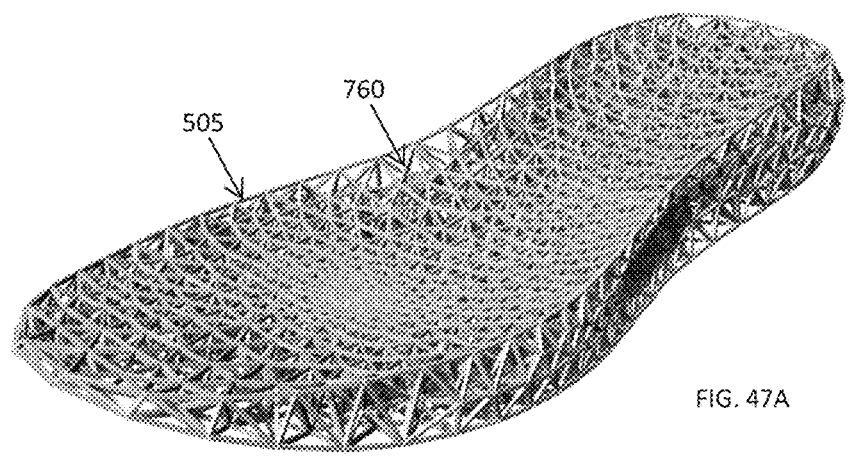
FIG. 47A is a perspective view of another midsole for an article of footwear having triangular cells, in accordance with one embodiment of the invention.
Figure 47B:
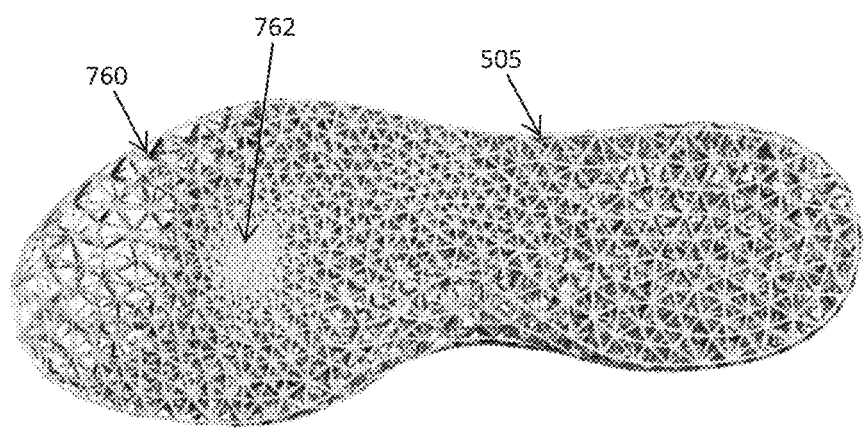
FIG. 47B is a bottom view of the midsole of FIG. 47A.
Figure 48:
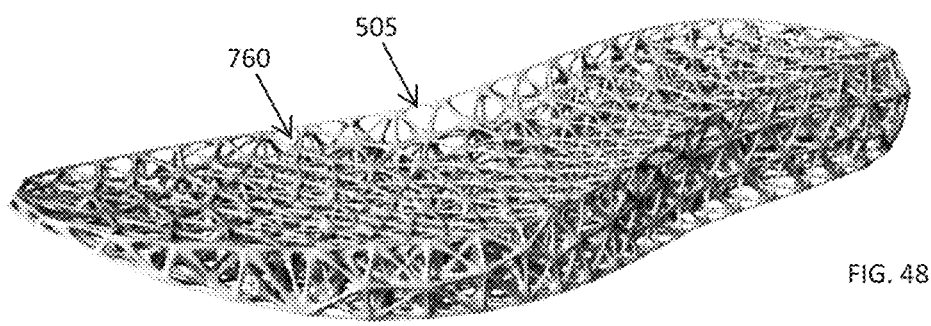
FIG. 48 is a perspective view of another midsole for an article of footwear having triangular cells, in accordance with one embodiment of the invention.
Figure 49:
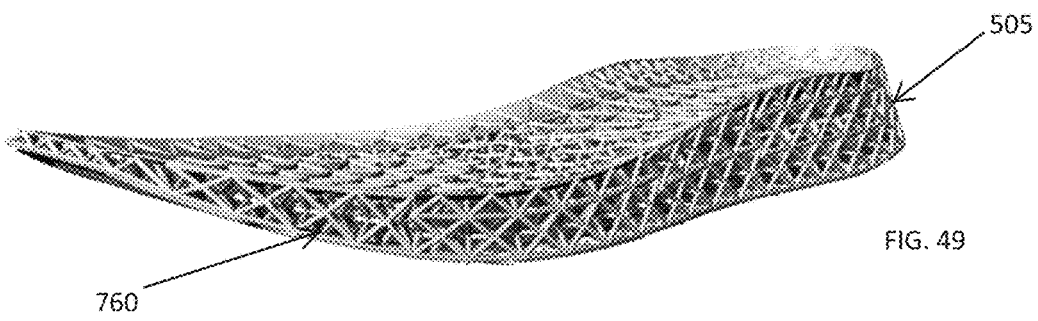
FIG. 49 is a perspective view of another midsole for an article of footwear having triangular cells, in accordance with one embodiment of the invention.

Another exemplary midsole, in accordance with one embodiment of the invention, is shown in FIGS. 43A and 43B. In this embodiment, elliptical shapes 750 are formed and joined together to form a midsole 500. Another embodiment, including a plurality of elliptical elements 750 located at the faces of tetrahedronal cells and joined together through shared wall structures 755 to form an open matrix of structural elements, is shown in FIG. 44.

In one embodiment cells in a midsole 500 can be formed from a plurality of adjoining triangular elements 760, as shown in FIGS. 45 to 50, with the triangular elements forming the faces of a matrix of tetrahedron-shaped structural elements. In various embodiments the triangles, or any other shape, may have sharp or rounded corners. In one embodiment elongate elements can be arranged in a substantially vertical arrangement in certain regions of the midsole 500 to provide additional structural stability (e.g., to reduce/prevent shearing during loading) to the midsole 500. In addition, as discussed above the size of the elongate elements 505 forming the cells can be varied over the midsole 500 with, for example, regions requiring greater structural support (such as under the forefoot of an athlete) having smaller cells 762 with shorter elongate elements 505 (as shown in FIG. 47B).

In one embodiment the shape of the midsole 500 can be based on scanned data of the foot shape of an athlete. An exemplary midsole 500 having an upper surface 555 substantially conforming to the shape of an athlete can be seen in FIG. 45.

In various embodiments the elongate elements may be straight or curved and may be of any appropriate length, thickness, and orientation to impart the required structural characteristics to regions of a midsole. The thickness may be constant or may vary over the length of the elongate element. The orientation of one or more elongate may be substantially vertical or at an acute angle to the vertical. The elongate elements may be angled in a substantially longitudinal direction (with respect to the direction of the shoe sole) or in a substantially transverse direction, or at any angle therebetween. For example, elongate elements may be arranged in an orientation opposing the direction of the predominant load placed on the midsole at that location during an athletic motion.

Figure 51A:
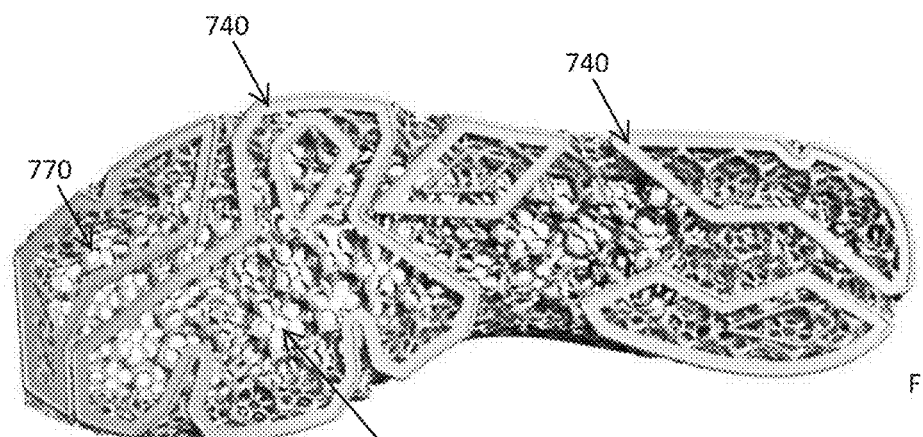
FIG. 51A is a bottom view of a midsole for an article of footwear having spheroid-based cells, in accordance with one embodiment of the invention.
Figure 51B:
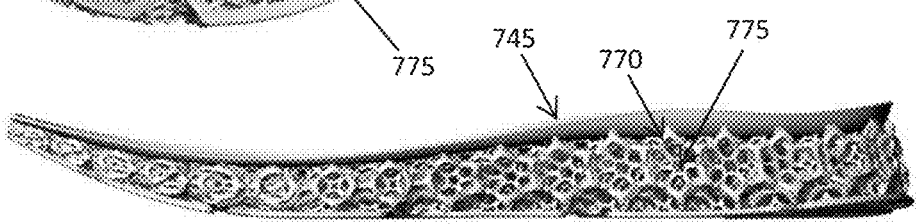
FIG. 51B is a side view of the midsole of FIG. 51A.
Figure 51C:
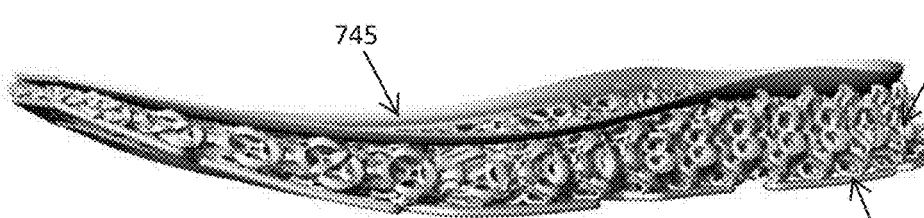
FIG. 51C is a perspective view of the midsole of FIG. 51A.
Figure 51D:
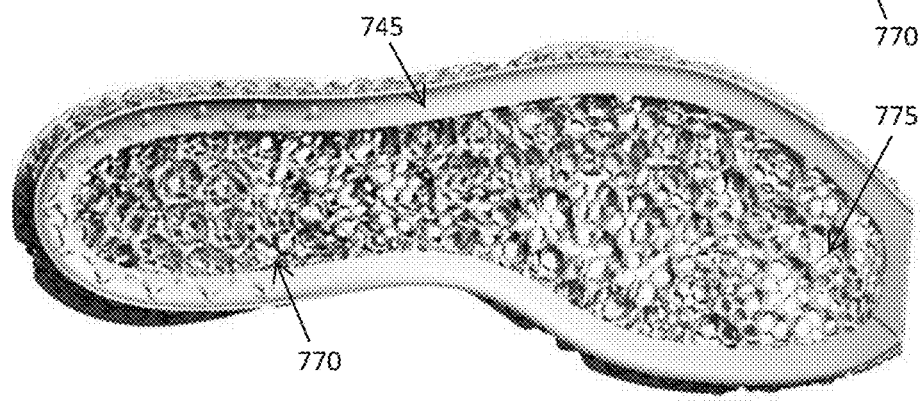
FIG. 51D is a top view of the midsole of FIG. 51A.
Figure 52:
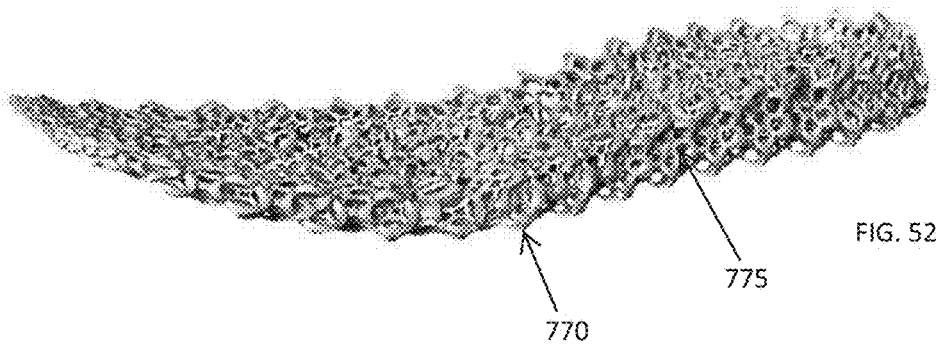
FIG. 52 is a perspective view of another midsole for an article of footwear having spheroid-based cells, in accordance with one embodiment of the invention.

In one embodiment, structural elements such as elliptical elements 770 may be arranged to form the faces of a larger structural cell such as, but not limited to, the spheroidal structure 775 shown in FIGS. 51A-52. In various embodiments elongate elements and/or elliptical elements may be arranged in any appropriate manner to produce a matrix of structural cells providing any appropriate structural characteristics to the midsole.

Figure 53:
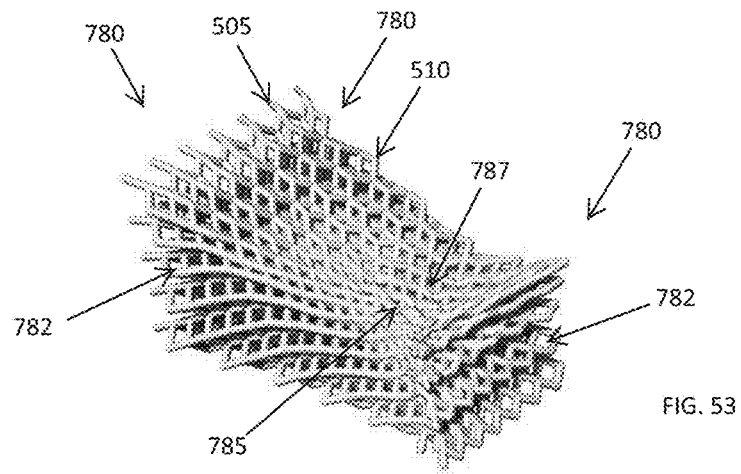
FIG. 53 is a perspective view of a warped matrix structure, in accordance with one embodiment of the invention.
Figures 54A, 54B:
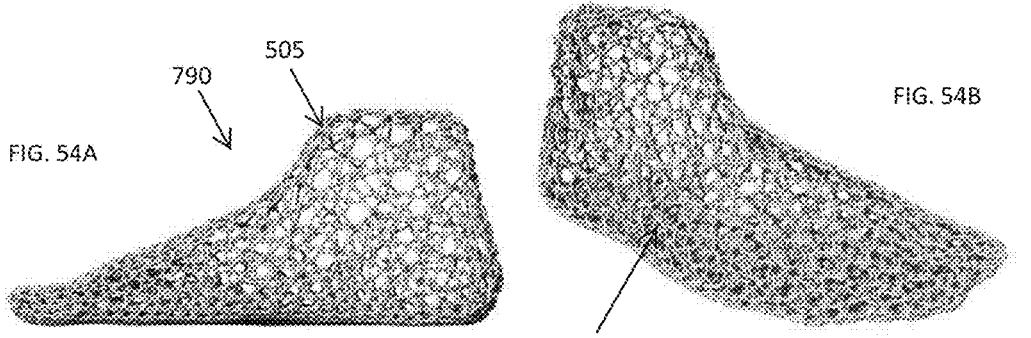
FIG. 54A is a side view of a foot-form formed using foot scan data, in accordance with one embodiment of the invention.
FIG. 54B is a perspective view of the foot-form of FIG. 54A.
Figures 55A, 55B:
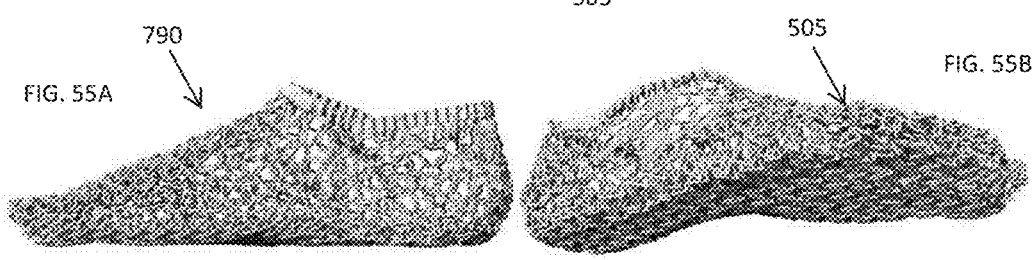
FIG. 55A is a side view of another foot-form formed using foot scan data, in accordance with one embodiment of the invention.
FIG. 55B is a perspective view of the foot-form of FIG. 55A.

Various embodiments of the midsole structures described herein can include a matrix of structural cells that is warped or otherwise adjusted to produce regions having differing densities, directional strengths, etc. to impart differing structural properties to different regions of the midsole. An exemplary warped matrix having regions of lower density 780 (formed by increasing the length of the elongate elements 505 and therefore increasing the size of the resultant cells 782) and a region of higher density 785 (formed by decreasing the length of the elongate elements 505 and therefore decreasing the size of the resultant cells 787) can be seen in FIG. 53.

Figures 56A, 56B:
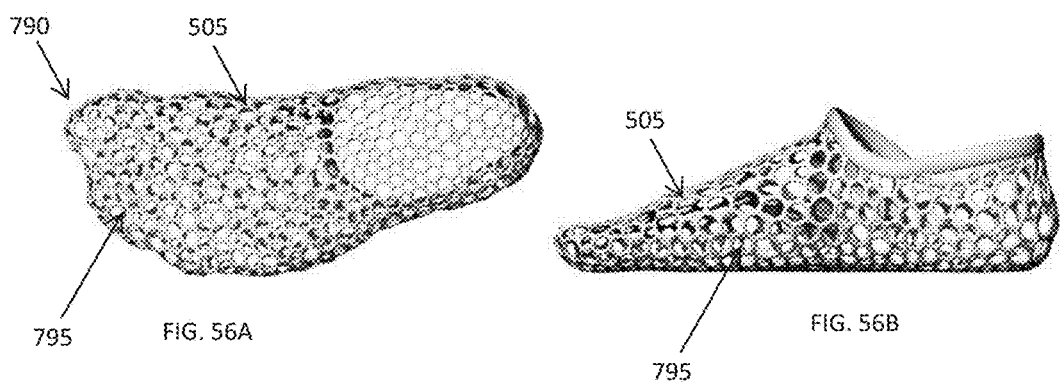

In one embodiment a lattice or matrix of elements can be used to form foot shapes which may be used, for example, to form uppers, or portions of uppers, for an article of footwear and/or form shoe lasts for use in the manufacture of footwear. These foot forms 790 may have a hollow interior or a structured, or partially structured, interior. Exemplary foot forms comprising a plurality of elongate elements 505 forming a chainmail-type structure are shown in FIGS. 54A to 55B, while a foot form comprising a plurality of elongate elements 505 forming a matrix of hexagonal and pentagonal cells 795 can be seen in FIGS. 56A and 56B. In alternative embodiments any appropriate structure, or combination of structures, may be utilized to form the foot forms.

In various embodiments these structures may be formed from substantially stiff and inflexible materials (for example when forming lasts for manufacturing purposes) or can be formed from flexible and/or elastic materials (for example when forming uppers, or portions thereof, for footwear). In one embodiment structures, such as portions of uppers and/or other shoe elements (e.g., sole elements or combines sole and upper elements), can be formed in a fully or partially collapsed or flattened state and thereafter expanded to form a finished part. This may be particularly beneficial, for example, in additive manufacturing, where forming objects in a collapsed state allows for greatly reduced volume requirements during manufacturing, thereby allowing significantly more parts to be manufactured in a single manufacturing run. In one embodiment the shoe element, or any other structure (e.g., protective apparel or padding, sports equipment, etc.) can be manufactured from flexible materials that elastically deform into a finished part after initial forming (e.g., by having an elastic deforming stress pre-formed in the formation structure to automatically deform upon construction, or upon release of the structure from the manufacturing mold, powder bed, etc.). Alternatively, or in addition, the structure could be formed from a material allowing for plastic deformation after initial formation to reshape the structure into a desired shape.

In one embodiment a structure (e.g., a shoe sole and/or upper) can be formed, for example through additive manufacturing techniques, with one or more hinges or other deformable structural elements to allow the part to be formed in a bent or collapsed state and thereafter deformed to create the finished structure. In another embodiment a structure could be formed with an interior cavity into which a bladder can be placed to "inflate" the structure to a finished size after initial formation in a collapsed state.

In one embodiment a midsole 800 for an article of footwear may be formed from a plurality of independent structural elements 805 connected through a plurality of linkage elements 810. An exemplary linkage system, and a midsole 800 formed from a plurality of structural elements 805 and linkage elements 810, can be seen in FIGS. 57 to 58E. In this embodiment, the linkage elements 810 may be flexible, elastically or plastically deformable, and/or provide some degree of give within the structural elements 805 (e.g., by being loose enough to allow relative movement between adjacent structural elements 805) to provide the midsole 800 with a controlled degree of flexibility and manipulability.

The structural elements 805 are formed as hollow-walled elements having openings into which the linkage elements 810 extend. The linkage elements 810 are formed as bent elongate elements that extend between adjacent structural elements 805 to form a chainmail-type linkage arrangement. In alternative embodiments the structural elements 805 and linkage elements 810 may take any appropriate form, and any appropriate form of structure providing connected relative movement between adjacent structural elements may be utilized. In one embodiment the structural elements 805 may be formed as a unitary structure with the linkage elements 810. In another embodiment the structural elements 805 and linkage elements 810 can be separate interconnected elements. The structural elements 805 and linkage elements 810 may be utilized to form a sole and/or upper of a shoe, or portions thereof, or a portion of athletic apparel, athletic equipment, or protective equipment/padding.

In one embodiment the size and shape of the structural elements 805 and/or linkage elements 810 may vary such that different regions of the midsole 800 have structural elements 805 with different shapes, sizes, and/or structural characteristics. For example, the embodiment of FIGS. 58A to 58E includes a toe section 815 having smaller structural elements 805, a forefoot region 820 having larger structural elements 805, and a midfoot region 825 and heel region 830 having intermediate sized structural elements 805, with the change in size allowing for four structural elements 805 to span the width of the midsole throughout the entire length thereof. In alternative embodiments any appropriate number of elements may span the width of the structure, and the number and arrangement of elements may change over a length and/or width thereof.

Providing relative motion between structural elements 805 allows for the midsole 800 to be manipulated after formation to allow for adjustment of the shape and size of the midsole 800 to allow a single structure to fit multiple sizes and shapes of foot. For example, a midsole 800 that can expand and contract in width and/or length can be adjusted to fit multiple shoe sizes. As shown in FIGS. 58B and 58C, a midsole 800 can be adjusted to have a first length L(1) and width W(1), thereby fitting a first shoe size, or be spread apart to provide a second length L(2) and width W(2), thereby fitting a second shoe size. Allowing for this adjustment would allow for a single structure to cover a vast array of different foot sizes, widths, and shapes.

In addition, allowing for relative movement of the structural elements 805 allows for the midsole 800 to be manufactured in a first configuration (e.g., flat, as shown in FIG. 58D) and thereafter be reshaped into a final, curved configuration (e.g., curved along at least a portion of the longitudinal extent, as shown in FIG. 58E). This may be particularly beneficial, for example, in additive manufacturing, where forming the midsole 800 in a flat state (and only adding curvature to the structure after forming) potentially allows for greatly reduced volume requirements during manufacturing, thereby allowing significantly more parts to be manufactured in a single manufacturing run.

The midsole 800 can be locked into a finished shape by any appropriate method. For example, the midsole 800 can be shaped into a desired form and thereafter treated by any appropriate chemical or heat treatment to fuse the structural elements 805 and linkage elements 810 into a locked arrangement. Alternatively, or in addition, a foam, adhesive, or other material can be infused into the midsole 800 to hold the midsole 800 in its desired shape.

Exemplary sole elements (in this case outsole plates) having cleated traction elements for use, for example, in soccer, American football, rugby, or other sports requiring cleats, are shown in FIGS. 59A to 59E. In these embodiments the size, shape, and arrangement of the cleated traction elements 850 on the outsole plates 855 can be arranged in any appropriate manner to provide the required structural, performance, and/or aesthetic properties required by the wearer. In one embodiment the positioning, orientation, and structural characteristics of the cleated traction elements 850 can be customized to the requirements of an athlete based on utilization of the methods and systems described herein.

Figure 59A:
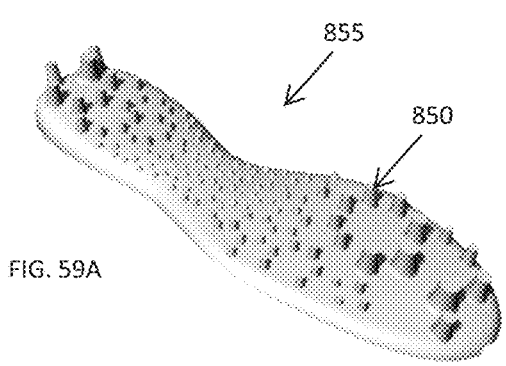
Figure 59B:
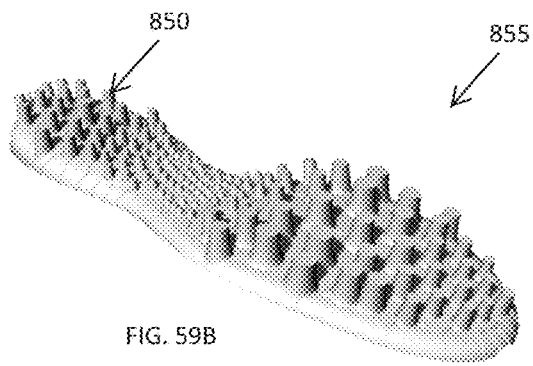
Figure 59C:
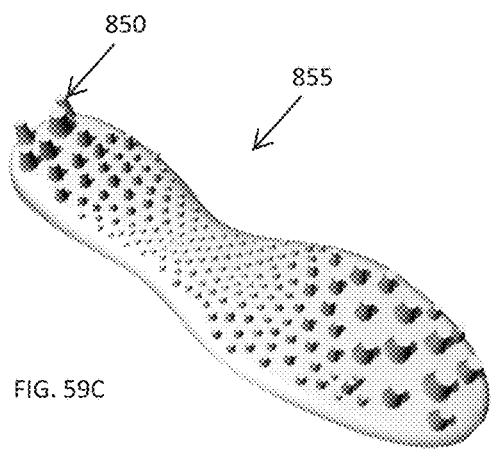
Figure 59D:
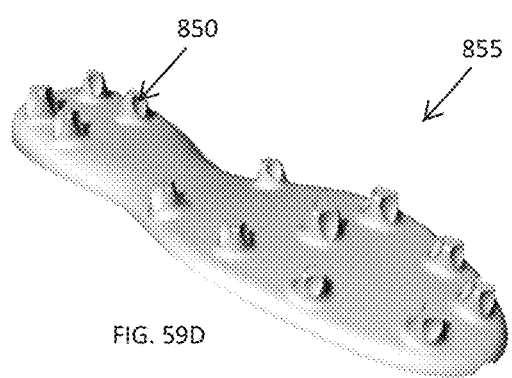
Figure 59E:
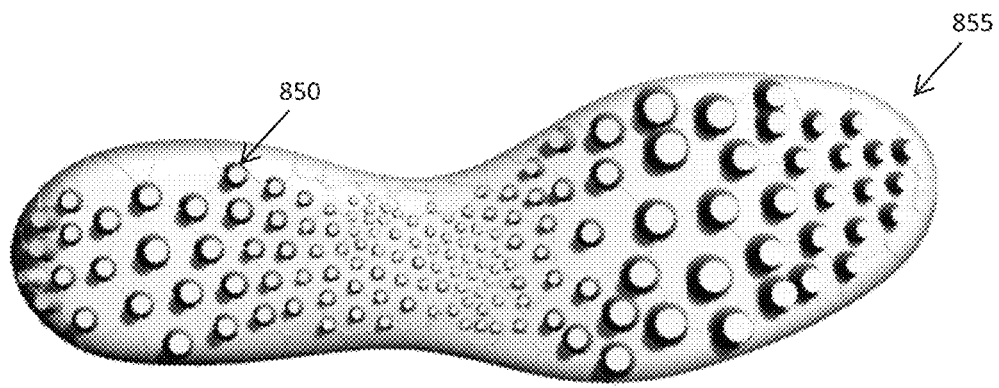

In one embodiment the cleated traction elements 850 may be substantially circular in cross section, as shown, for example, in FIG. 59E. Alternatively, the cleated traction elements 850 may be ribbed to produce a plurality of extensions out from a central core, as shown, for example, in FIG. 59D (which shows cleated traction elements 850 having a 3-sided ribbed structure). In alternative embodiments any appropriate cross-sectional cleat shape may be utilized including, but not limited to, elliptical cleats, bladed cleats, or triangular cleats. These cleats may or may not be tapered and may extend at substantially 90 degrees or at an acute angle from the base plate.

In one embodiment a sole structure (e.g., an outsole plate or a midsole element) may incorporate one or more flex grooves to provide controlled flexibility within certain regions of the sole structure. For customized footwear the positioning of these flex grooves may, for example, be based on the scanned foot data and/or performance data of an athlete.

An outsole plate 855 for a cleated sole structure having flex grooves 860 is shown in FIGS. 60A to 60E. The flex grooves 860 divide the outsole plate 855 into a plurality of regions: a medial forefoot region 865, a lateral forefoot region 870, a medial midfoot region 875, a lateral midfoot region 880 which extends into a lateral heel region 885, and a medial heel region 890. In alternative embodiments any appropriate arrangement of segregated regions may be utilized depending upon the physiology of the athlete, the performance requirements of the shoe, and/or aesthetic considerations.

Figure 60A:
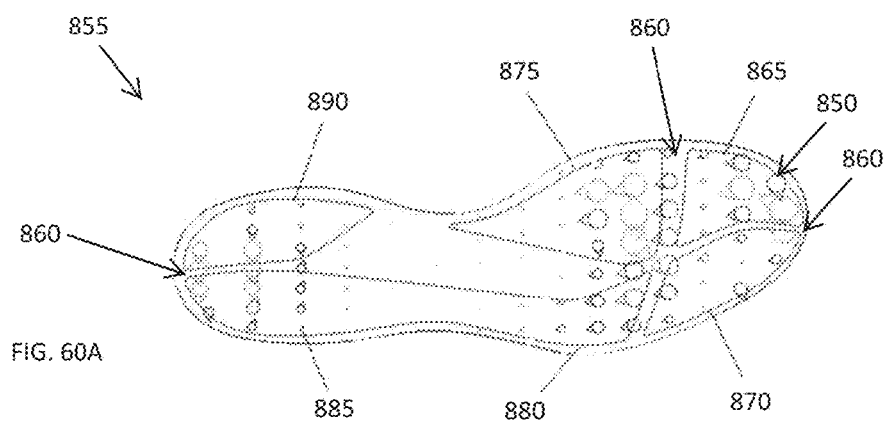
Figure 60B:
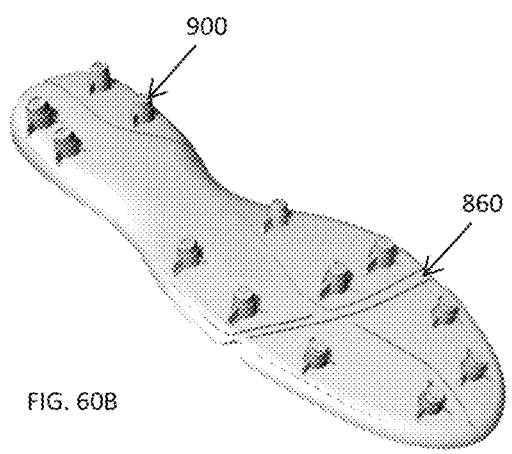
Figure 60C:
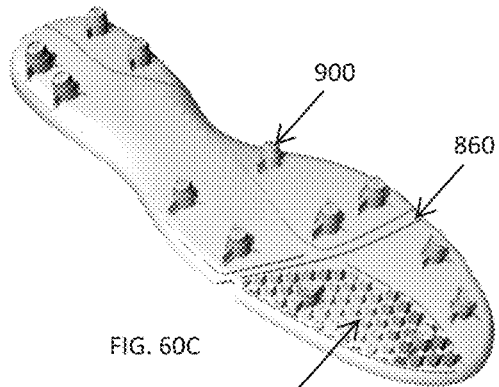
Figure 60D:
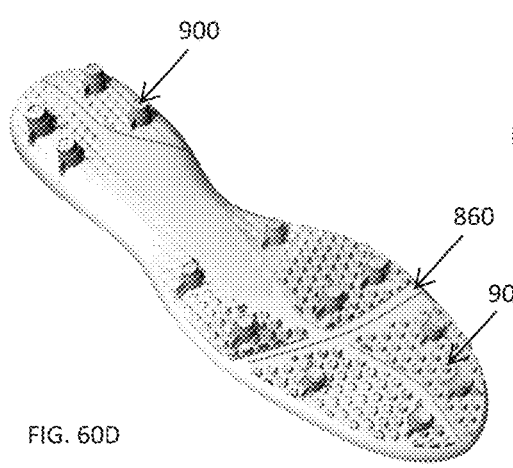
Figure 60E:
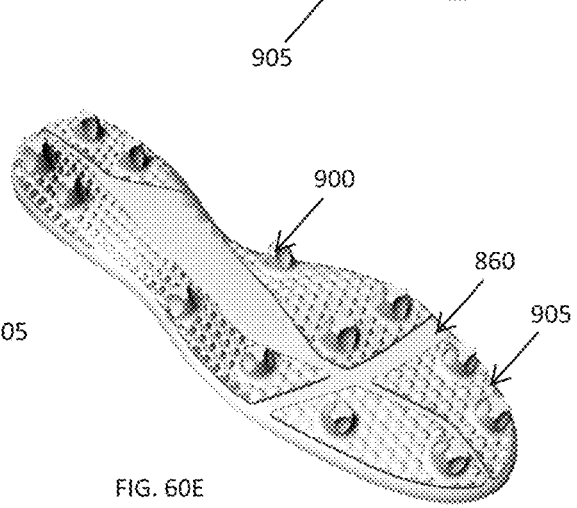

In one embodiment the traction elements can be divided into primary traction elements and one or more set of secondary traction elements, with one or both of the primary and/or secondary traction elements positioned, sized, and/or shaped based on biometrical and/or performance data from an athlete. FIGS. 60B through 60E show a variety of different outsole plates 855, with FIG. 60B showing a plate having only primary traction elements 900 and FIGS. 60C through 60E showing various configurations of primary traction elements 900 and secondary traction elements 905. FIG. 60E also shows a different shape of primary traction element 900 from those utilized in FIGS. 60B through 60D.

In one embodiment performance and/or biometric information can be utilized to produce a grid of polygonal shapes into which customized cleats can be positioned based on measured and processed athlete data. An exemplary outsole plate 855 having a mapping/grid structure 910 superimposed thereon can be seen in FIG. 61A. In this embodiment the edges 915 of the grid elements corresponds to the edges of cells 925 into which cleated traction elements 920 may be positioned on the outsole plate 855. The size (e.g., height) and shape of the cleated traction elements 920 may be based on processing of the performance and/or biometric information from the athlete, as described herein.

As described herein, various means of processing athlete data can be utilized in calculating customized traction element structures and positions for a specific athlete. A number of exemplary processing methods for use, for example, in cleated traction elements are shown in FIGS. 62A to 62D. These figures show the different traction element configurations that can be created from a single data set depending on specific filtering, processing, and other analysis tool selections.

Figure 62A:
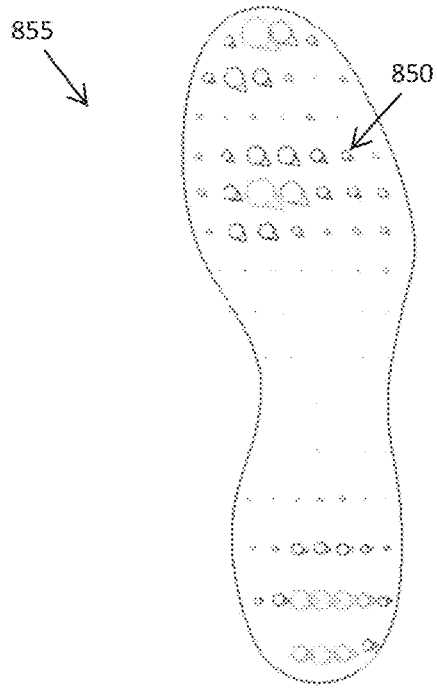
Figure 62B:
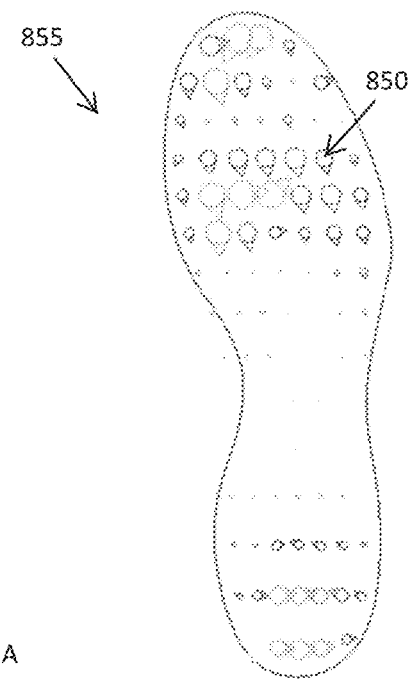
Figure 62C:
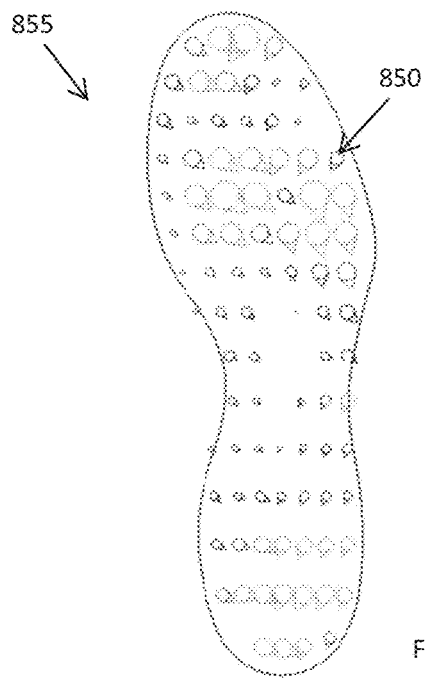
Figure 62D:
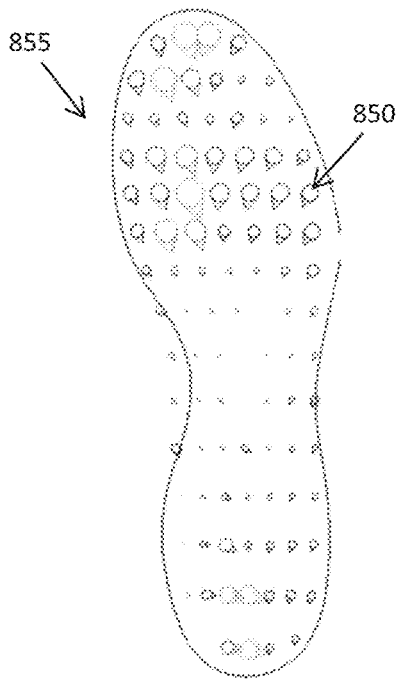

FIG. 62A shows an arrangement of cleated traction elements 850 on an outsole plate 855 based on a direct averaging and simple weighting of all data throughout the course of an athletic motion. FIG. 62B shows an arrangement of cleated traction elements 850 on an outsole plate 855 based on a filtered data set, with only the largest 10% of data samples at a given location being used to create a cleated traction element 850 configuration at that location. FIG. 62B shows an arrangement of cleated traction elements 850 on an outsole plate 855 based on a zonal approach to data processing, with the data in different regions (or zones) of the outsole plate 855 processed independently based upon an identification of the dominant performance requirements for each region (e.g., longitudinal or lateral support, landing or toe-off support, etc.). FIG. 62D shows an arrangement of cleated traction elements 850 on an outsole plate 855 based on a weighted filtering of the zonal data of FIG. 62C with data from points proximate a point of interest being used to smooth the data transition between regions. In alternative embodiments any other appropriate processing and analysis techniques may be utilized, as appropriate.

An exemplary method of designing an outsole plate 940 with cleated traction elements 945 is shown in FIGS. 63A to 63G. In this embodiment, biometric and performance data are gathered for an athlete and used to determine preferred cleat 945 location, size and shape over the surface of an outsole plate 940 for a shoe such as a soccer shoe/boot. The data can also be used to determine a preferred structure for the plate 940 to provide superior flexibility, support, and stability customized to the athlete.

In the embodiment of FIGS. 63A to 63G the data used in the customization design process include biometric data relating to the geometry of the athlete's foot (e.g., foot scan data 950 obtained through an optical scan of the geometry of the foot). In addition, pressure data 955 associated with the pressure distribution under the foot during an athletic motion and force vector data 960 associated with the directions and magnitudes of the force between the foot and the ground during an athletic motion are used to provide cleat configurations specifically tied to the athlete. In alternative embodiments, additional and/or different biometric and/or performance data can be used in the customization process.

In one embodiment the athlete can perform a number of different athletic motions (e.g., straight line running, curved running, jumping, cutting, turning, kicking, etc.), with all these different data sets being incorporated into the data processing algorithm. The data for different motions can be weighted based on the dominance of a specific motion to the athlete's performance and/or to athlete preference. For example, one athlete (e.g., a soccer player) may want or need a shoe that is specifically designed to maximize straight line speed, while another athlete may want or need a shoe designed to enhance cutting speed and/or stability. The data can also be weighted or otherwise filtered to ensure that the results don't over-rely on one data set and motion to the detriment of other data sets and motions, thereby creating a shoe that provides customized support over a broad range of motions.

Figures 63A, 63B, 63C, 63D:
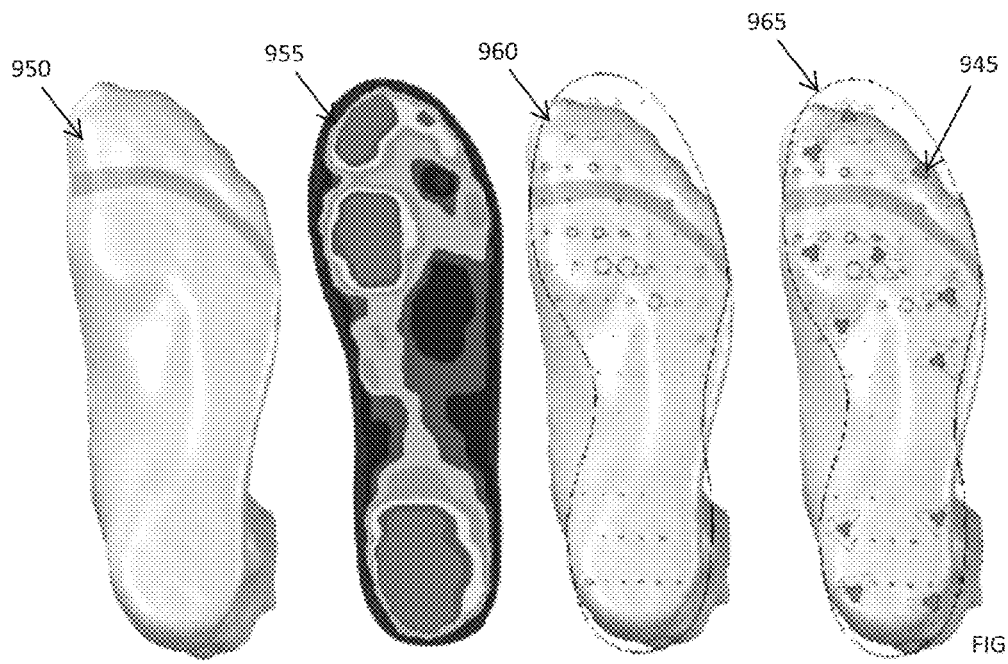
Figures 63E, 63F, 63G:
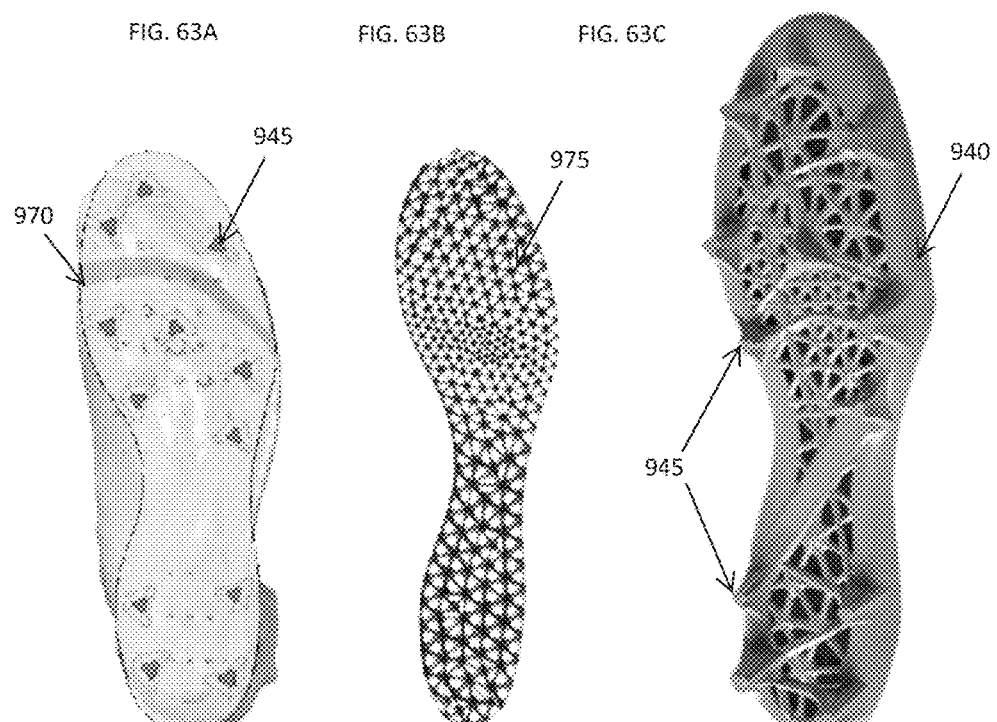

The processed data are then used to create a matrix 965 of desired cleat 945 locations, sizes, and directional orientations, as shown in FIG. 63D. This data can then be further processed to determine locations on the outsole plate 940 where greater or lesser degrees of flexibility (e.g., longitudinal, lateral, and/or torsional flexibility) are desired, where greater or lesser degrees of stiffness are desired, where greater or lesser degrees of structural support are required, and where greater or lesser degrees of protection are required. This data can then be used to create a unitary multi-component structure providing both customized traction control and structural support for the athlete. For example, the data can be used to create a primary lattice component 970 including a customized matrix of traction elements (as shown in FIG. 63E) and a secondary lattice component 975 including a lattice or web of support structures designed to provide customized flexibility, rigidity, structural support, and protection (as shown in FIG. 63F). These two lattice components can then be combined to create a final outsole plate 940 design providing a structure specifically adapted to the performance and biometric needs of an athlete.

In various embodiments any appropriate combination of traction elements, flexibility elements (e.g., flex grooves), support elements, etc. can be incorporated into a shoe element. The elements can be customized to a specific athlete (based on analysis of that athletes biometric and performance data) or be designed to provide a more generic, averaged, structure based on analysis of multiple athletes performing a specific athletic motion or range of motions.

In one embodiment traction elements may be formed as substantially hollow structures to reduce the material required for manufacture and to reduce the weight of the plate. An exemplary sole plate 978 for a cleated shoe having a plurality of hollowed cleated traction elements 980, with a web of structural stability elements 985 extending within the hollowed interior 990 of each cleated traction elements 980, is shown in FIGS. 64A and 64B. The structural stability elements 985 may be used to provide structural support for the cleated traction elements 980 and may take any appropriate form. In an alternative embodiment the hollow cleated traction elements 980 may be sufficiently structurally stable and solid on their own, thereby negating the need for structural stability elements 985. In one embodiment a material (e.g., a foam, a rubber, or another appropriate material) may be inserted into the hollow cleated traction elements 980 to provide stability to the element and/or to provide cushioning and/or other structural benefits to the sole plate 978.

The customized footwear elements described herein can be manufactured through any appropriate manufacturing technique such as, but not limited to, injection molding, blow molding, or using rapid manufacturing (additive manufacturing) technology such as, but not limited to, selective laser sintering (SLS), fused deposition modeling, stereolithography, laminated object manufacturing, inkjet-based additive manufacturing, or any appropriate computer controlled manufacturing technique including the layered addition/deposition of material.

In one embodiment the customized footwear components described herein can be manufactured through the use of SLS manufacturing methods and tooling. SLS is an additive manufacturing technique that uses a high power laser (e.g., a carbon dioxide laser) to fuse small particles of plastic, metal (direct metal laser sintering), ceramic, or glass powders into a mass that has a desired three-dimensional shape. The laser selectively fuses powdered material by scanning cross-sections generated from a 3-D digital description of the part (for example from a CAD file or scanned data) on the surface of a powder bed. After each cross-section is scanned, the powder bed is lowered by one layer thickness, a new layer of material is applied on top, and the process is repeated until the part is completed. SLS manufacturing allows for the formation of parts using various plastics, ceramics, and/or metals. Exemplary materials that may be used in the manufacture of footwear components include, but are not limited to, polymers, and for exemplary semi-crystalline polymers such as, but not limited to, nylon (amide), TPU, polyether block amide (PEBA), and/or polyester. Other materials may include, or consist essentially of, shape memory plastics, thermoplastic elastomers (TPE's) such as styrene-butadiene-styrene (SBS), ethylene vinyl acetate (EVA), and/or rubbers such as butadiene rubber. Exemplary metals include materials such as, but not limited to, aluminum, titanium, stainless steel, nickel alloy, cobalt-chrome, maraging steel, shape memory alloys (such as, but not limited to, nickel titanium), or other alloys. In one embodiment additional filler materials such as, but not limited to, nylon or carbon fiber or glass fiber, can be added to the base material to modify the properties of the finished part. Exemplary thermoplastic materials for use in SLS additive manufacturing, and methods of manufacturing parts using these materials, are disclosed in U.S. Pat. No. 6,110,411 to Clausen et al. and U.S. Pat. No. 8,114,334 to Martinoni et al., the disclosures of which are incorporated herein by reference in their entireties.

SLS provides a rapid means for manufacturing components without the need to create a mold for the component through the forming of a three-dimensional article in a layer-wise fashion by selectively projecting a laser beam having the desired energy onto a bed of particles of a selected material. In addition, SLS allows for the creation of complex unitary structures that cannot be manufactured through traditional molding techniques. For example, an outsole including integrated traction elements with undercut sections would be extremely difficult to manufacture through traditional injection or blow molding manufacturing processes, but is easily manufactured using SLS or other additive manufacturing methods. An exemplary SLS machine that may be utilized to manufacture customized parts, in one embodiment of the invention, is a P 395 Selective Laser Sintering System manufactured by EOS GmbH Electro Optical Systems of Krailling, Germany.

Other advantages of utilizing rapid manufacturing techniques such as SLS is the ability to create structures having different layers of different materials allowing, for example, for an outsole structure with a base plate of a first material and integrated traction elements of a second material. In addition, by carefully controlling the properties of the laser utilized in SLS manufacturing, such as the laser power and the speed of the scanning track of the laser, the density and other structural properties of the material used to construct the customized part can be carefully controlled over different regions of the structure. This allows, for example, for a lower density (and therefore lighter and more flexible) base plate with traction elements of a higher density (and therefore increased strength and stiffness). This also allows for different sections of a single structure (e.g., different traction elements within a single structure and/or different sections within a single base plate) to be formed with different density, strength, and/or stiffness properties.

SLS manufacturing also provides a significantly faster method of manufacturing customized footwear elements than traditional molding techniques, at least because there is no need to manufacture a mold prior to forming the customized footwear elements themselves. In one embodiment an entire customization process, from obtaining the input parameters through to providing a finished part for an athlete, can be carried out in only a few hours, or possibly less. As a result, SLS manufacturing, and other relevant additive manufacturing (or 3D printing) techniques provide an effective method of manufacturing both customized parts and/or parts (whether customized or designed for a broad range of users) having a structure that would be difficult or impossible to manufacture using traditional molding techniques.

In one embodiment additional materials, such as, but not limited to, pigmentation and/or UV stabilizers may be added to the powdered material utilized in the additive manufacturing process to provide colored parts and/or parts that are protected from changes in color (e.g., fading or yellowing) upon exposure to UV light over time. The pigmentation, UV stabilizer, and/or other additives may be added during extrusion of the material prior to powderization of the material or be added to the powdered material in liquid or powdered form. In an alternative embodiment color can be added to the structure through spray coating, dip coating, or any other appropriate coating technique after formation of the part. The color may be provided by any appropriate paint, ink, or other coloring agent(s) or chemicals(s).

Other additives that could be added during the manufacturing process may include, but are not limited to, antioxidants, antistatic agents, and/or whitening agents (e.g., fluorescent whitening agents). Exemplary antioxidants may include, but are not limited to, aromatic amines, phenols, phosphites and phosphonites, thiosynergists, hindered amine stabilizers, hydroxyl amines, benzofuranone derivatives, and/or acryloyl modified phenols. Exemplary antistatic agents may include, but are not limited to, fatty acid esters, ethoxylated alkylamines, diethanolamides, and/or ethoxylated alcohol. Exemplary fluorescent whitening agents may include, but are not limited to, bis-benzoxazoles, phenyl-coumarins, and/or bis-(styril)biphenyls.

In one embodiment a flow agent such as, but not limited to, a powdered Cab-O-Sil® fumed silica (e.g., Cab-O-Sil® PS 530, fumed silica, available from Cabot Corporation of Two Seaport Lane, Suite 1300, Boston, Mass. 02210, USA) can be added to the powdered material to improve the flowing of the material during depositing of the material in the powder bed within the additive manufacturing system, as described, for example, in U.S. Pat. No. 6,110,411 to Clausen et al. the disclosure of which is incorporated herein in its entirety.

In one embodiment the part may be formed from a material that chemically reacts with another material upon exposure thereto to swell or foam to an increased final size after formation. For example, the part may be formed from a material that swells upon exposure to a liquid (e.g., water) so that, after formation in a reduced state, the part can swell to its finished state by exposure to the liquid.

In one embodiment a blowing agent may be added to the manufacturing material (either during extrusion or during or after powderization of the raw material(s)). As a result, a part can be formed through additive manufacturing that includes a blowing agent designed to foam and expand the part upon exposure of the part to controlled conditions (e.g., controlled heat and pressure conditions), for example within a post-processing mold or oven. As a result, parts can be formed through additive manufacturing in a reduced size, with the blowing agent within the part thereafter activated to produce the finished, foamed part. This can allow for the forming of objects through additive manufacturing techniques in a reduced size that allows for greatly reduced volume requirements during manufacturing, with the parts thereafter expanded to their desired size through activation of the blowing agent(s), thereby allowing significantly more parts to be manufactured in a single manufacturing run. Foaming of the parts by activation of a blowing agent after formation of the part through additive manufacturing can also create parts having different structural properties (e.g., reduced density, increase cushioning, etc.) than can be formed through additive manufacturing alone. The blowing agent may include, or consist essentially of, any appropriate type of physical blowing agent known to those of ordinary skill in the art such as, but not limited to, nitrogen, carbon dioxide, hydrocarbons (e.g., propane), chlorofluorocarbons, noble gases and/or mixtures thereof. In one exemplary embodiment, the blowing agent comprises, or consists essentially of, nitrogen. Exemplary blowing agents, and methods of use, are described in U.S. Patent Publication No. 2012-0196115 A1, the disclosure of which is incorporated herein by reference in its entirety. An exemplary blowing agent for use with the methods and systems described herein is an endothermal blowing agent such as, but not limited to, Kycerol 91 or Kycerol 92, formed from modified sodium bicarbonate. Another exemplary blowing agent that may be used comprises thermo-expandable microcapsules with a liquefied blowing agent (e.g., a liquefied hydrocarbon) encapsulated by a shell layer (e.g., an acrylic copolymer. An exemplary of such a blowing agent is Cellcom-CAP/170K.

The use of SLS or other additive manufacturing techniques allows for the formation of unique structures, and combinations of structures, that would be difficult or impossible to create using traditional manufacturing techniques. Such structures may, for example, include a plurality of separate elements that are formed in an integrated state, at the same time, during SLS manufacturing to produce an interlocked multi-component structure (such as the midsole with the structural elements and linkage elements shown in FIGS. 58A to 58E). An exemplary structure, including a shoe 994 having an upper 995 with a plurality of sole elements 996 formed within the interior 997 the upper 995 is shown in FIG. 65. In this embodiment the sole elements 996 include a plurality of traction elements 998 that extend through openings 999 in the upper 995 to form a ground contacting surface for the shoe 994.

In one embodiment, utilization of SLS manufacturing allows for input parameters to be measured or selected remotely (e.g., at an athletic facility, in a store, or even at home), with the input parameters analyzed either remotely or at the users location (using a design program adapted to allow a user to design a footwear component themselves using the input parameters and various selection criteria) or analyzed at a manufacturing facility upon receiving input parameter data from a user/athlete. The analysis tools may include an algorithm for converting the design based on the performance metrics and user preferences into a computer readable file (e.g. a CAD file) that can be sent directly to an SLS machine to form the customized part. The analysis tool may, for example, include a program or application (App) that can be stored on a PC or portable electronic device and can send input parameters, user selection criteria, performance metric information, and/or final design information over a wireless or wired network to a manufacturing tool for construction of the customized footwear components. As a result, an athlete can create a customized design remotely, send that design to a manufacturing tool, and have the part manufactured and sent back to the user in short order. Measurement tools (e.g., measuring devices such as pressure sensor arrays and/or body scanning and/or measurement tools) can be located at shoe stores, at an athletic facility or event, and/or at home, while manufacturing tools (e.g., SLS machines) can be located at shoe stores, at an athletic facility or event, and/or at remote manufacturing locations. Alternatively, users can utilize portable consumer additive manufacturing tools to build customized footwear elements at home.

In one embodiment the part, or parts, formed through the manufacturing process and, for exemplary, through SLS, can be post-processed to provide additional aesthetic and/or structural characteristics. Such post-processing may include painting the part and/or coating the part with a material that supports or modifies the structural characteristics of the part, infusing the part with one or more materials, filling cavities in the part with one of more materials, and/or encasing the part in a covering material.

In one embodiment of the invention, rather than providing individually customized footwear for each individual athlete a plurality of predetermined footwear options can be provided with an athlete choosing the most appropriate option depending upon his/her specific needs and characteristics. For example, multiple data sets of athlete data (e.g., pressure and force data) can be categorized into a number of predetermined categories, with the categories determined by characteristics such as, but not limited to, footstrike location (e.g., heel striker, midfoot striker, or forefoot striker), level of pronation/supination, straight running or curved track running, etc. In this embodiment the athlete can select a pre- or post-manufactured "customized" shoe based on which category, or categories, the athlete fits into. In one specific embodiment, a shoe can be offered in a limited number of different options with traction elements specifically set up for heel-strikers, midfoot strikers, and/or forefoot strikers.

One embodiment of the invention allows for the utilization of the methods and algorithms described herein to design and manufacture apparel and/or equipment for use by athletes and other users. For example, measurements of physical characteristics of an individual may be used to custom design articles of apparel such as, but not limited to, protective helmets, protective garments for the upper and/or lower body (e.g., shirts and/or pants incorporating protective material or sleeves and/or wraps incorporating protective material for placement on the limbs and/or torso of a wearer), protective padding, etc. Relevant performance measurements for an athlete carrying out a sporting activity can also be incorporated into the input parameters for ensuring that the apparel provides the protection required without sacrificing performance. For example, measurements of the shape and size of a head of an athlete can be used as input parameters for a method of designing a custom fitted helmet for that athlete. In one embodiment, input parameters can include measurements of the movements of the athlete (e.g., rotation of the neck and or change in shape of the neck due to flexing of the neck muscles), which can be used to customize the helmet further to limit the effect of the helmet on the athletic performance of the wearer without compromising the protection provided. In one embodiment customized padding (e.g., shoulder pads, elbow pads, torso padding, forearm padding, shin pads, hip padding, etc.) can be provided for an athlete by measuring the physical characteristics of the part of the body requiring protection and/or obtaining measurements relating to the movement of that body part during performance of the athletic activity for which the padding is designed. Customized helmets, apparel, and/or padding may be beneficial in sports such as, but not limited to, lacrosse, American football, ice hockey, field hockey, rugby, soccer, baseball, softball, martial arts, and/or boxing.

In one embodiment footwear and blades for skating (e.g., during ice hockey, speed skating, or ice dancing) may be customized for a particular skater based on physical characteristics of the wearer and/or performance characteristics of the wearer (e.g., relating to the skating style of the wearer and/or the particular movements carried out by the wearer during their particular athletic activities). As manufacturing methods such as, but not limited to, SLS allow for the manufacturing of components from many materials including both plastics and metals, multiple parts of a skate can be custom manufactured including, but not limited to, the blade, the blade attachment, the sole, and/or the upper.

One embodiment of the invention allows for the utilization of the methods and algorithms described herein to design and manufacture of sporting equipment (or elements thereof) such as, but not limited to, lacrosse heads, lacrosse nets, golf clubs, tennis racquets, gripping elements for any piece of sporting equipment, hockey sticks (and, for example, the head and/or gripping portions thereof) through use of physical characteristic of the user and/or performance characteristics of the user (e.g., through measurement of the forces, pressures, stresses, strains and/or flexion of the piece of sporting equipment during a specific athletes performance of an athletic activity).

It should be understood that alternative embodiments, and/or materials used in the construction of embodiments, or alternative embodiments, are applicable to all other embodiments described herein.

The invention may be embodied in other specific forms without departing from the spirit or essential characteristics thereof. The foregoing embodiments, therefore, are to be considered in all respects illustrative rather than limiting the invention described herein. Scope of the invention is thus indicated by the appended claims, rather than by the foregoing description, and all changes that come within the meaning and range of equivalency of the claims are intended to be embraced therein.

What is claimed is:

1. An article of footwear comprising:
   an upper; and
   a sole comprising a midsole, the midsole comprising:
      an upper surface positioned proximate the upper;
      a lower surface positioned away from the upper and comprising at least one positioning element, the at least one positioning element adapted to engage at least one ground contact element; and
      an intermediate portion extending between the upper surface and the lower surface and bounded by a side wall, wherein the intermediate portion comprises a continuous, three-dimensional open web structure, from a heel region to a forefoot region and from a lateral side to a medial side of the midsole, of elliptical elements forming faces of a plurality of spheroidal cells arranged to form a matrix of adjacent open cells of at least one of differing, varying, and non-uniform size and orientation from the heel region to the forefoot region, wherein:
         (i) the upper surface comprises a central region and an outer perimeter, the outer perimeter comprising a band of solid material surrounding the central region and extending around an entire perimeter of the upper surface, the band of solid material adapted to provide a bonding surface for adhering the upper to the sole, and the central region comprising an open web surface formed by an exposed upper surface of the open web structure;
         (ii) the side wall comprises at least a portion formed by the outer surface of the open web structure; and
         (iii) the lower surface comprises at least a portion formed by the outer surface of the open web structure.

2. The footwear of claim 1, wherein the midsole comprises a thermoplastic elastomer.

3. The footwear of claim 1, wherein the band of solid material comprises a coloring agent.

4. The footwear of claim 1, wherein the midsole is formed as a unitary construction using a selective laser sintering process.

5. The footwear of claim 1, wherein the band of solid material comprises a substantially constant width.

6. The footwear of claim 5, wherein the band of solid material comprises a width of between 10% to 20% of a width of at least a portion of the upper surface.

7. The footwear of claim 1, wherein the open web structure comprises a first portion and a second portion, wherein at least one structural parameter of the open web structure differs between the first portion and the second portion.

8. The footwear of claim 7, wherein the first portion comprises an edge region proximate the side wall and the second portion comprises at least a portion of a central region.

9. The footwear of claim 8, wherein the at least one structural parameter comprises a thickness of the elliptical elements, and the thickness of the elliptical elements is greater in at least a portion of the edge region than in at least a portion of the central region.

10. The footwear of claim 7, wherein the at least one structural parameter is selected from the group consisting of a thickness, a density, a length, and a cross-sectional shape of the elliptical elements, and wherein the at least one structural parameter relates to at least one of a size and a shape of the open cells.

11. The footwear of claim 10, wherein a value of the at least one structural parameter is controlled by at least one of a power and a tracking speed of a laser utilized by a selective laser sintering process to form the open web structure.

12. The footwear of claim 7, wherein the at least one structural parameter relates to at least one structural characteristic of the midsole selected from the group consisting of a cushioning characteristic, a flexibility characteristic, and a support characteristic.

13. The footwear of claim 7, wherein properties of the at least one structural parameter within each of the first portion and second portion are determined from at least one performance metric of a foot of one or more users.

14. The footwear of claim 13, wherein the performance metric is determined based at least in part on at least one input parameter, the at least one input parameter comprising at least one of a pressure, a friction, a force, a position, a velocity, an acceleration, a rotational velocity, a rotational acceleration, a change in shape of at least a portion of a foot, a mass distribution, an energy distribution, a stress, a strain, and a time over which an event occurs.

15. The footwear of claim 14, wherein the least one input parameter comprises at least one of pressure distribution measurements over at least a portion of a sole of the foot of a user and force distribution measurements between at least a portion of the sole of the foot and a ground surface during at least a portion of a ground contact phase of an athletic motion.

16. The footwear of claim 1, wherein the open web structure of interconnected elliptical elements forms a reticulated foam-like structure.

17. The footwear of claim 1, further comprising a plurality of positioning elements, with a ground contact element secured within each corresponding positioning element, the ground contact element comprising a rubber outsole element.

18. The footwear of claim 17, wherein each positioning element forms indents for receiving the corresponding ground contact element.

19. A midsole for an article of footwear, the midsole manufactured as a unitary construction using a single selective laser sintering process, the midsole consisting essentially of:
  an upper surface positioned proximate an upper;
  a lower surface positioned away from the upper and comprising a plurality of positioning elements, each of the positioning elements adapted to engage at least one ground contact element; and
  an intermediate portion extending between the upper surface and the lower surface and bounded by a side wall, wherein the intermediate portion comprises a continuous, three-dimensional open web structure, from a heel region to a forefoot region and from a lateral side to a medial side of the midsole, of elliptical elements forming faces of a plurality of spheroidal cells arranged to form a matrix of adjacent open cells, the continuous, three-dimensional open web structure comprising a first portion and a second portion with at least one structural parameter of the open web structure at least one of differing, varying, and non-uniform size and orientation between the first portion and the second portion, wherein:
    (i) the upper surface comprises a central region and an outer perimeter, the outer perimeter comprising a band of solid material surrounding the central region and extending around an entire perimeter of the upper surface, the band of solid material adapted to provide a bonding surface for adhering the upper to the midsole, and the central region comprising an open web surface formed by an exposed upper surface of the open web structure;
    (ii) the side wall comprises at least a portion formed by the outer surface of the open web structure; and
    (iii) the lower surface comprises at least a portion formed by the outer surface of the open web structure.

20. A midsole for an article of footwear, the midsole manufactured as a unitary construction using a single selective laser sintering process, the midsole consisting essentially of:
  an upper surface positioned proximate an upper;
  a lower surface positioned away from the upper and comprising a plurality of positioning elements, each of the positioning elements adapted to engage at least one ground contact element; and
  an intermediate portion extending between the upper surface and the lower surface and bounded by a side wall, wherein the intermediate portion comprises a continuous, three-dimensional open web structure, from a heel region to a forefoot region and from a lateral side to a medial side of the midsole, of elliptical elements forming faces of a plurality of spheroidal cells arranged to form a matrix of adjacent open cells, the continuous, three-dimensional open web structure comprising a first portion and a second portion with at least one structural parameter of the open web structure at least one of differing, varying, and non-uniform size and orientation between the first portion and the second portion, wherein:
    (i) the upper surface comprises a central region and an outer perimeter, the outer perimeter comprising a closed band of solid material surrounding the central region and extending around an entire perimeter of the upper surface, the closed band of solid material adapted to provide a bonding surface for adhering the upper to the midsole, and the central region comprising an open web surface formed by an exposed upper surface of the open web structure;
    (ii) the side wall comprises at least a portion formed by the outer surface of the open web structure; and
    (iii) the lower surface comprises at least a portion formed by the outer surface of the open web structure.

21. The footwear of claim 1, wherein the adjacent open cells of the plurality of spheroidal cells share common elliptical elements.

22. The midsole of claim 19, wherein the adjacent open cells of the plurality of spheroidal cells share common elliptical elements.

23. The midsole of claim 20, wherein the adjacent open cells of the plurality of spheroidal cells share common elliptical elements.

* * * * *